US009162967B2

(12) United States Patent
Ohashi et al.

(10) Patent No.: US 9,162,967 B2
(45) Date of Patent: Oct. 20, 2015

(54) SULFONIUM SALT, POLYMER, RESIST COMPOSITION, AND PATTERNING PROCESS

(71) Applicant: SHIN-ETSU CHEMICAL CO., LTD., Tokyo (JP)

(72) Inventors: Masaki Ohashi, Joetsu (JP); Jun Hatakeyama, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 67 days.

(21) Appl. No.: 13/905,756

(22) Filed: May 30, 2013

(65) Prior Publication Data
US 2013/0337378 A1     Dec. 19, 2013

(30) Foreign Application Priority Data
Jun. 15, 2012     (JP) .................. 2012-135462

(51) Int. Cl.
| C07C 69/52 | (2006.01) |
| G03F 7/039 | (2006.01) |
| C07C 69/54 | (2006.01) |
| G03F 7/027 | (2006.01) |
| G03F 7/004 | (2006.01) |
| G03F 7/20 | (2006.01) |
| G03F 7/038 | (2006.01) |

(52) U.S. Cl.
CPC .............. *C07C 69/54* (2013.01); *G03F 7/0041* (2013.01); *G03F 7/0045* (2013.01); *G03F 7/027* (2013.01); *G03F 7/0395* (2013.01); *G03F 7/20* (2013.01); *G03F 7/2041* (2013.01)

(58) Field of Classification Search
None
See application file for complete search history.

(56) References Cited

U.S. PATENT DOCUMENTS

| 4,130,543 | A | * | 12/1978 | Doorakian et al. ............ 528/125 |
| 4,477,640 | A | * | 10/1984 | Schmidt et al. ............... 526/256 |
| 4,839,203 | A | * | 6/1989 | Davis et al. ................... 427/244 |
| 4,885,355 | A | * | 12/1989 | Wessling et al. ............... 528/99 |
| 5,610,443 | A | * | 3/1997 | Inagaki et al. ................ 257/788 |
| 5,650,483 | A | | 7/1997 | Malik et al. |
| 5,945,250 | A | | 8/1999 | Aoai et al. |
| 6,312,867 | B1 | | 11/2001 | Kinsho et al. |
| 6,352,576 | B1 | * | 3/2002 | Spencer et al. ................. 95/236 |
| 6,590,051 | B1 | * | 7/2003 | Carter et al. .................. 526/258 |
| 6,830,866 | B2 | | 12/2004 | Kobayashi et al. |
| 7,511,169 | B2 | | 3/2009 | Ohsawa et al. |
| 7,527,912 | B2 | | 5/2009 | Ohsawa et al. |
| 7,569,326 | B2 | | 8/2009 | Ohsawa et al. |
| 7,622,242 | B2 | | 11/2009 | Hatakeyama et al. |
| 7,771,914 | B2 | | 8/2010 | Hatakeyama et al. |
| 7,932,334 | B2 | | 4/2011 | Ando et al. |
| 7,956,142 | B2 | | 6/2011 | Nagai et al. |
| 8,057,981 | B2 | | 11/2011 | Harada et al. |
| 8,057,985 | B2 | | 11/2011 | Ohashi et al. |
| 8,084,183 | B2 | | 12/2011 | Yamashita et al. |
| 8,101,335 | B2 | | 1/2012 | Harada et al. |
| 8,114,570 | B2 | | 2/2012 | Ohsawa et al. |
| 8,114,571 | B2 | | 2/2012 | Ohashi et al. |
| 8,173,354 | B2 | | 5/2012 | Ohsawa et al. |
| 8,252,504 | B2 | | 8/2012 | Harada et al. |
| 8,268,528 | B2 | | 9/2012 | Harada et al. |
| 8,283,104 | B2 | | 10/2012 | Ohashi et al. |
| 8,313,886 | B2 | | 11/2012 | Harada et al. |
| 8,431,323 | B2 | | 4/2013 | Watanabe et al. |
| 8,435,717 | B2 | | 5/2013 | Hagiwara et al. |
| 2002/0015826 | A1 | * | 2/2002 | Desmarteau et al. ......... 428/195 |
| 2005/0208424 | A1 | | 9/2005 | Hasegawa et al. |
| 2014/0322650 | A1 | * | 10/2014 | Ohashi et al. ............. 430/281.1 |

FOREIGN PATENT DOCUMENTS

| JP | 04-230645 A | 8/1992 |
| JP | 2000-336121 A | 12/2000 |
| JP | 2003-66612 A | 3/2003 |
| JP | 3613491 B2 | 1/2005 |
| JP | 2005-84365 A | 3/2005 |
| JP | 2005-264103 A | 9/2005 |
| JP | 2007-145797 A | 6/2007 |
| JP | 2007-197718 A | 8/2007 |
| JP | 2007-298569 A | 11/2007 |
| JP | 2008-106045 A | 5/2008 |
| JP | 2008-122932 A | 5/2008 |
| JP | 2008-133448 A | 6/2008 |
| JP | 2009-7327 A | 1/2009 |
| JP | 2009-37057 A | 2/2009 |
| JP | 2009-98638 A | 5/2009 |
| JP | 2009-191151 A | 8/2009 |
| JP | 2009-192784 A | 8/2009 |
| JP | 2009-258695 A | 11/2009 |
| JP | 2009-269953 A | 11/2009 |
| JP | 2009-276363 A | 11/2009 |
| JP | 2010-20204 A | 1/2010 |
| JP | 2010-77404 A | 4/2010 |
| JP | 2010-107695 A | 5/2010 |
| JP | 2010-134012 A | 6/2010 |
| JP | 2010-215608 A | 9/2010 |
| JP | 2010-250105 A | 11/2010 |
| JP | 2011-16746 A | 1/2011 |
| JP | 2011-42789 A | 3/2011 |
| JP | 2012-48075 A | 3/2012 |
| WO | 2008/056795 A1 | 5/2008 |

* cited by examiner

*Primary Examiner* — Cynthia Hamilton
(74) *Attorney, Agent, or Firm* — Westerman, Hattori, Daniels & Adrian, LLP

(57) ABSTRACT

A sulfonium salt comprising (a) a polymerizable substituent, (b) asulfonium cation, and (c) a sulfonate anion within a common molecule is capable of generating a sulfonic acid in response to high-energy radiation or heat. A resist composition comprising the sulfonium salt as base resin has high resolution and is suited for precise micropatterning by ArF immersion, EB or EUV lithography.

2 Claims, No Drawings

SULFONIUM SALT, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2012-135462 filed in Japan on Jun. 15, 2012, the entire contents of which are hereby incorporated by reference.

TECHNICAL FIELD

This invention relates to (1) a sulfonium salt comprising (a) a polymerizable substituent, (b) a sulfonium cation, and (c) a sulfonate anion within a common molecule, capable of generating a sulfonic acid in response to high-energy radiation or heat, (2) a polymer comprising recurring units derived from the sulfonium salt, (3) a resist composition comprising the polymer, and (4) a patterning process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using an ArF excimer laser as the light source is requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. The ArF immersion lithography is now implemented on the commercial stage. As the exposure technology following the ArF lithography, EB and EUV lithography processes are regarded promising.

As the circuit line width is reduced by the recent rapid advance of technology, the degradation of contrast by acid diffusion becomes more serious for the resist material. This is because the pattern feature size is approaching the diffusion length of acid. Acid diffusion leads to degradations of mask fidelity and pattern rectangularity and non-uniformity of a fine line pattern, i.e., line width roughness (LWR). Accordingly, to gain more benefits from a reduction of exposure light wavelength and an increase of lens NA, an increase in dissolution contrast and suppression of acid diffusion are required more than in the prior art resist materials.

One approach to overcome these problems is to bind a PAG in a polymer. For instance, aiming to improve sensitivity, Patent Document 1 proposes a polymer using an acryloyloxyphenyldiphenylsulfonium salt as a monomer. Patent Document 2 proposes to incorporate the monomer into a polyhydroxystyrene resin for improving the LWR of this base resin. However, since the sulfonium salt is bound at its cation side to the polymer, the sulfonic acid generated therefrom upon exposure to high-energy radiation is equivalent to the sulfonic acids generated by conventional PAGs. These proposals are thus unsatisfactory to overcome the outstanding problems. Also, aiming to improve sensitivity and resist pattern profile, Patent Document 3 discloses sulfonium salts having an anion side incorporated into the polymer backbone such as polystyrenesulfonic acid. The acids generated therefrom are arenesulfonic and alkylsulfonic acid derivatives which have too low an acid strength to sever acid labile groups, especially acid labile groups in acrylate-derived base resins. The acrylate resins are commonly used not only in the ArF chemically amplified lithography offering a fine feature size, but also in the EB and EUV lithography processes. Also a variety of anion-bound resins capable of generating an acid having high acid strength have been developed. Patent Document 4 discloses a polymer having a difluoroethanesulfonic acid anion in the backbone. Patent Documents 5 and 6 disclose a polymerizable sulfonium salt having a partially fluorinated sulfonic acid anion and a resin obtained therefrom. Acid diffusion is suppressed by incorporating a strong acid-generating anion in the backbone of a base resin. Thus, some improvements are made in resist properties including mask fidelity, pattern rectangularity and LWR.

The lithography techniques which are considered promising next to the ArF lithography include electron beam (EB) lithography and extreme ultraviolet (EUV) lithography. In these techniques, exposure must be done in vacuum or reduced pressure, which allows the sulfonic acid generated during exposure to volatilize, failing to form a satisfactory pattern profile. Such volatile sulfonic acids or volatile sulfonium cation decomposition products (e.g., phenylsulfides) induce so-called "outgassing," causing damages to the exposure system.

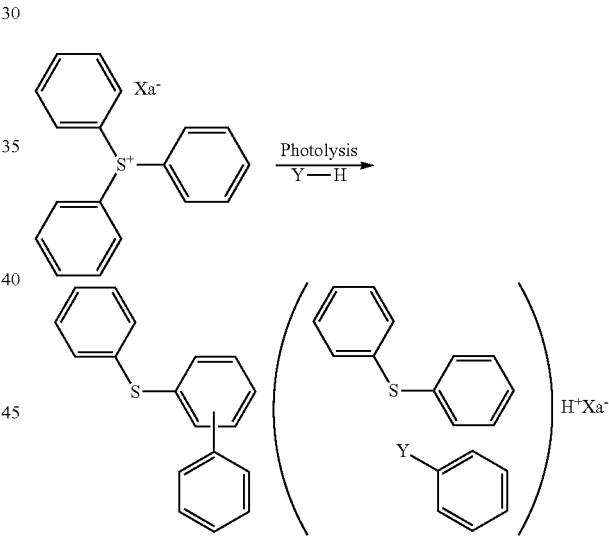

Herein Y—H denotes a proton donor such as a polymer matrix, and Xa⁻ is an anion. The photo-decomposed product is exemplary while more complex photo-decomposed products may form. Some approaches are taken to reduce the outgassing from acid generators, as described, for example, in Patent Document 7.

CITATION LIST

Patent Document 1: JP-A H04-230645
Patent Document 2: JP-A 2005-084365
Patent Document 3: JP 3613491 (U.S. Pat. No. 5,945,250)
Patent Document 4: JP-A 2007-197718 (U.S. Pat. No. 7,932,334)
Patent Document 5: WO 08/056,795
Patent Document 6: JP-A 2008-133448 (U.S. Pat. No. 7,569,326)
Patent Document 7: JP-A 2009-037057 (U.S. Pat. No. 8,084,183)

DISCLOSURE OF INVENTION

An object of the invention is to provide (1) a sulfonium salt, (2) a polymer comprising recurring units derived from the sulfonium salt, (3) a resist composition comprising the polymer, and (4) a patterning process using the resist composition, wherein the resist composition exhibits a high resolution when processed by photolithography using high-energy radiation such as ArF excimer laser, EB or EUV.

The inventors have found that a resist composition using a polymer comprising recurring units of a sulfonium salt having (a) a polymerizable substituent, (b) a sulfonium cation, and (c) a sulfonate anion within a common molecule, exhibits a high resolution when processed by photolithography. The resist composition is very effective for precise micropatterning.

In one aspect, the invention provides a sulfonium salt comprising (a) a polymerizable substituent, (b) a sulfonium cation, and (c) a sulfonate anion within a common molecule, capable of generating a sulfonic acid in response to high-energy radiation or heat.

Specifically, the sulfonium salt has the general formula (1A), (1B) or (1C).

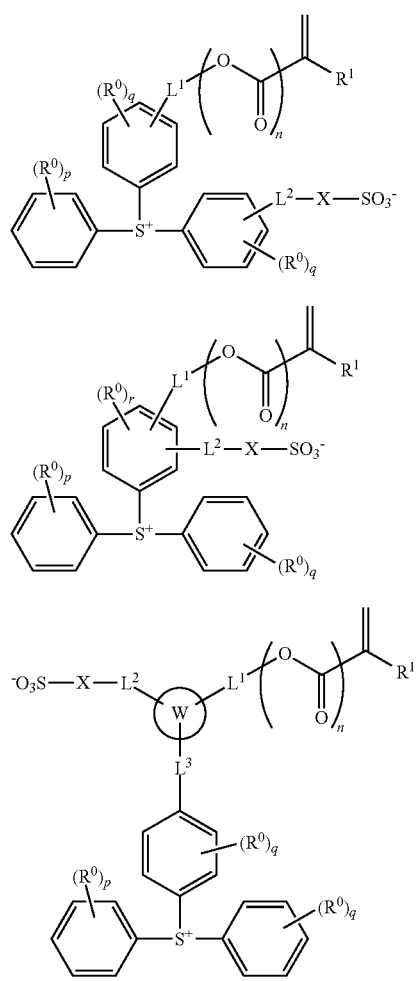

Herein $R^0$ is a $C_1$-$C_{20}$ monovalent hydrocarbon group which may be substituted with or separated by a heteroatom, $R^1$ is hydrogen, methyl or trifluoromethyl, $L^1$, $L^2$ and $L^3$ are each independently a single bond or a $C_1$-$C_{20}$ straight, branched or cyclic, divalent hydrocarbon group which may be substituted with or separated by a heteroatom, X is a $C_1$-$C_5$ divalent alkylene group in which some or all hydrogen atoms may be substituted by fluorine atoms, W is a $C_3$-$C_{30}$ trivalent aliphatic or aromatic ring, n is 0 or 1, p is an integer of 0 to 5, q is an integer of 0 to 4, and r is an integer of 0 to 3.

More preferably, the sulfonium salt has the general formula (2A), (2B) or (2C).

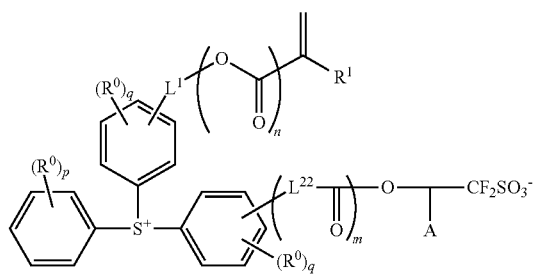

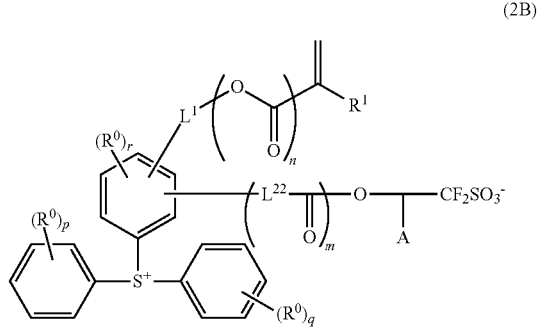

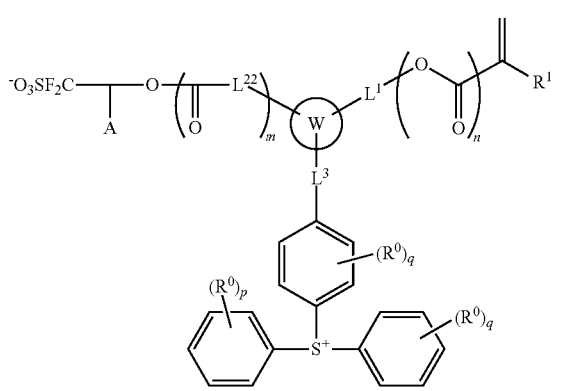

Herein $R^0$, $R^1$, $L^1$, $L^3$, W, n, p, q and r are as defined above, $L^{22}$ is a single bond or a $C_1$-$C_{20}$ straight, branched or cyclic, divalent hydrocarbon group which may be substituted with or separated by a heteroatom, A is hydrogen or trifluoromethyl, and m is 0 or 1.

In a second aspect, the invention provides a polymer comprising recurring units having the general formula (3A), (3B) or (3C).

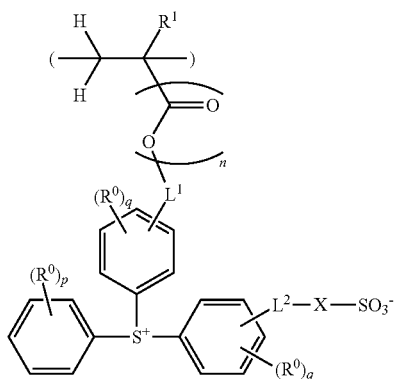
(3A)
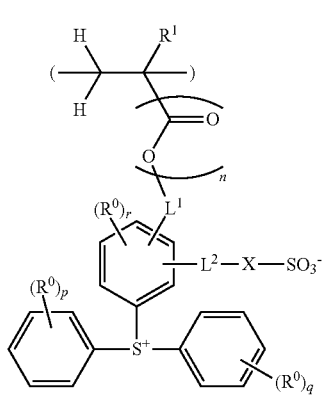
(3B)
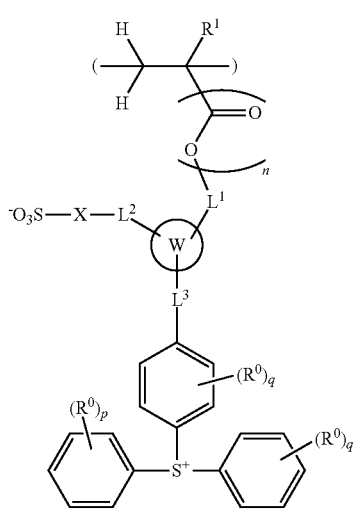
(3C)
Herein $R^0$, $R^1$, $L^1$, $L^2$, $L^3$, X, W, n, p, q and r are as defined above.
The polymer is preferably defined as comprising recurring units having the general formula (4A), (4B) or (4C).
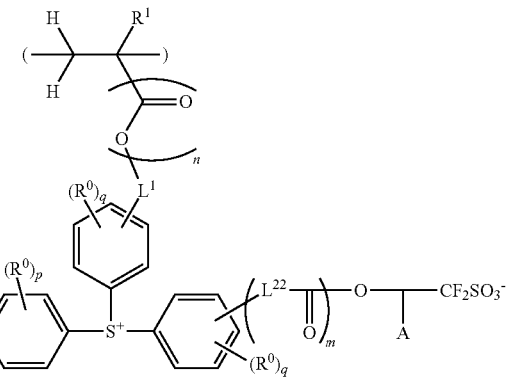
(4A)
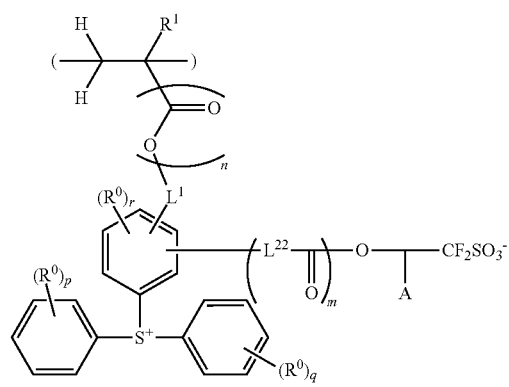
(4B)
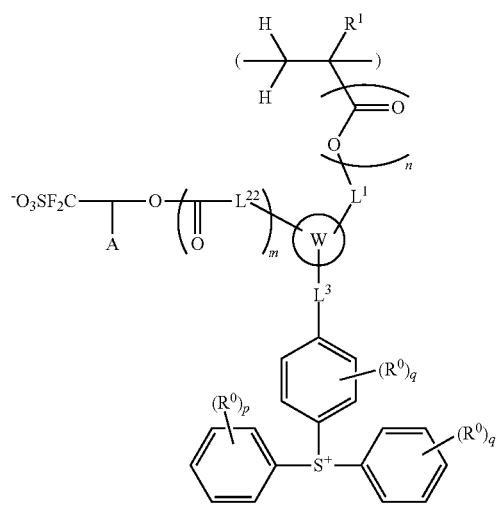
(4C)
Herein $R^0$, $R^1$, $L^1$, $L^3$, $L^{22}$, W, n, p, q, r, m, and A are as defined above.

Also preferably the polymer may further comprise recurring units having the general formula (5) or (6).

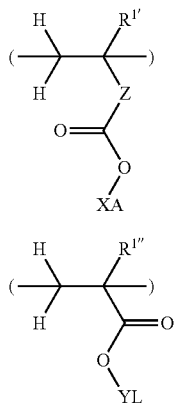

Herein $R^{1'}$ and $R^{1'''}$ are each independently hydrogen, methyl or trifluoromethyl, Z is a single bond, phenylene group, naphthylene group or (backbone)-C(=O)—O—Z'—, Z' is a straight, branched or cyclic $C_1$-$C_{10}$ alkylene group which may contain a hydroxyl radical, ether bond, ester bond or lactone ring, or phenylene group or naphthylene group, XA is an acid labile group, and YL is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

In a third aspect, the invention provides a resist composition comprising a polymer comprising recurring units having formula (3A), (3B), (3C), (4A), (4B) or (4C) as a base resin, or a resist composition comprising a polymer comprising recurring units having formula (3A), (3B), (3C), (4A), (4B) or (4C) and a polymer free of recurring units having formulae (3A), (3B), (3C), (4A), (4B) and (4C) as a base resin. The resist composition may further comprise a basic compound, an organic solvent, and optionally a non-polymeric acid generator and/or a surfactant which is insoluble in water and soluble in alkaline developer.

In a fourth aspect, the invention provides a pattern forming process comprising the steps of applying the resist composition defined above onto a substrate to form a coating, baking, exposing the coating to high-energy radiation, and developing the exposed coating in a developer.

In a preferred embodiment, the exposure step is carried out by immersion lithography using a liquid having a refractive index of at least 1.0 between the resist coating and a projection lens. Often, a protective film is coated on the resist coating prior to the exposure step, whereupon immersion lithography is carried out while the liquid is held between the protective film and the projection lens.

Typically, the high-energy radiation is electron beam or soft X-ray having a wavelength of 3 to 15 nm.

ADVANTAGEOUS EFFECTS OF INVENTION

A resist composition using the inventive sulfonium salt as base resin is improved in resolution and thus best suited for precise micropatterning by photolithography, especially ArF immersion, EB and EUV lithography processes.

DESCRIPTION OF EMBODIMENTS

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group.

The abbreviations have the following meaning.
EB: electron beam
UV: ultraviolet
EUV: extreme ultraviolet
PAG: photoacid generator
PEB: post-exposure bake
LWR: line width roughness The term "high-energy radiation" is intended to encompass UV, deep UV, EUV, EB, x-ray, excimer laser, gamma-ray and synchrotron radiation.

One embodiment of the invention is a sulfonium salt comprising (a) a polymerizable substituent, (b) a sulfonium cation, and (c) a sulfonate anion within a common molecule, capable of generating a sulfonic acid in response to high-energy radiation or heat.

Specifically, the sulfonium salt has the general formula (1A), (1B) or (1C).

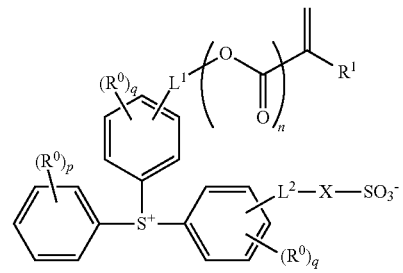

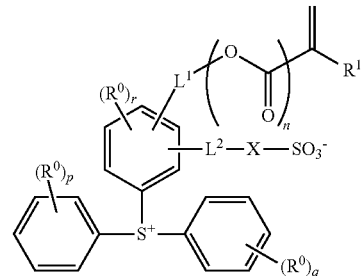

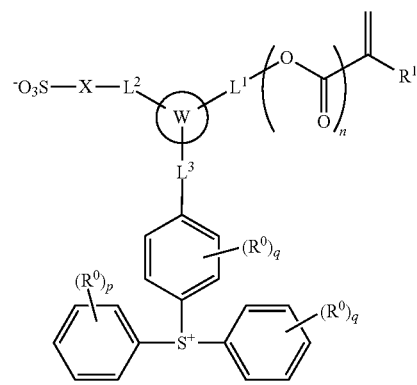

Herein $R^0$ is a $C_1$-$C_{20}$ monovalent hydrocarbon group which may be substituted with or separated by a heteroatom. $R^1$ is hydrogen, methyl or trifluoromethyl. $L^1$, $L^2$ and $L^3$ are each independently a single bond or a $C_1$-$C_{20}$ straight, branched or cyclic, divalent hydrocarbon group which may be substituted with or separated by a heteroatom. X is a $C_1$-$C_5$ divalent alkylene group in which some or all hydrogen atoms may be substituted by fluorine atoms. W is a $C_3$-$C_{30}$ trivalent aliphatic or aromatic ring, n is 0 or 1, p is an integer of 0 to 5, q is an integer of 0 to 4, and r is an integer of 0 to 3.

More particularly, in formulae (1A), (1B) and (1C), $R^1$ is hydrogen, methyl or trifluoromethyl. $L^1$, $L^2$ and $L^3$ are each independently a single bond or a straight, branched or cyclic, divalent hydrocarbon group of 1 to 20 carbon atoms which may be substituted with a heteroatom or separated by a heteroatom. Suitable divalent hydrocarbon groups include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; branched alkanediyl groups obtained by adding a side chain such as methyl, ethyl, propyl, isopropyl, butyl, sec-butyl or tert-butyl to the foregoing straight alkanediyl groups; saturated cyclic hydrocarbon groups such as cyclopentanediyl, cyclohexanediyl, norbornanediyl, and adamantanediyl; and unsaturated cyclic hydrocarbon groups such as phenylene and naphthylene. $L^1$ and $L^2$ may also be a combination of two or more of the foregoing groups. Also included are substituted forms of the foregoing groups in which one or more hydrogen atoms are substituted by a heteroatom or atoms such as oxygen, sulfur, nitrogen, and halogen or a heteroatom may intervene between carbon atoms. As a result of substitution or separation, a hydroxyl, cyano, carbonyl, carboxyl, ether bond, ester bond, sulfonic acid ester bond, carbonate bond, lactone ring, sultone ring, carboxylic anhydride or haloalkyl group may form or intervene.

In formulae (1A), (1B) and (1C), X is a divalent alkylene group of 1 to 5 carbon atoms in which some or all hydrogen atoms may be substituted by fluorine atoms. Suitable alkylene groups include methylene, ethylene, propane-1,3-diyl, butane-1,4-diyl, pentane-1,5-diyl, difluoromethylene, tetrafluoroethylene, 1,1,2-trifluoroethylene, hexafluoropropane-1,3-diyl, and octafluorobutane-1,4-diyl.

In formula (1C), W is a trivalent aliphatic or aromatic ring of 3 to 30 carbon atoms. Suitable aliphatic rings include cyclepentane, cyclohexane, norbornane, oxanorbornane, and adamantane rings, with adamantane being preferred. Suitable aromatic rings include benzene, naphthalene, and anthracene rings, with benzene being preferred.

In formulae (1A), (1B) and (1C), $R^0$ is a monovalent hydrocarbon group of 1 to 20 carbon atoms which may be substituted with a heteroatom or separated by a heteroatom. Suitable monovalent hydrocarbon groups include methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl. Also included are substituted forms of the foregoing groups in which one or more hydrogen atoms are substituted by a heteroatom or atoms such as oxygen, sulfur, nitrogen, and halogen or which may be separated by a heteroatom such as oxygen, sulfur or nitrogen. As a result of substitution or separation, a hydroxyl, cyano, carbonyl, carboxyl, ether bond, ester bond, sulfonic acid ester bond, carbonate bond, lactone ring, sultone ring, carboxylic anhydride or haloalkyl group may form or intervene. Inter alia, methyl, methoxy, tert-butyl and tert-butoxy are preferred.

The subscript p is an integer of 0 to 5, preferably 0, 1 or 2; q is an integer of 0 to 4, preferably 0, 1 or 2; and r is an integer of 0 to 3, preferably 0 or 1.

More preferably, the sulfonium salt having formula (1A), (1B) or (1C) has the general formula (2A), (2B) or (2C).

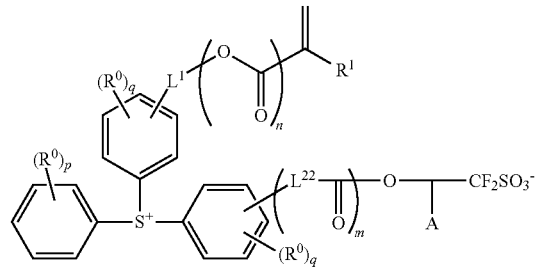

(2A)

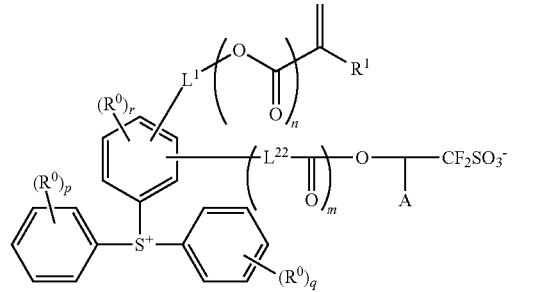

(2B)

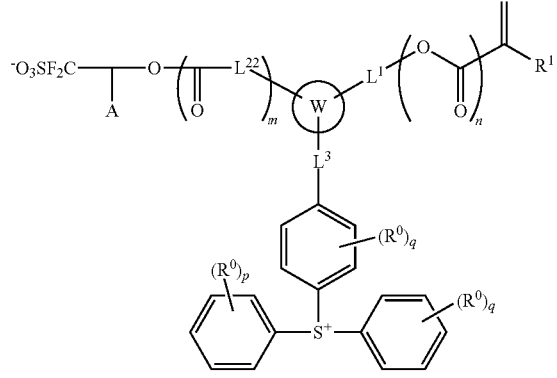

(2C)

Herein $R^0$, $R^1$, $L^1$, $L^3$, W, n, p, q and r are as defined above, $L^{22}$ is a single bond or a $C_1$-$C_{20}$ straight, branched or cyclic, divalent hydrocarbon group which may be substituted with or separated by a heteroatom, A is hydrogen or trifluoromethyl, and m is 0 or 1.

In formulae (2A), (2B) and (2C), A is hydrogen or trifluoromethyl. $L^{22}$ is a single bond or a straight, branched or cyclic, divalent hydrocarbon group of 1 to 20 carbon atoms which may be substituted with a heteroatom or separated by a heteroatom. Suitable divalent hydrocarbon groups include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; branched alkanediyl groups obtained by adding a side chain such as methyl, ethyl, propyl, isopropyl, butyl, sec-butyl or tert-butyl to the foregoing straight alkanediyl groups; saturated cyclic hydrocarbon groups such as cyclopentanediyl, cyclohexanediyl, norbornanediyl, and adamantanediyl; and unsaturated cyclic hydrocarbon groups such as phenylene and naphthylene. $L^{22}$ may also be a combination of two or more of the foregoing groups. Also included are substituted forms of the foregoing groups in which one or more hydrogen atoms are substituted by a heteroatom or atoms such as oxygen, sulfur, nitrogen, and halogen or which may be separated by a heteroatom such as oxygen, sulfur or nitrogen. As a result of substitution or separation, a hydroxyl, cyano, carbonyl, carboxyl, ether bond, ester bond, sulfonic acid ester bond, carbonate bond, lactone ring, sultone ring, carboxylic anhydride or haloalkyl group may form or intervene.

In formulae (2A), (2B) and (2C), $L^{22}$ is preferably a single bond or a structure having the general formula (7A) or (7B).

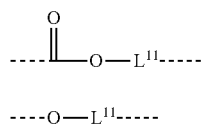
(7A)

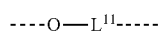
(7B)

Herein $L^{11}$ is a divalent alkylene group of 1 to 5 carbon atoms. The broken line denotes a valence bond. The broken line extending from $L^{11}$ is bonded to the carbonyl group adjacent to $L^{22}$ in formula (2A), (2B) or (2C).

In formulae (7A) and (7B), exemplary groups of $L^{11}$ include methylene, ethylene, propane-1,3-diyl, butane-1,4-diyl and pentane-1,5-diyl.

Exemplary structures of the sulfonium salt are shown below, but not limited thereto.

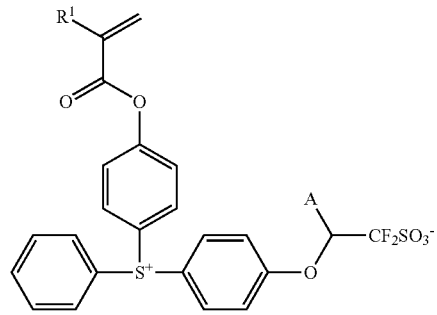

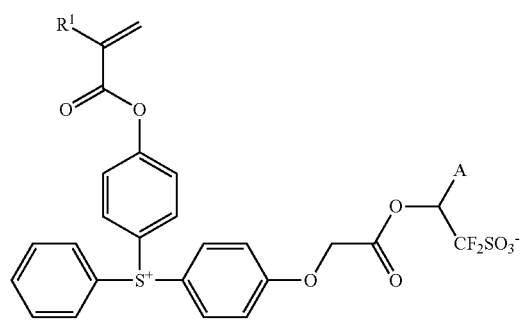

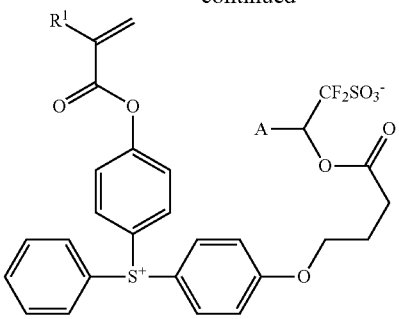

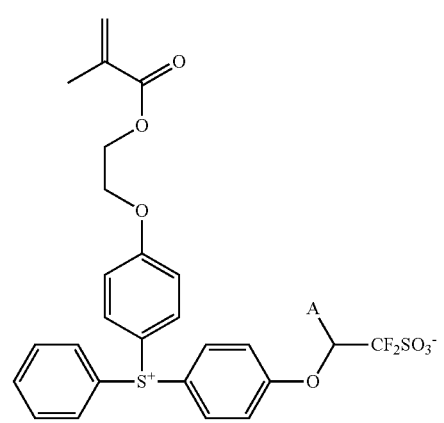

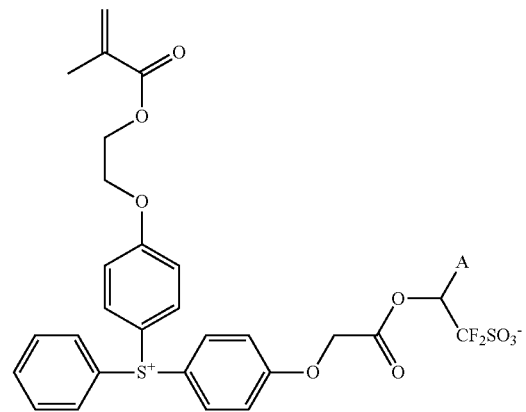

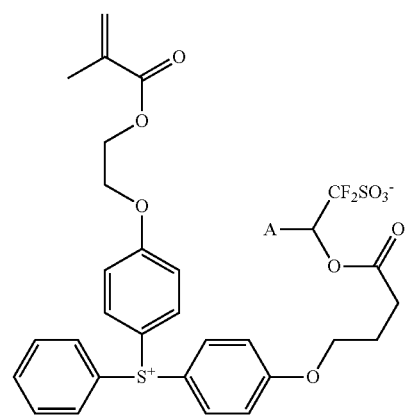

-continued
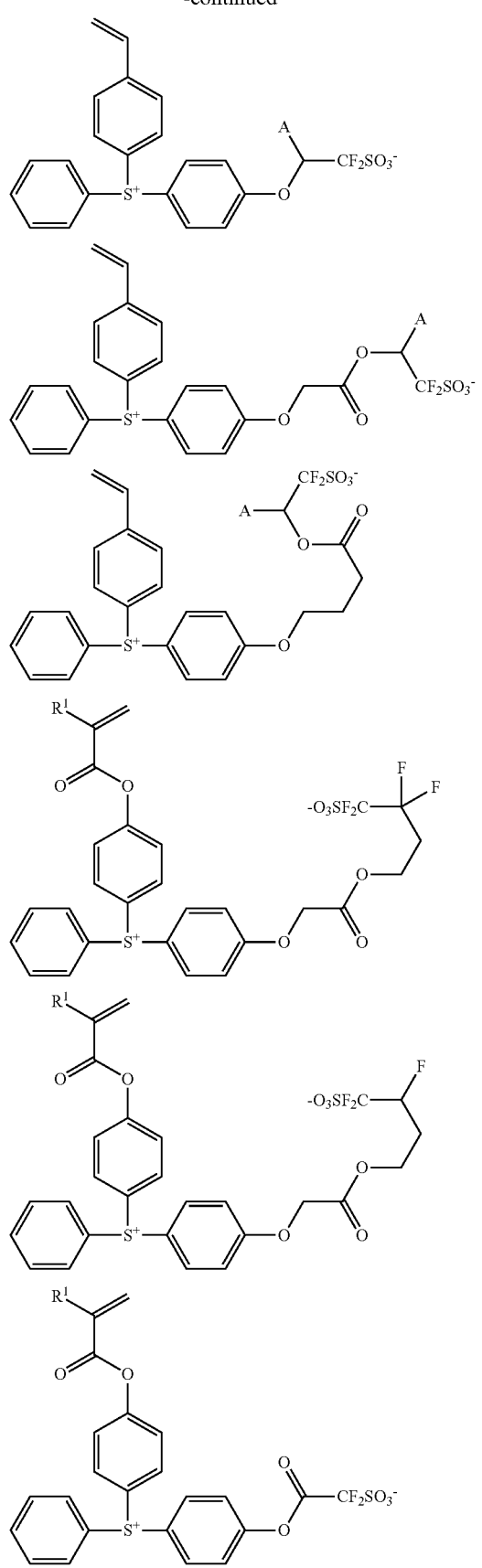
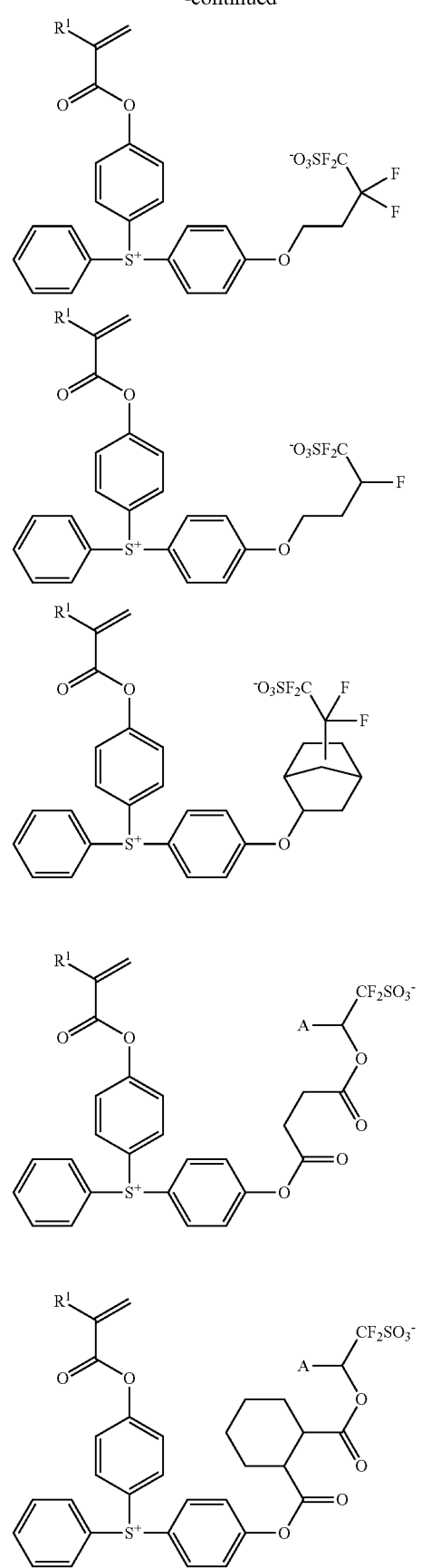

-continued
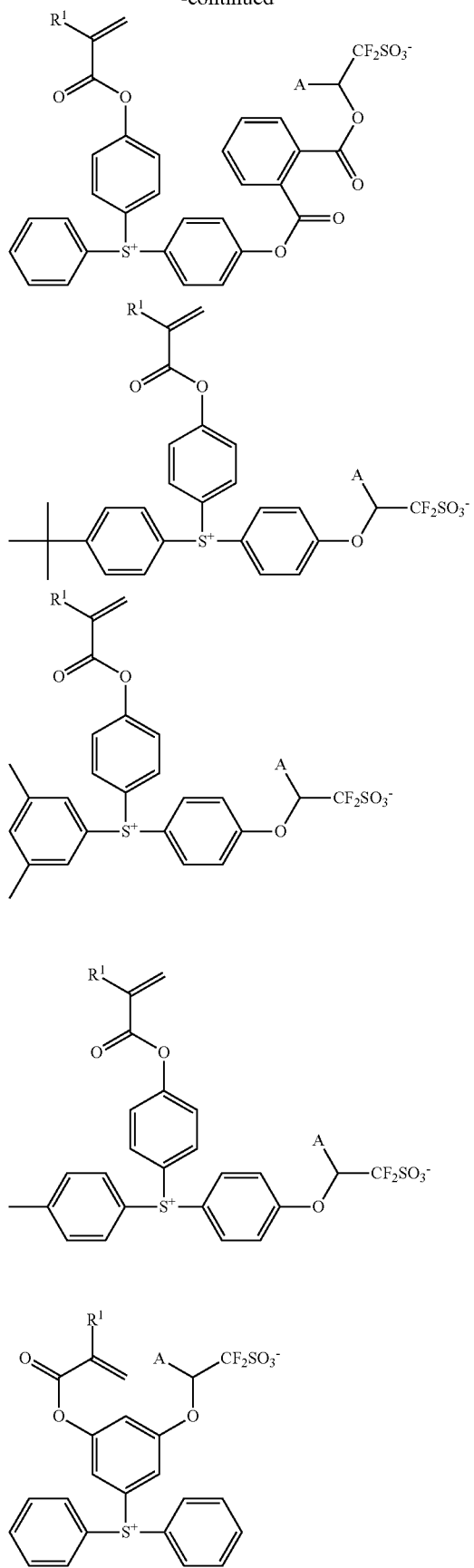
-continued
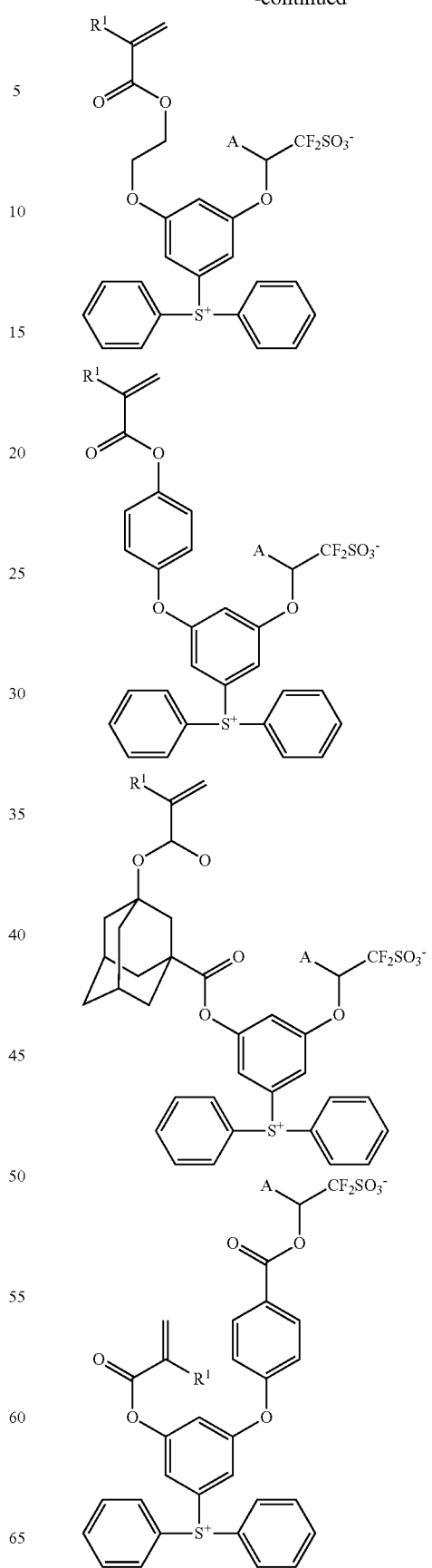

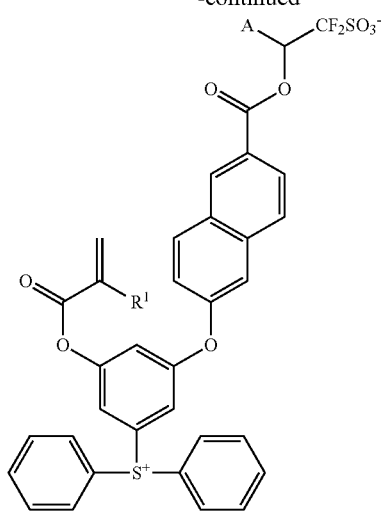
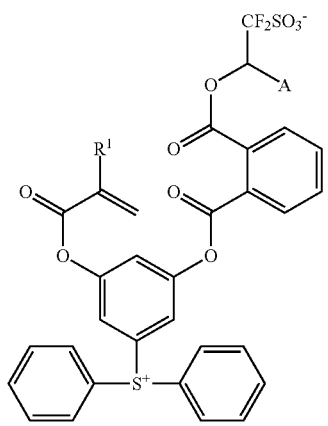
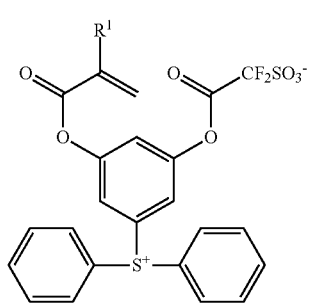
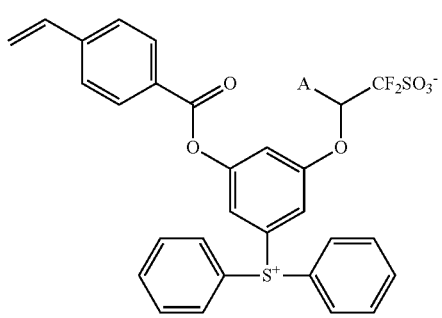
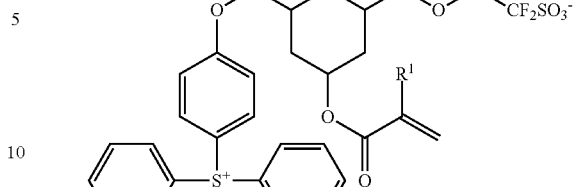
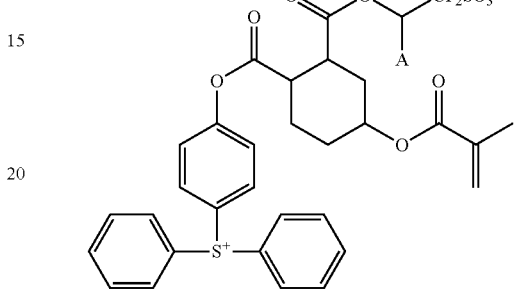
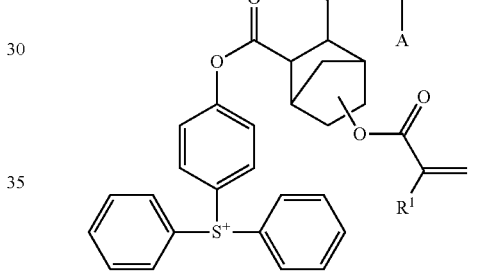
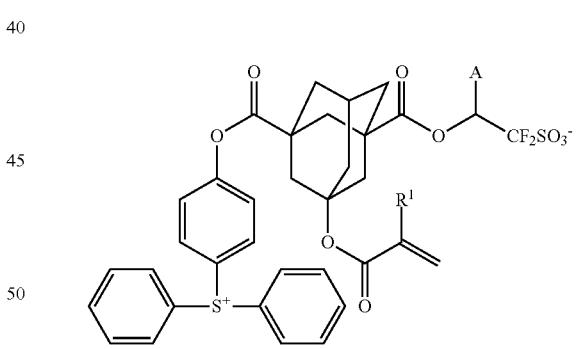
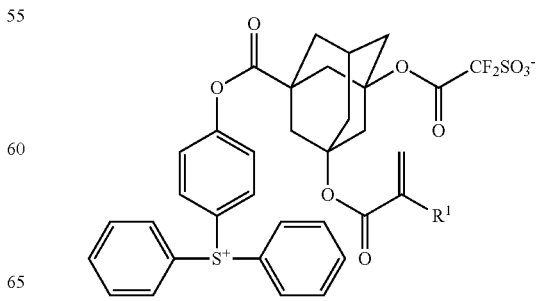

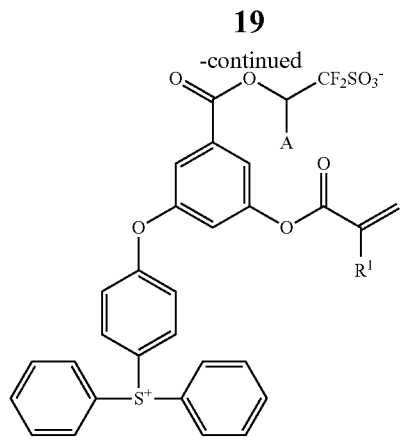

In these formulae, $R^1$ and A are as defined above.

It is now described how to synthesize these sulfonium salts. First, the synthesis of a sulfonium salt having formula (1A) or (2A) is illustrated. The synthesis of a sulfonium salt having formula (1A) or (2A) may be carried out, for example, by a reaction of sulfo-containing benzene with diaryl sulfoxide in the presence of an acid catalyst as shown by the following Scheme 1.

Scheme 1

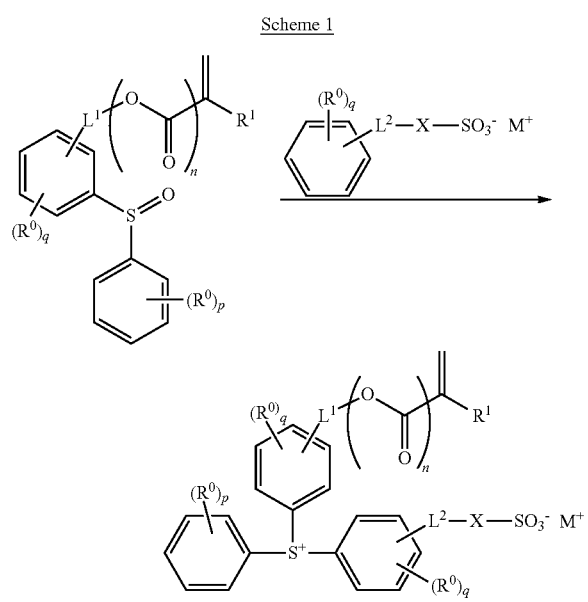

Herein $R^0$, $R^1$, $L^1$, $L^2$, X, n, p and q are as defined above, and $M^+$ is a cation.

A typical acid catalyst is methanesulfonic acid-diphosphorus pentoxide. Although a polymerizable functional group is attached to the diaryl sulfoxide in Scheme 1, it may be introduced after the preparation of sulfonium cation. The polymerizable functional group may be introduced by any well-known organic chemistry, typically esterification.

In another route utilizing a nucleophilic displacement reaction between fluorophenyldiarylsulfonium and sulfoalcohol, a sulfonium salt having formula (1A) wherein (-$L^2$-X—) is (—O-$L^{2a}$-X—) may be synthesized via intramolecular reaction. Herein $L^{2a}$ is a single bond or a straight, branched or cyclic, divalent hydrocarbon group of 1 to 20 carbon atoms which may be substituted with or separated by a heteroatom. This reaction is outlined by the following Scheme 2.

Scheme 2

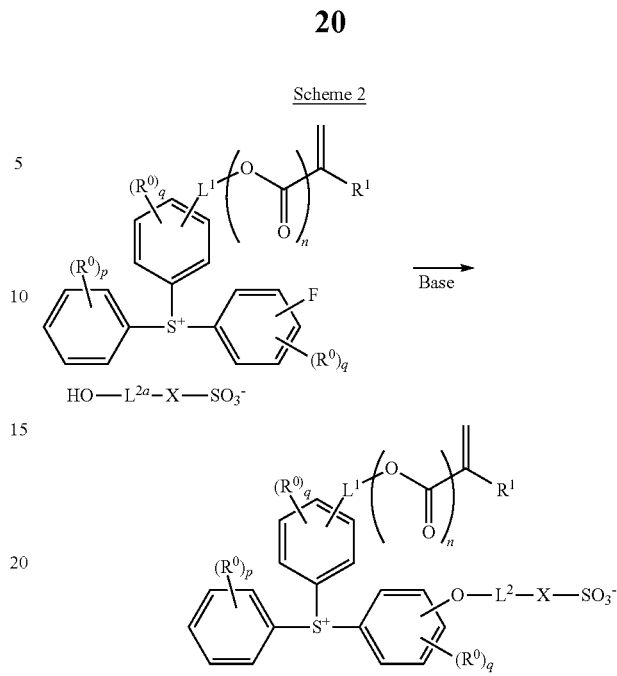

Herein $R^0$, $R^1$, $L^1$, X, n, p and q are as defined above, and $L^{2a}$ is a single bond or a straight, branched or cyclic, divalent hydrocarbon group of 1 to 20 carbon atoms which may be substituted with or separated by a heteroatom.

Although the synthesis example via intramolecular reaction is illustrated herein, the nucleophilic displacement reaction between fluorophenyldiarylsulfonium and sulfoalcohol may similarly take place in a non-intramolecular way. Also, like Scheme 1, the polymerizable functional group may be introduced either before or after the reaction.

Other synthesis routes include an addition reaction of hydrogensulfite ion to a sulfonium salt having terminal olefin and a reaction of a corresponding halide with a sulfur compound. These reactions are outlined by the following Schemes 3 and 4.

Scheme 3

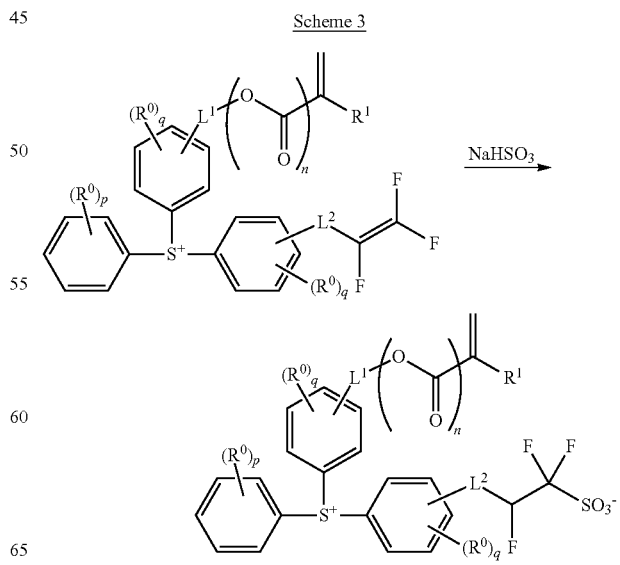

Scheme 4

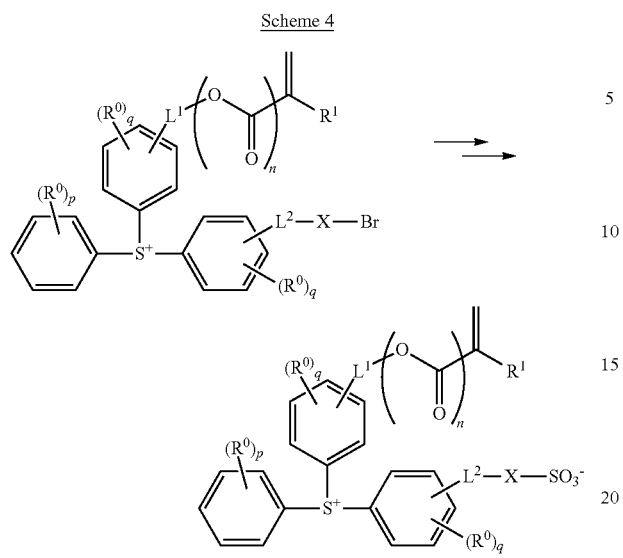

Herein $R^0$, $R^1$, $L^1$, $L^2$, X, n, p and q are as defined above.

The synthesis of a sulfonium salt having formula (1B) or (2B) may be carried out, for example, by utilizing nucleophilic displacement reaction similar to Scheme 2. A sulfonium salt having formula (1B) or (2B) may be synthesized by replacing the fluorine atom on difluorophenyldiphenylsulfonium salt. Also, the desired sulfonium salt may be obtained by esterifying or etherifying the hydroxyl group on dihydroxydiphenylsulfonium salt, for example.

A sulfonium salt having formula (1C) or (2C) may be synthesized by reacting a cyclic compound having a sulfo and polymerizable group with a hydroxyphenyldiphenylsulfonium salt. This reaction is outlined by the following Scheme 5.

Scheme 5

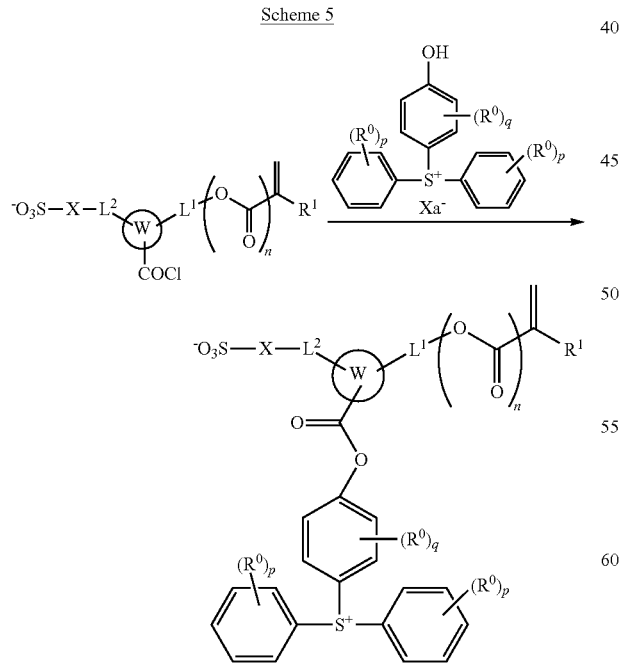

Herein $R^0$, $R^1$, $L^1$, $L^2$, X, W, n, p and q are as defined above, and Xa$^-$ is an anion.

While several synthesis methods have been described, they are merely exemplary and not intended to limit the invention thereto.

Another embodiment of the invention is a polymer or high-molecular-weight compound capable of generating a sulfonic acid in response to high-energy radiation or heat. The polymer is characterized by comprising recurring units having the general formula (3A), (3B) or (3C).

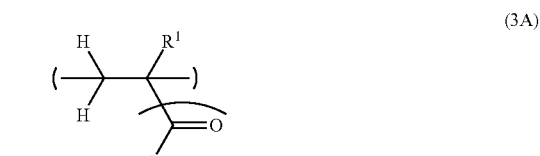

(3A)

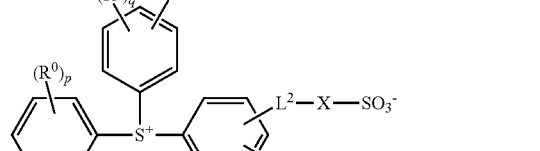

(3B)

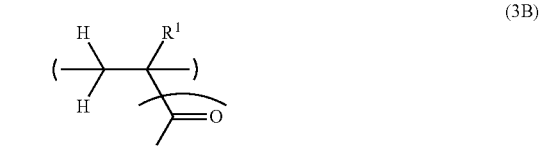

(3C)

Herein $R^0$, $R^1$, $L^1$, $L^2$, $L^3$, X, W, n, p, q and r are as defined and illustrated above.

Preferably the recurring units having formula (3A), (3B) or (3C) have the general formula (4A), (4B) or (4C).

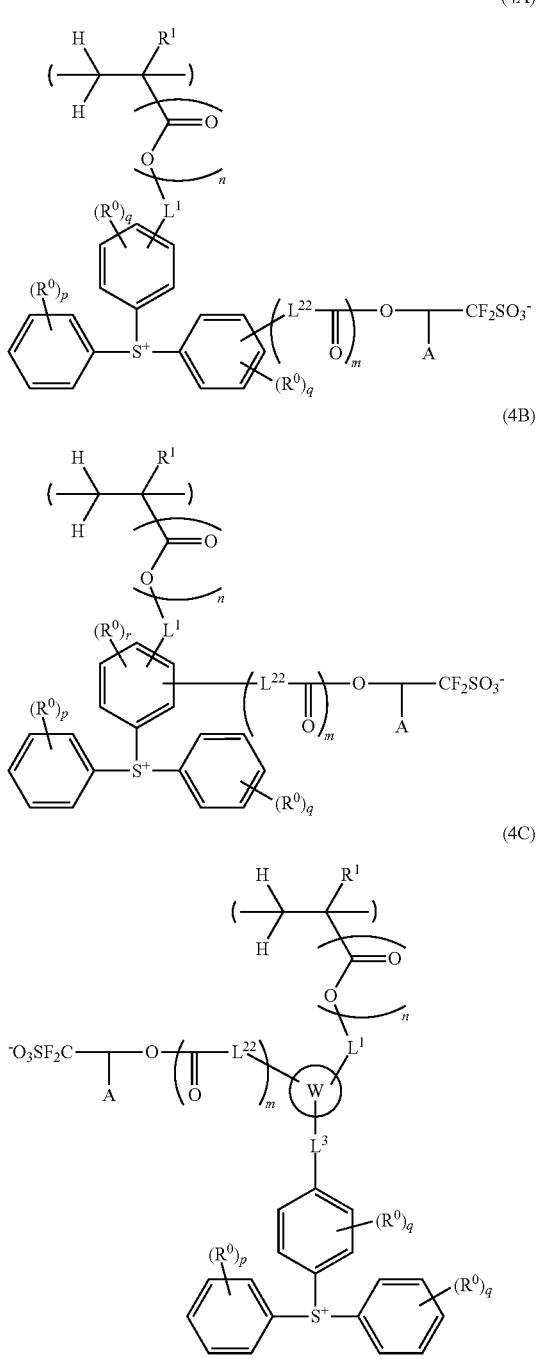

Herein $R^0$, $R^1$, $L^1$, $L^3$, $L^{22}$, W, n, p, q, r, m and A are as defined and illustrated above.

A resist composition comprising the polymer defined herein has the following advantages. Since the sulfonium salt serving as PAG is bound in the base resin, acid diffusion is suppressed, and resolution is thus improved. Since neither the anion nor the cation moiety is liberated from the polymer chain by virtue of the binding structure, the leaching of any moiety in water during immersion lithography is minimized, indicating that the resist composition is best suited for the ArF immersion lithography. Since the cation and anion moieties are within a common molecule and bound in the polymer chain, the sulfonium salt of the invention does not become a volatile compound even after acid generation, resulting in a minimal amount of outgassing. While a reduction of outgassing is one of the pending problems that the EB and EUV lithography should overcome, the resist composition is quite useful in such lithography because of a minimized possibility of contaminating the exposure tool.

On the other hand, JP-A 2012-048075 describes a radiation-sensitive resin composition comprising a polymer having cationic recurring units and anionic recurring units. Since PAG units, cation and anion units are both incorporated in the polymer chain, a reduction of outgassing is expected for this composition. However, the polymer is difficult to control its molecular weight during polymerization because of a possibility that crosslink-like reaction takes place during polymerization as the cation and anion moieties can bond with another polymer chain during polymerization. As a result, a resist composition using this polymer leaves concerns about defect formation, a failure in the desired performance, and a lack of reproducibility.

In contrast, the polymer of the invention does not undergo crosslinking reaction as above because of one polymerizable substituent to one sulfonium salt unit relationship and is easy to tailor to the desired molecular weight. The polymer is thus reproducible.

In addition to the recurring units having formula (3A), (3B), (3C), (4A), (4B) or (4C), the polymer may further comprise recurring units having the general formula (5).

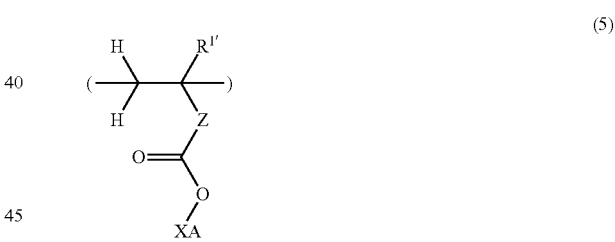

Herein $R^{1'}$ is hydrogen, methyl or trifluoromethyl. Z is a single bond, phenylene group, naphthylene group or (backbone)-C(=O)—O—Z'—, wherein Z' is a straight, branched or cyclic $C_1$-$C_{10}$ alkylene group which may contain a hydroxyl radical, ether bond, ester bond or lactone ring, or Z' is a phenylene or naphthylene group. XA is an acid labile group.

Examples of the structure having formula (5) wherein Z is a variant are shown below.

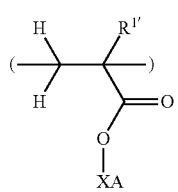

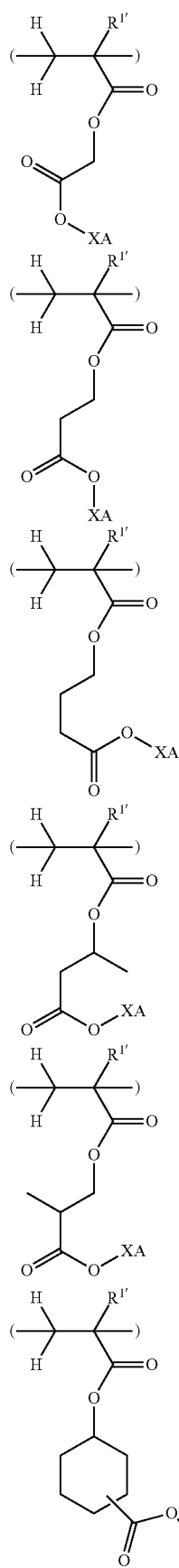
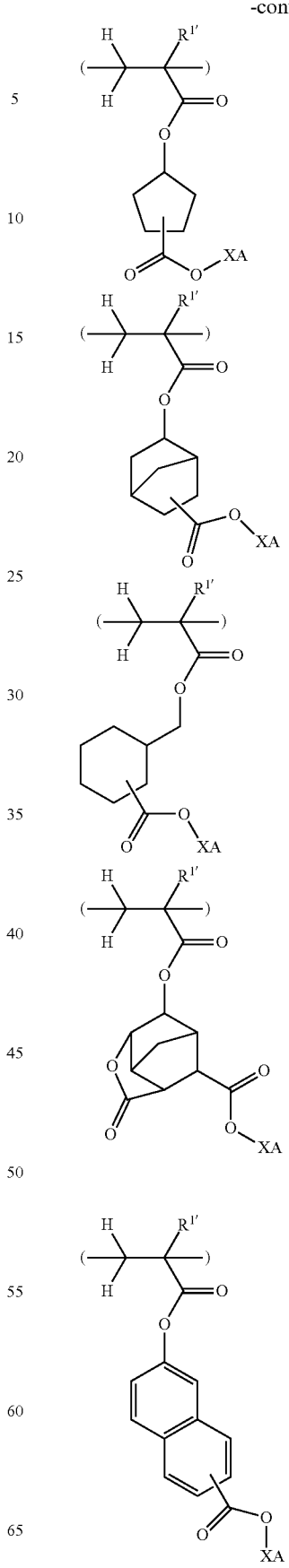

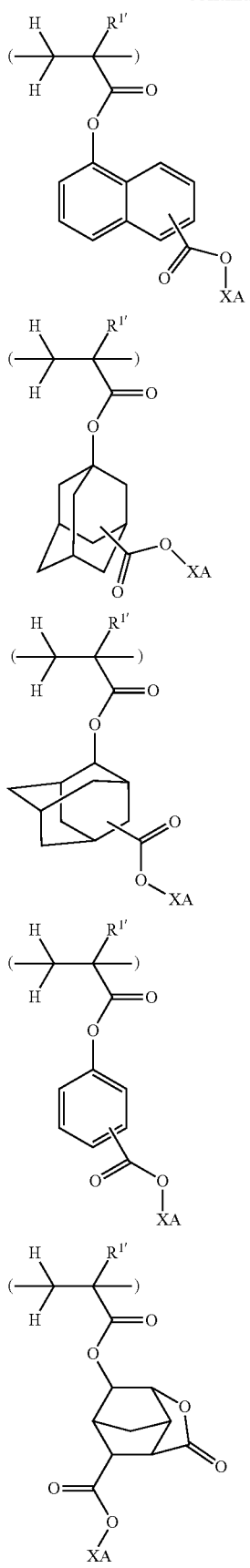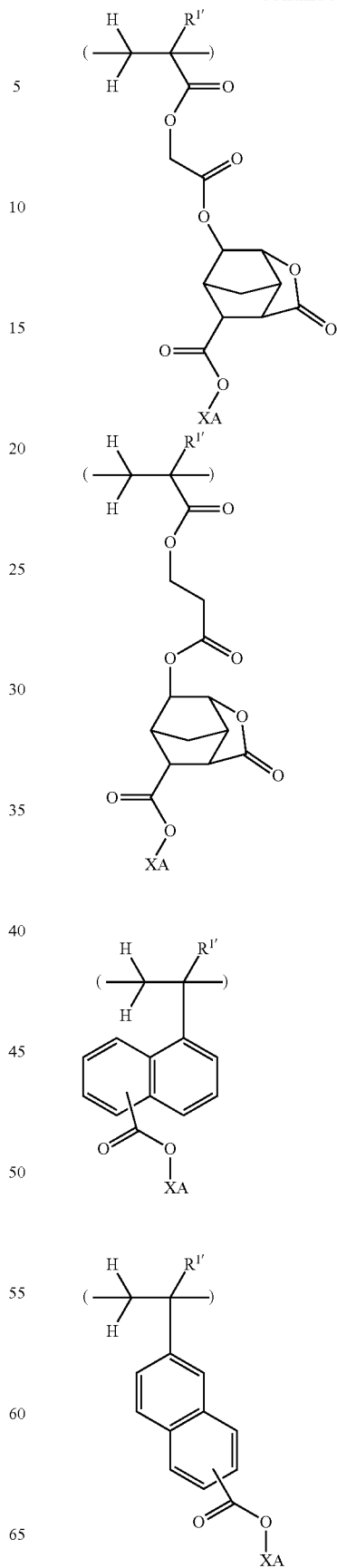

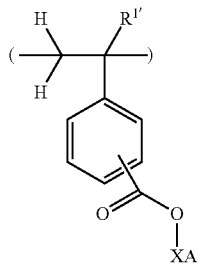

Under the action of acid, a polymer comprising recurring units of formula (5) is decomposed to generate carboxylic acid, turning to be an alkali soluble polymer. The acid labile group represented by XA may be selected from a variety of such groups. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

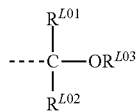 (L1)

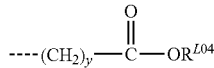 (L2)

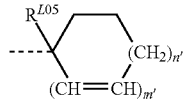 (L3)

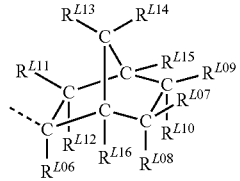 (L4)

In these formulae, the broken line denotes a valence bond.

In formula (L1), $R^{L01}$ and $R^{L02}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like, or in which an oxygen atom intervenes between carbon atoms. Exemplary straight, branched or cyclic alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. Illustrative examples of the substituted alkyl groups are shown below.

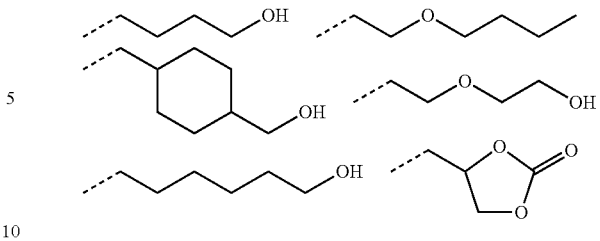

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl. Letter m' is equal to 0 or 1, n' is equal to 0, 1, 2 or 3, and 2 m'+n' is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

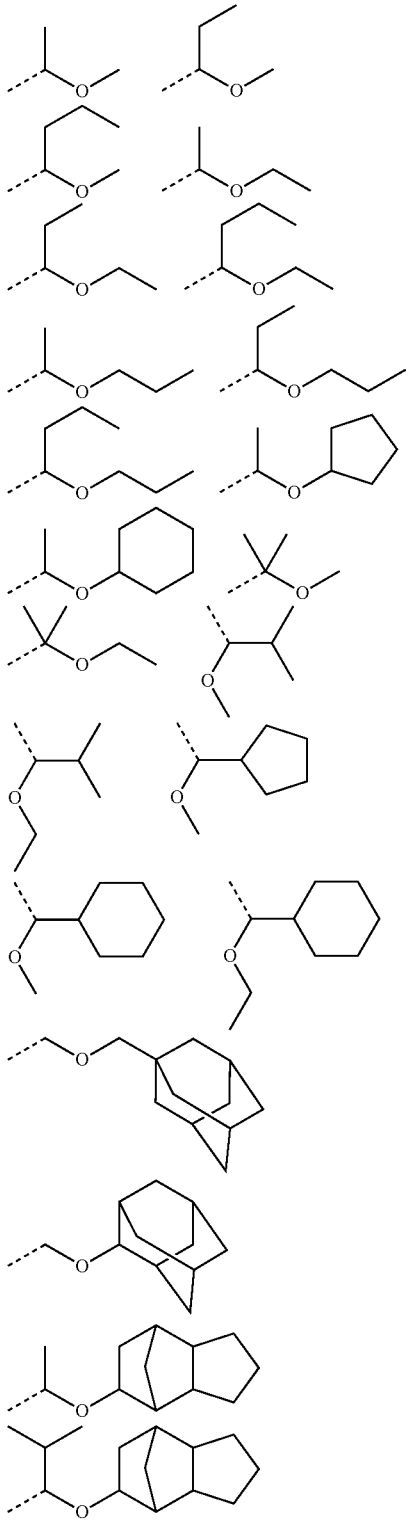

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethyl cyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

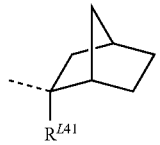

(L4-1)

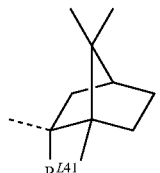

(L4-2)

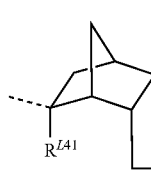

(L4-3)

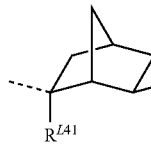

(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

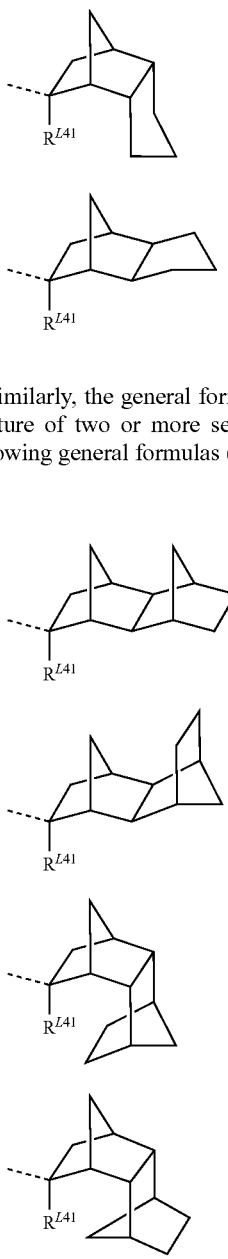

(L4-3-1)

(L4-3-2)

Similarly, the general formula (L4-4) represents one or a mixture of two or more selected from groups having the following general formulas (L4-4-1) to (L4-4-4).

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

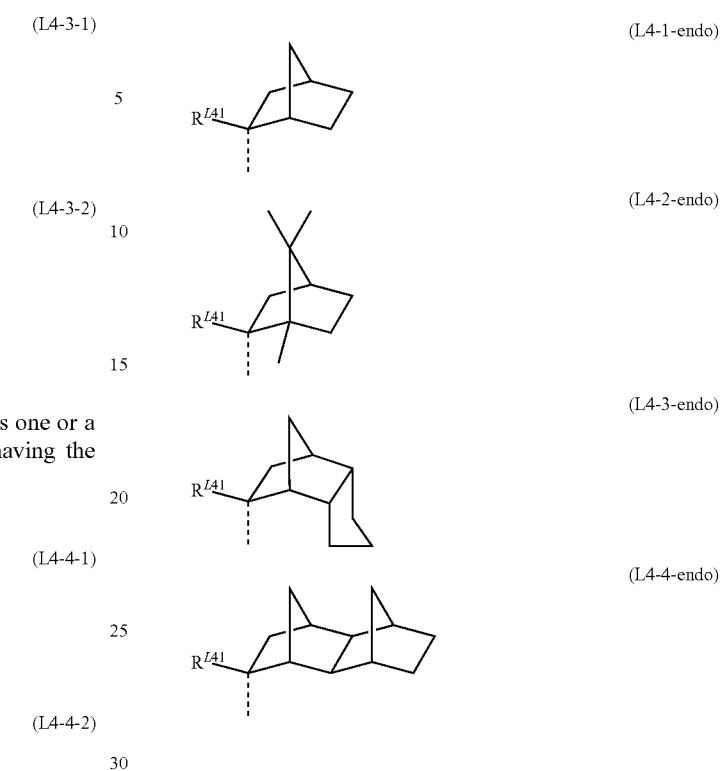

Illustrative examples of the acid labile group of formula (L4) are given below.

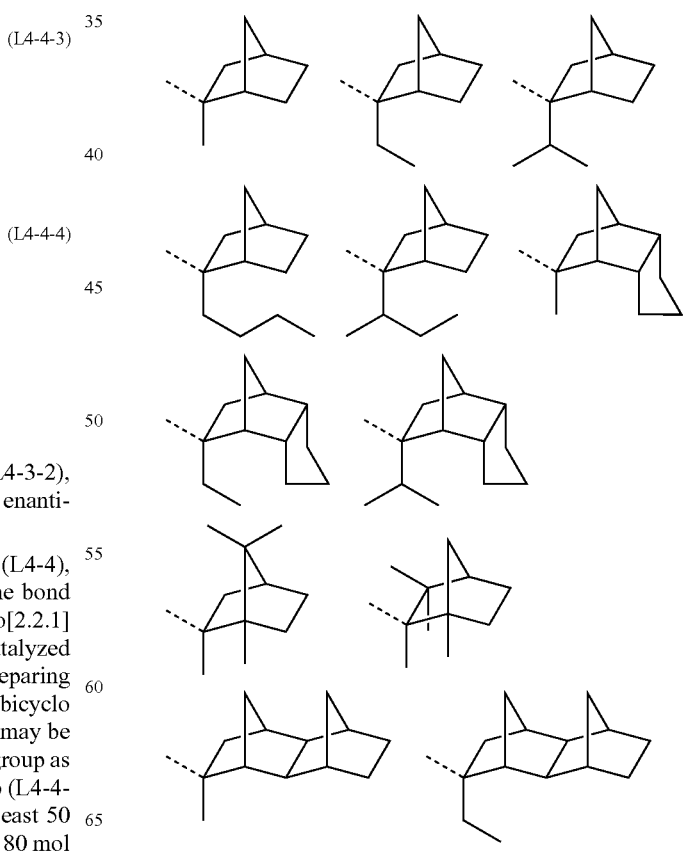

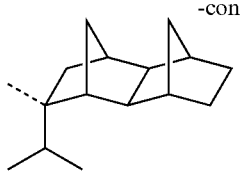
Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{LO4}$.
Illustrative examples of the recurring units of formula (5) are given below, but not limited thereto.
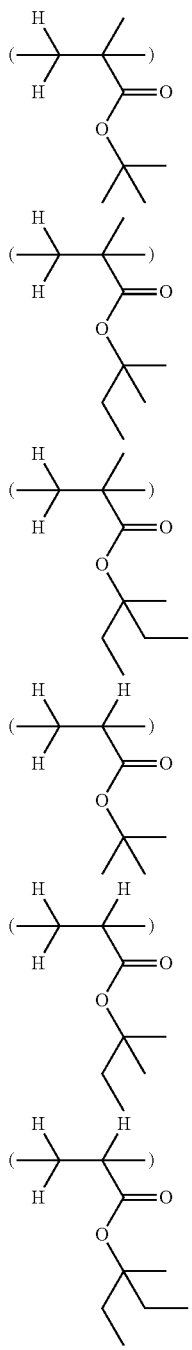
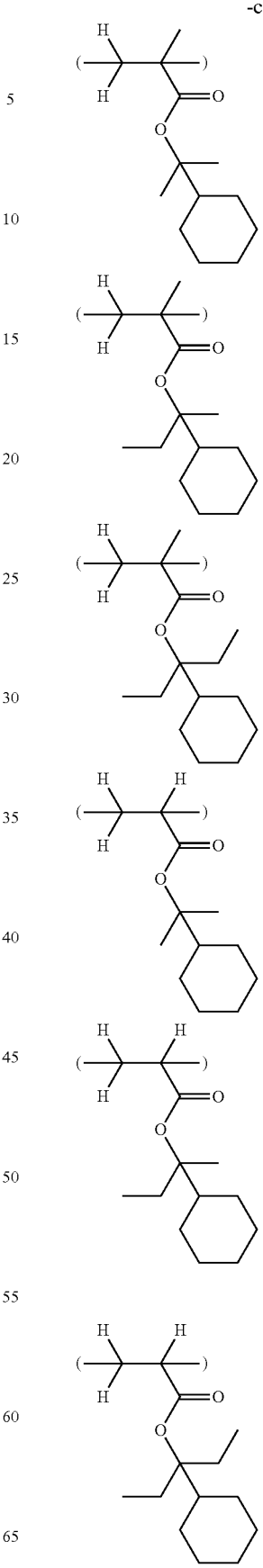

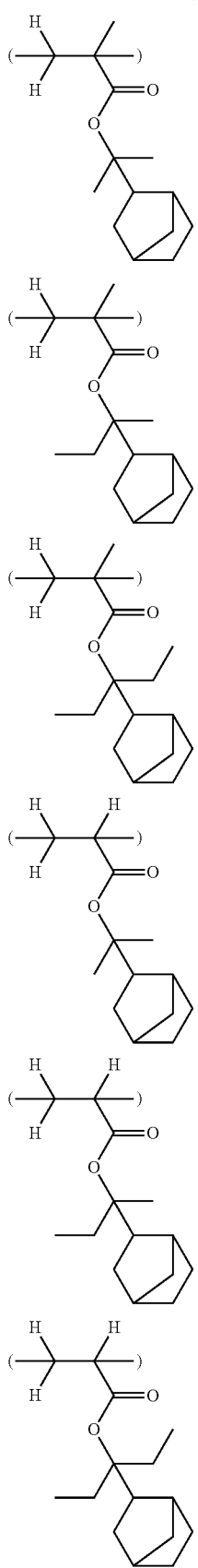
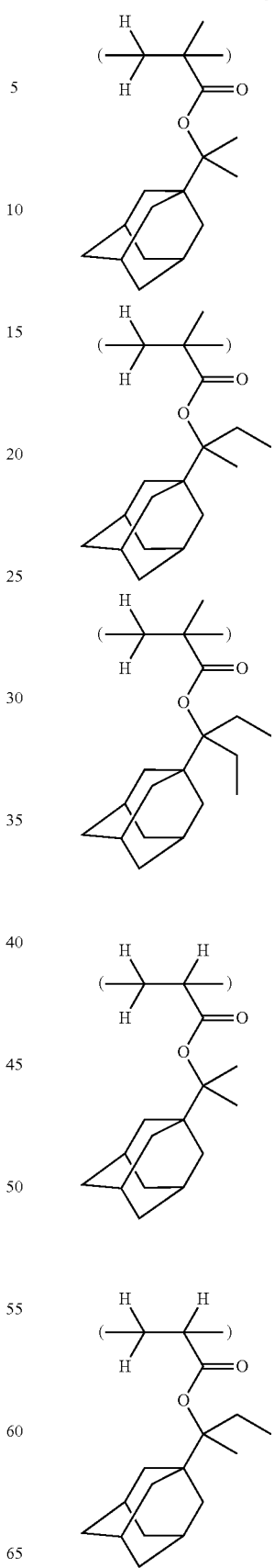

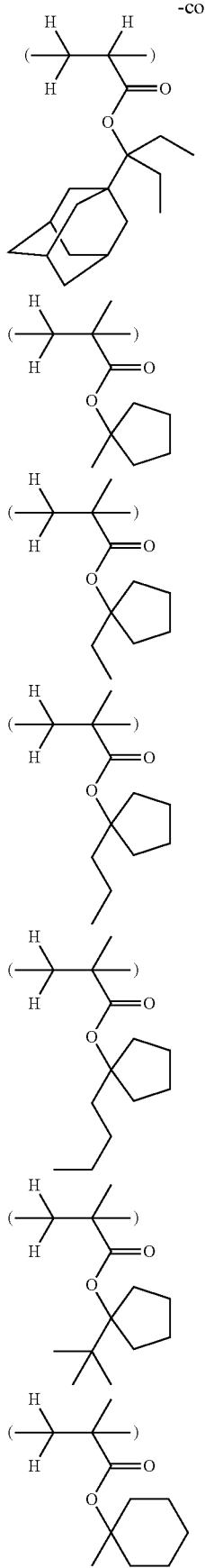
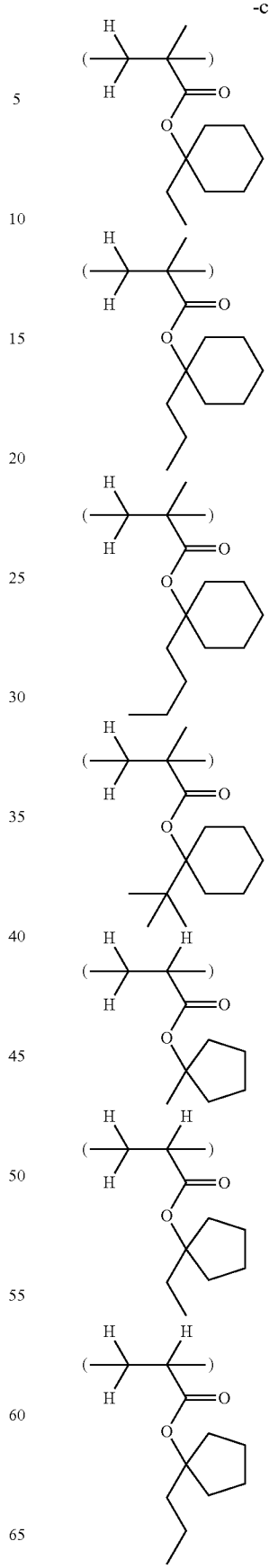

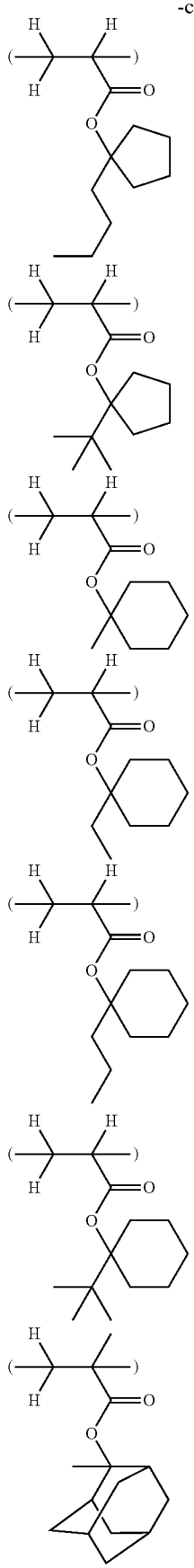
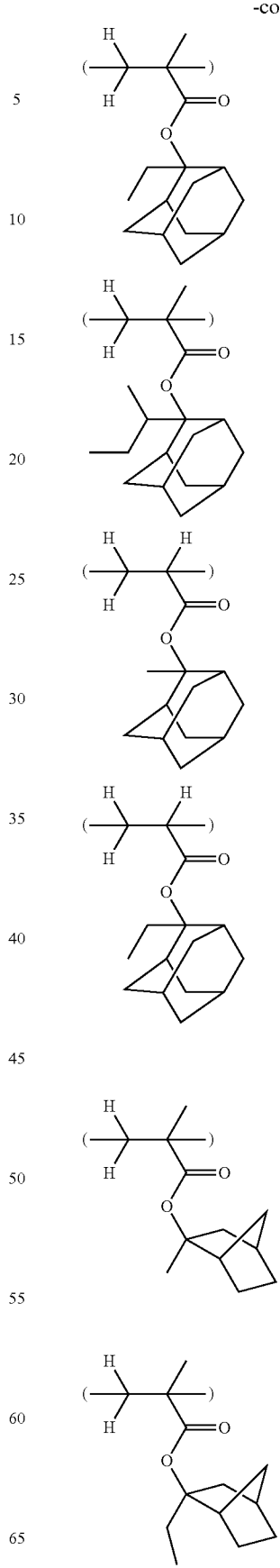

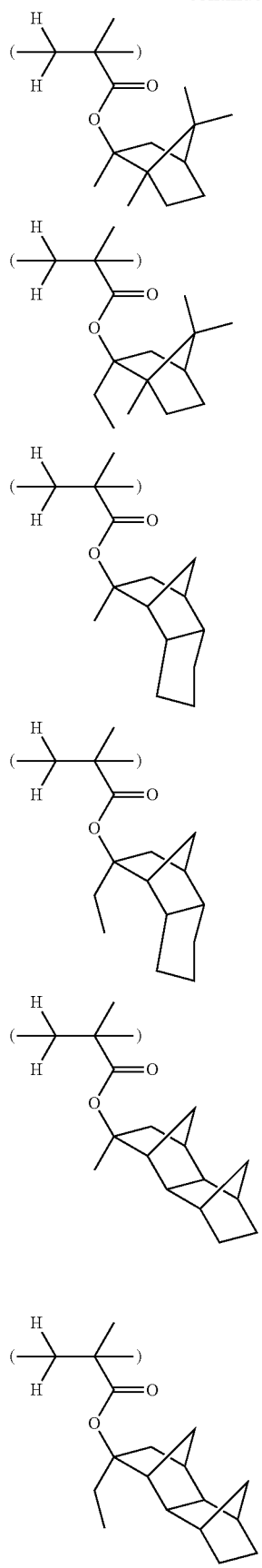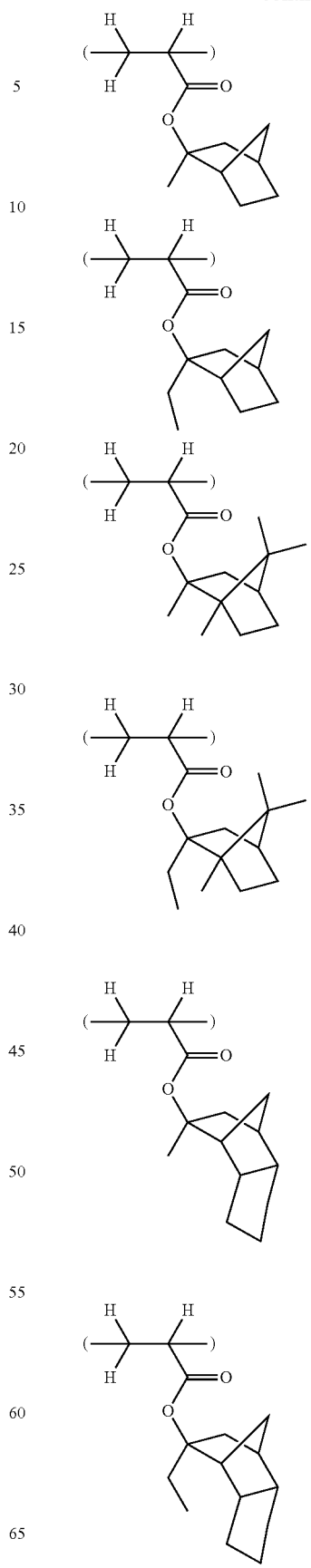

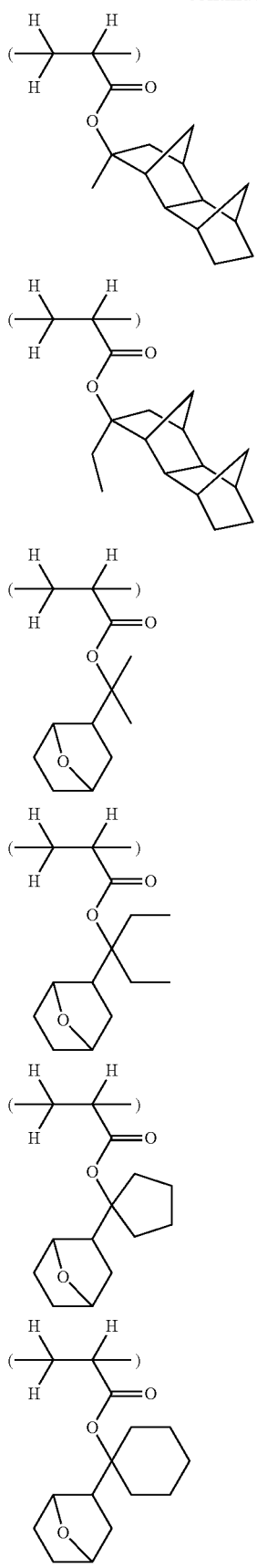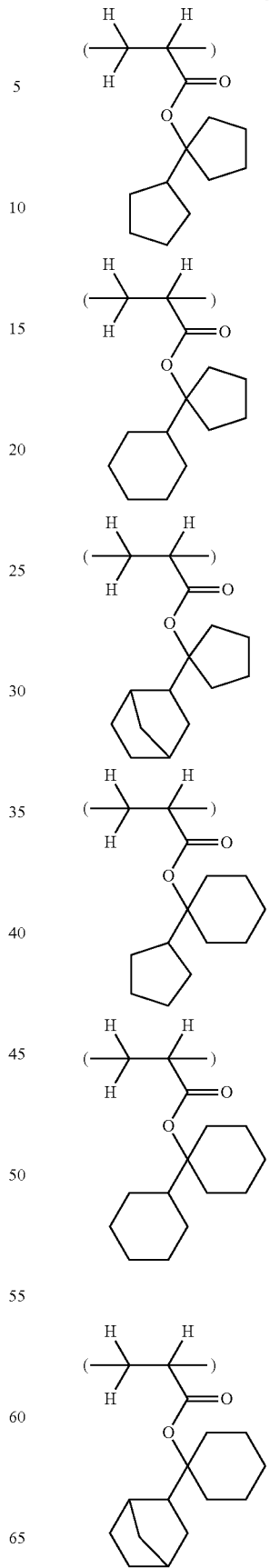

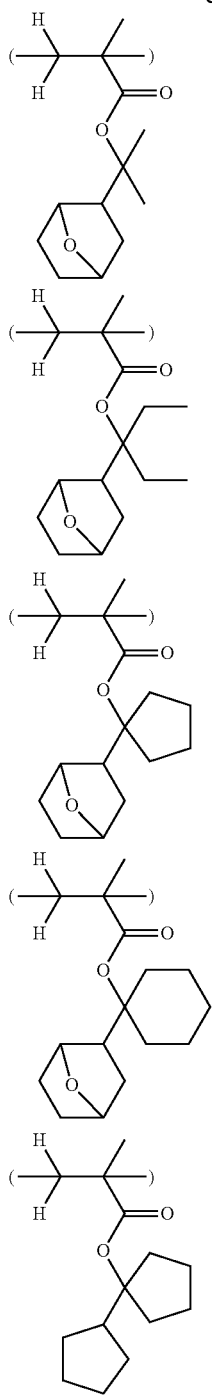
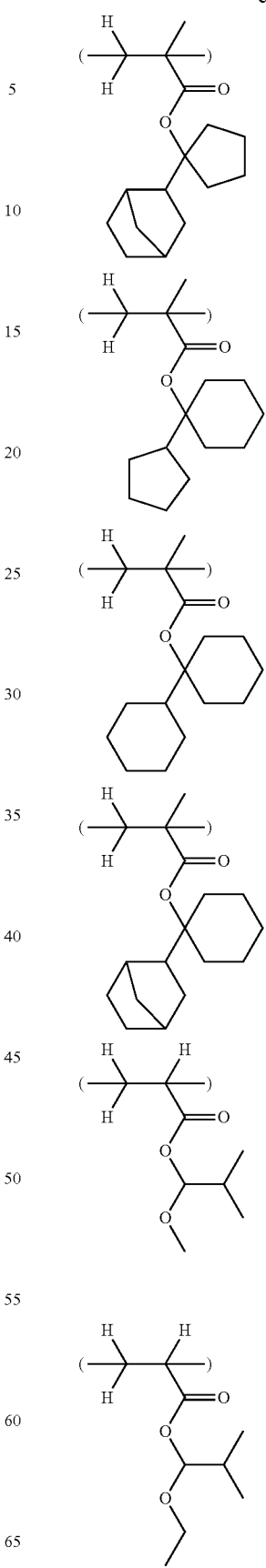

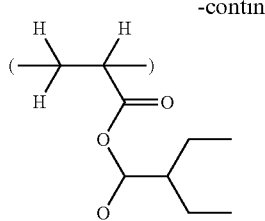
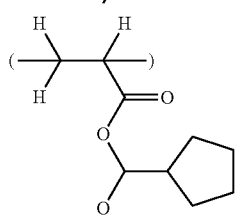
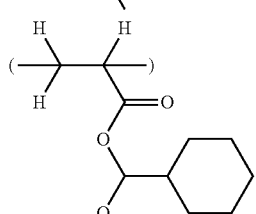
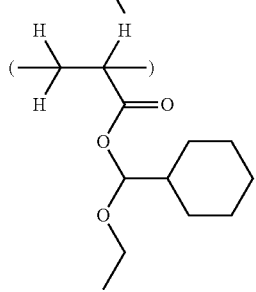
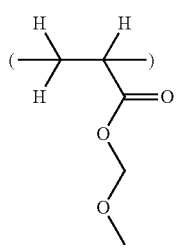
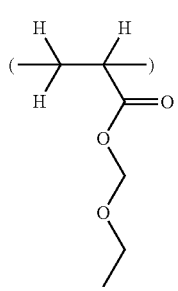
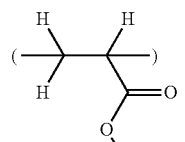
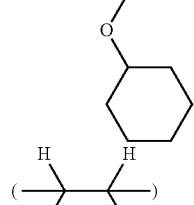
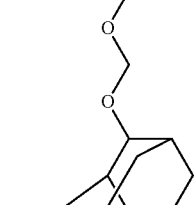
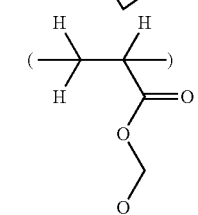
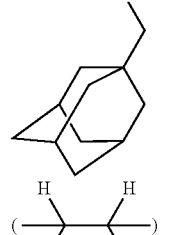
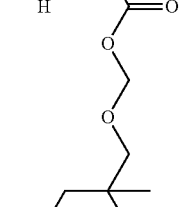
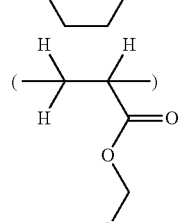
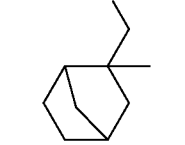

51
-continued
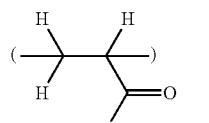
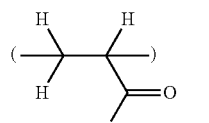
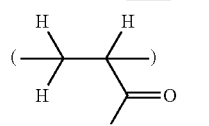
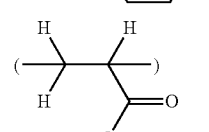
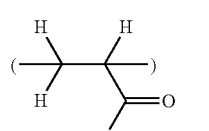
52
-continued
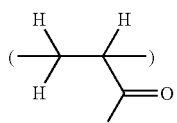
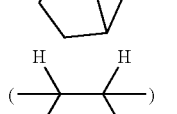
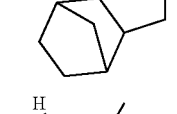
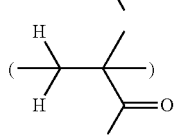
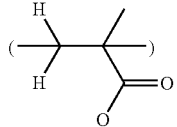
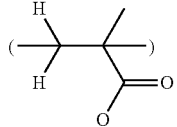
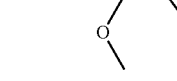

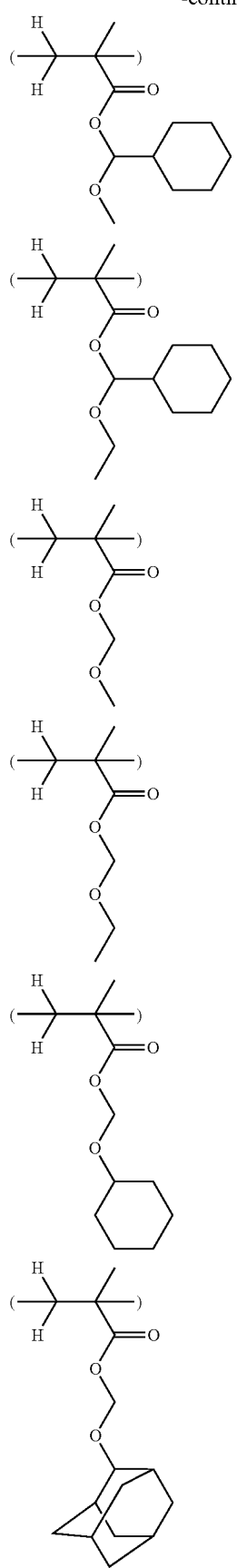
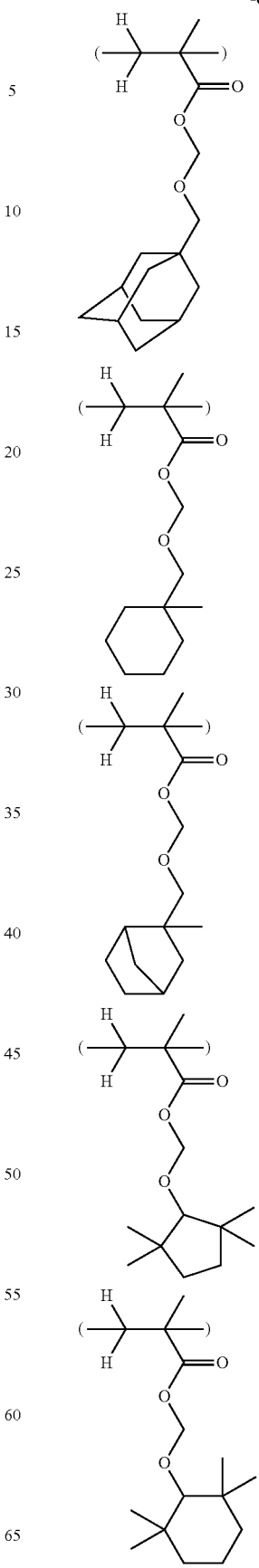

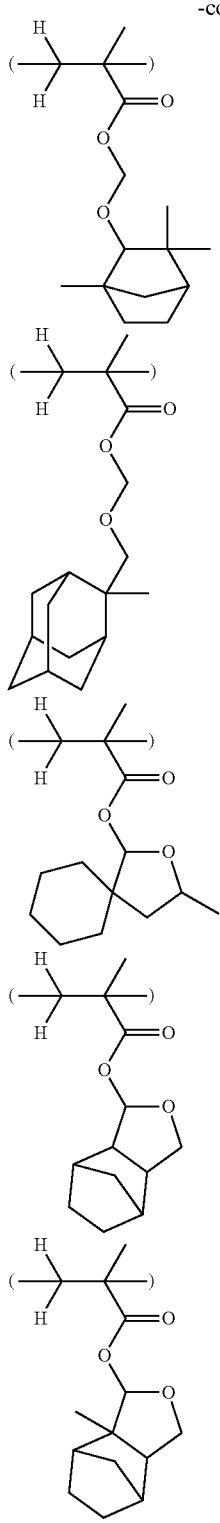

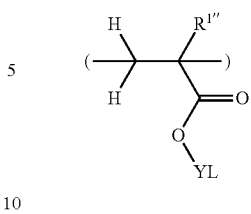

(6)

Herein $R^{1''}$ is hydrogen, methyl or trifluoromethyl. YL is a polar group having one or more structures selected from the group consisting of hydroxyl, cyano, carbonyl, carboxyl, ether bond, ester bond, sulfonic acid ester link, carbonate, lactone ring, sultone ring, and carboxylic anhydride.

Illustrative, non-limiting examples of the recurring units having formula (6) are shown below.

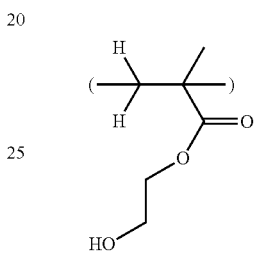

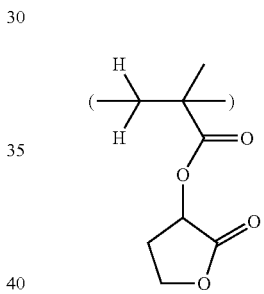

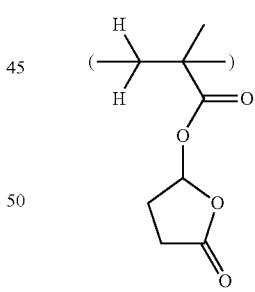

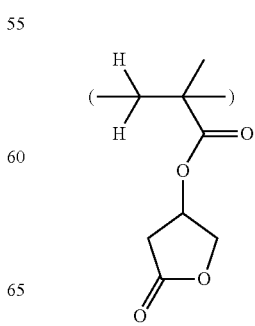

While the foregoing examples correspond to those units wherein Z is a single bond, Z which is other than a single bond may be combined with similar acid labile groups. Examples of units wherein Z is other than a single bond are substantially the same as illustrated above.

Besides the acid labile group-containing units having formula (5), the polymer may further comprise additional units, typically recurring units having the general formula (6).

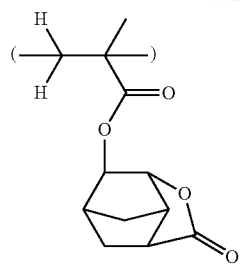
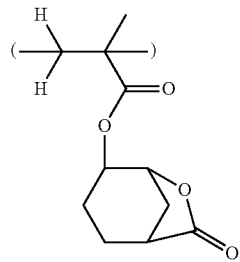
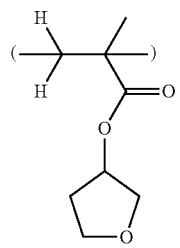
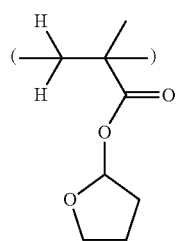
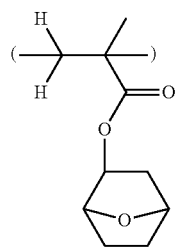
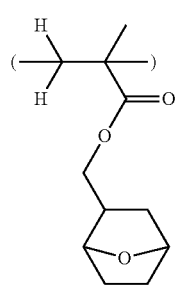
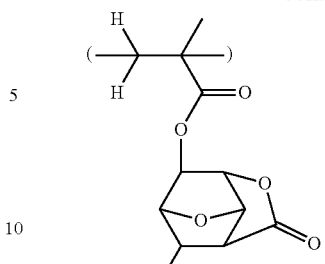
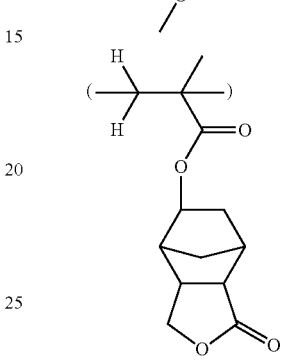
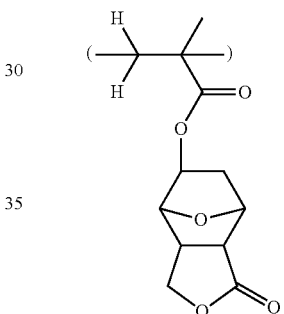
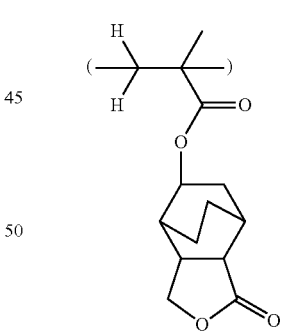
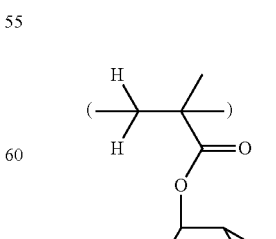

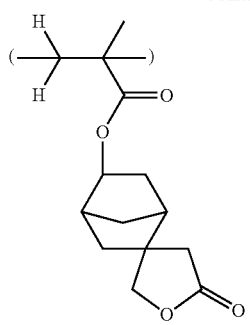
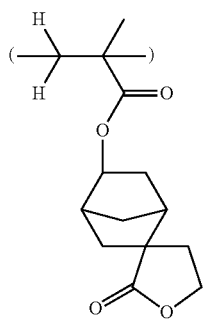
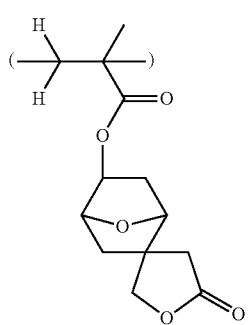
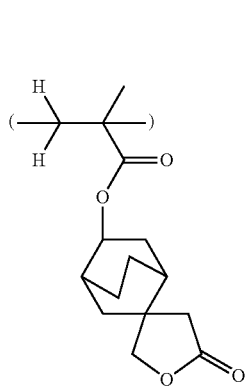
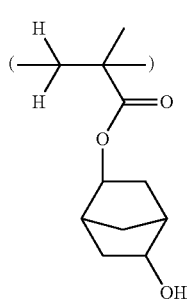
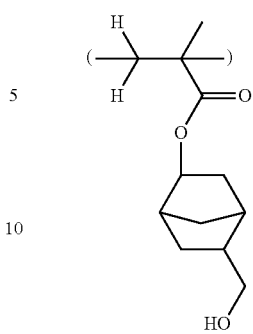
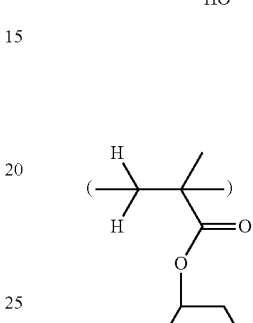
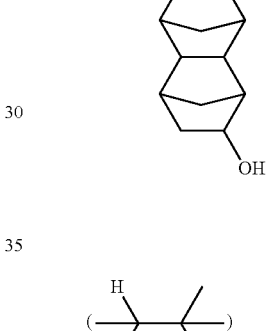
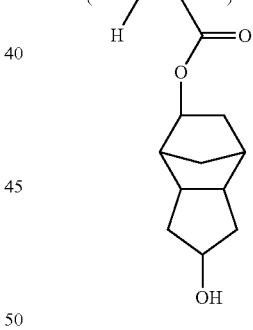
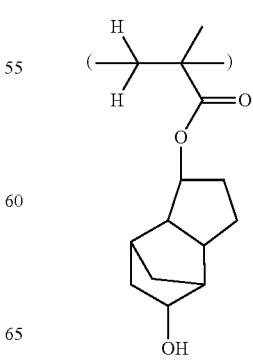

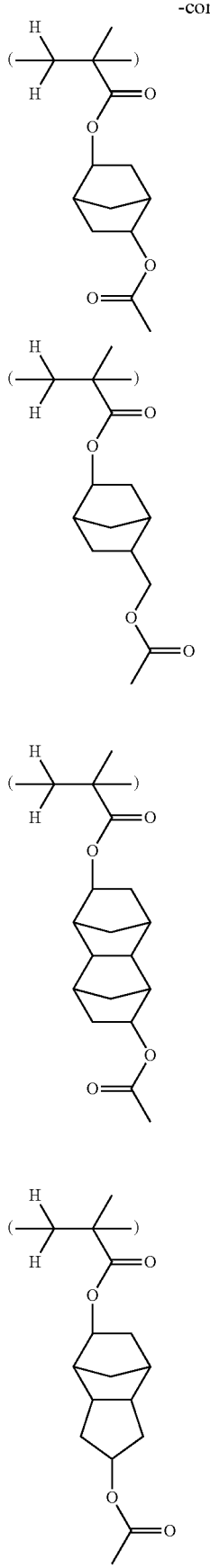
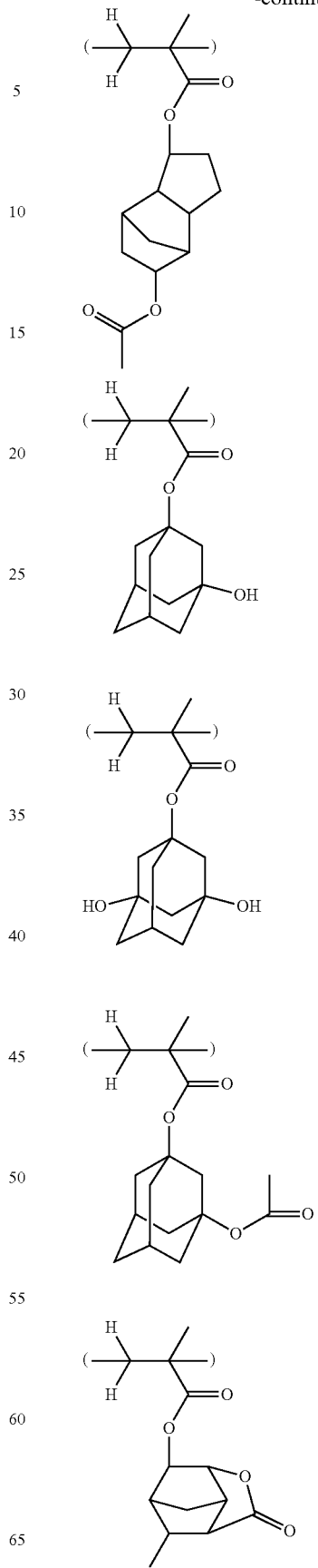

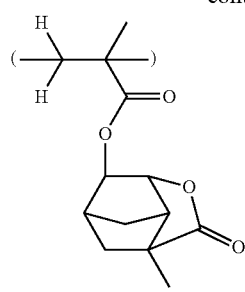
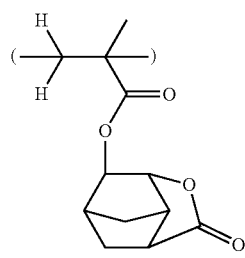
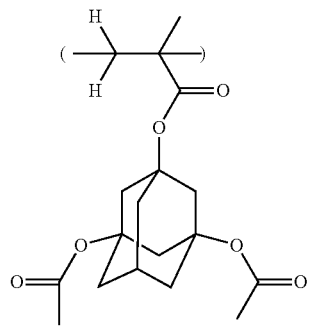
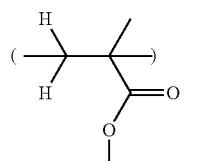
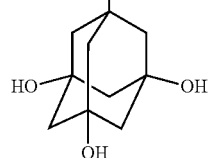
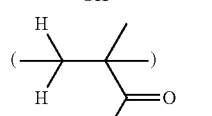
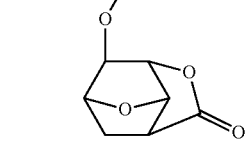
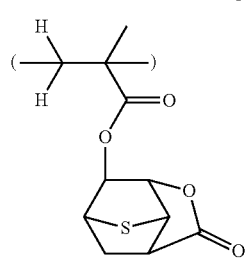
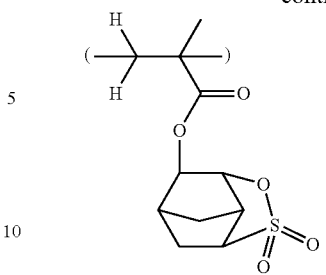
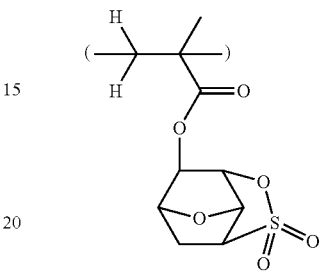
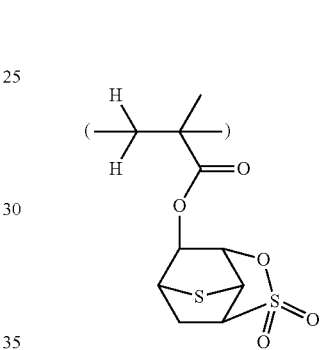
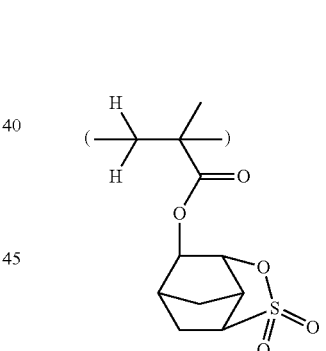
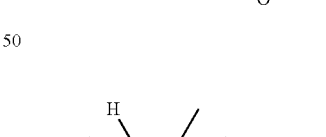
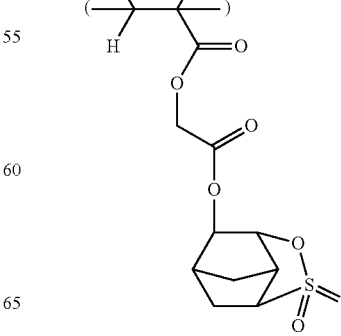

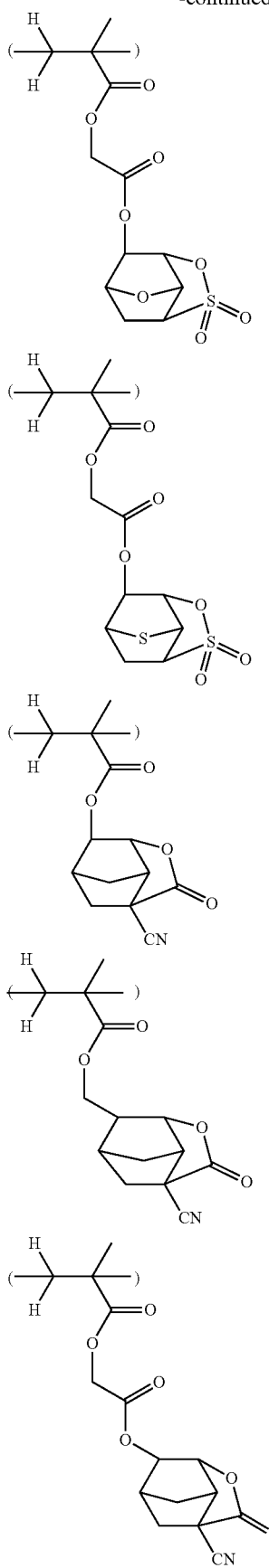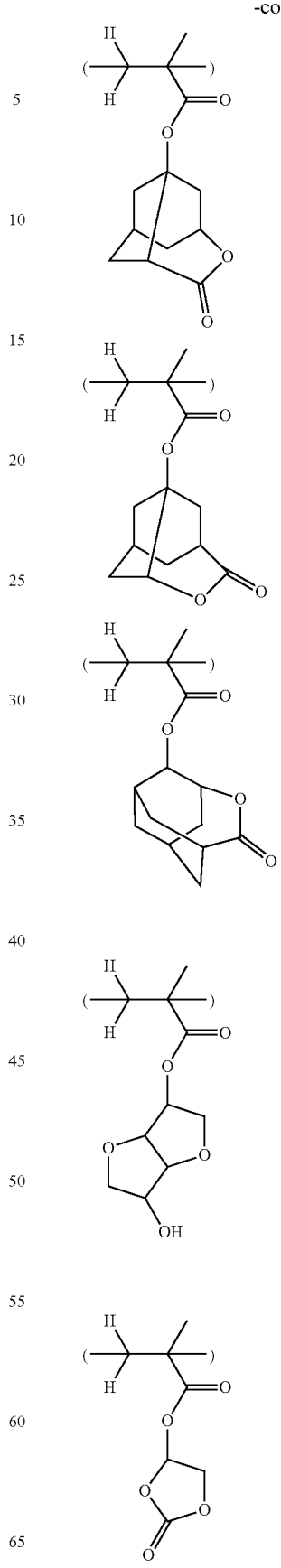

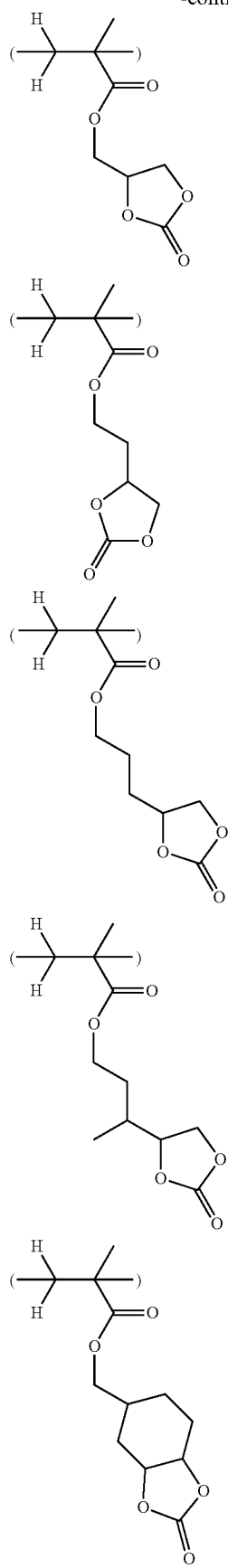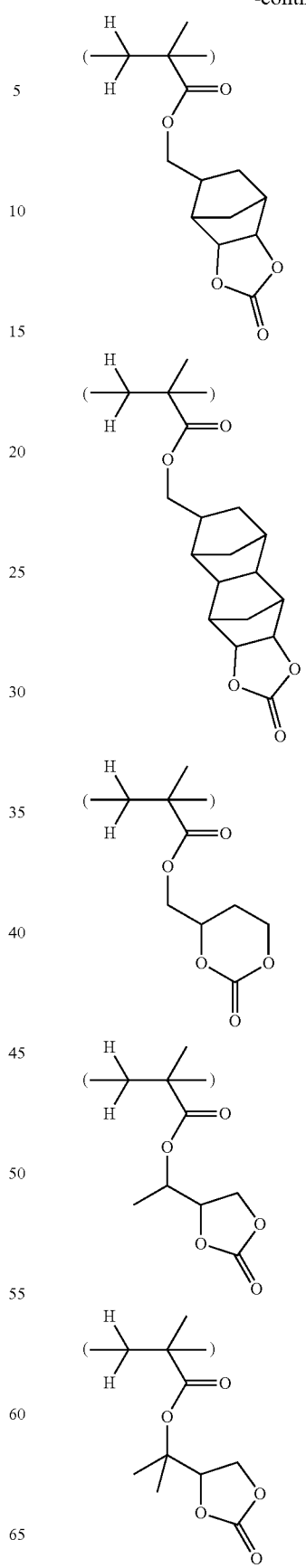

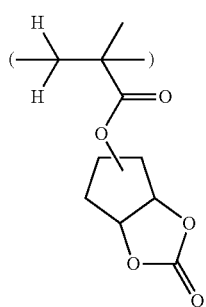
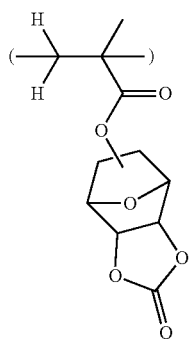
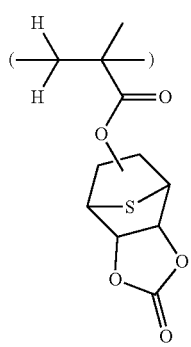
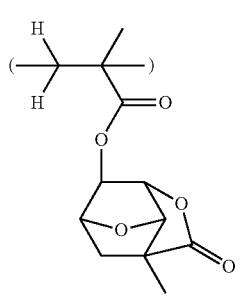
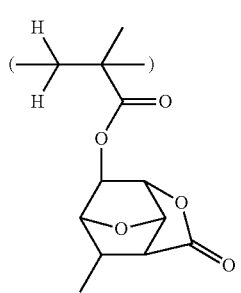
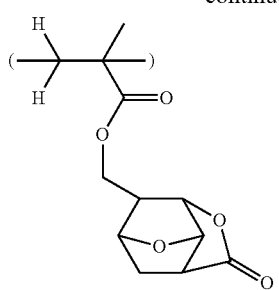
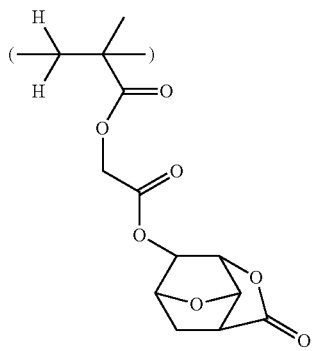
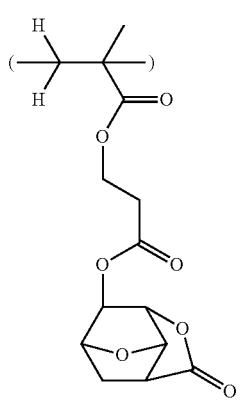
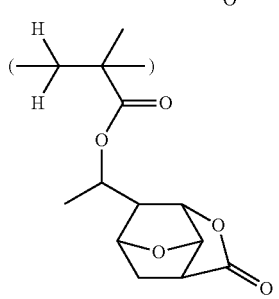
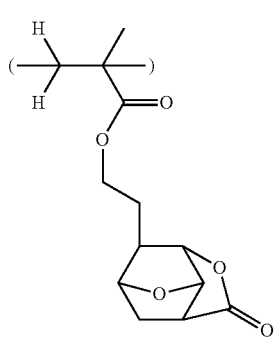

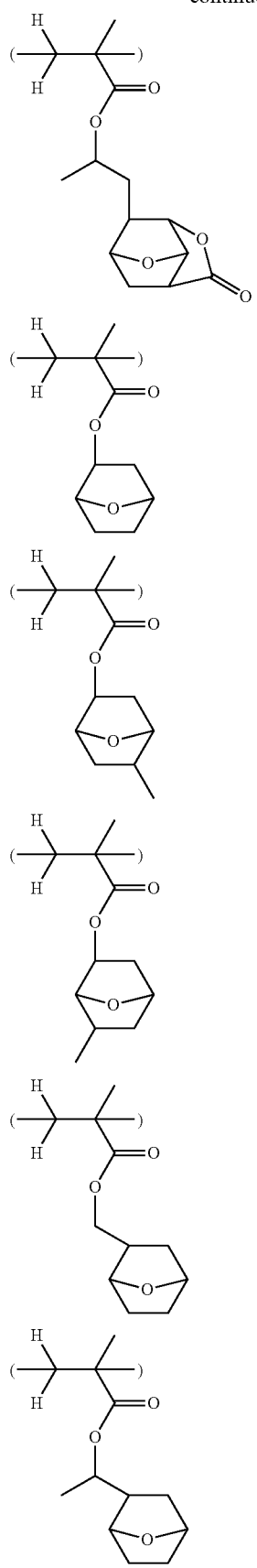
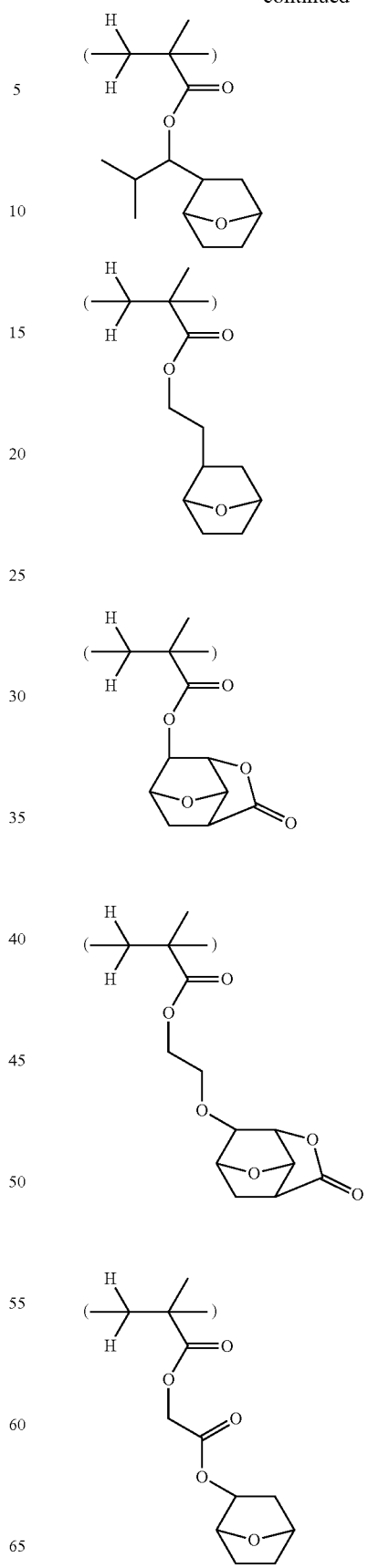

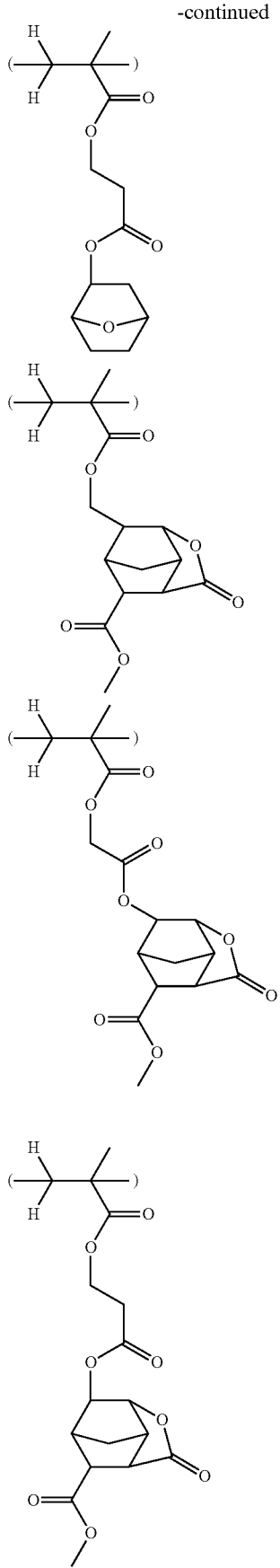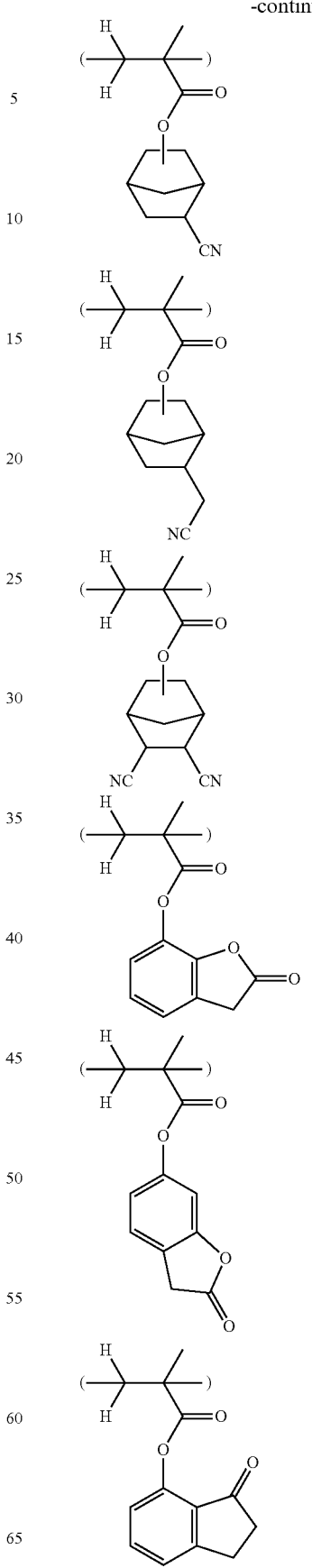

75
-continued
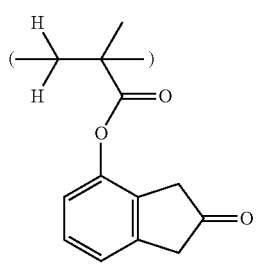
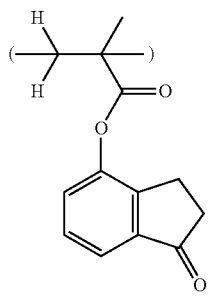
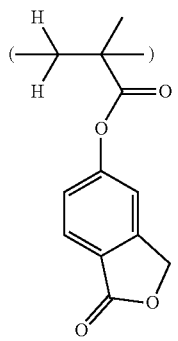
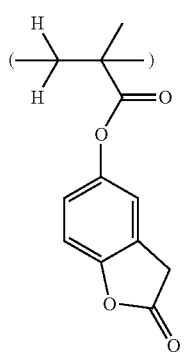
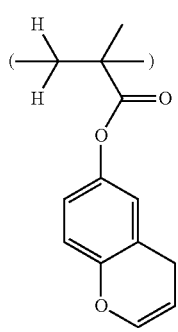
76
-continued
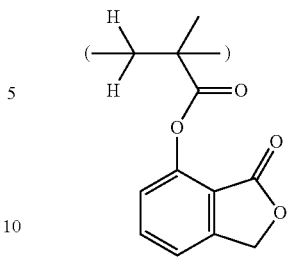
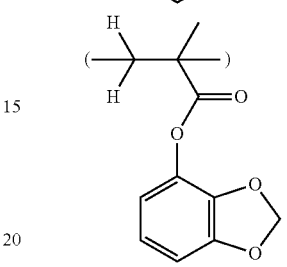
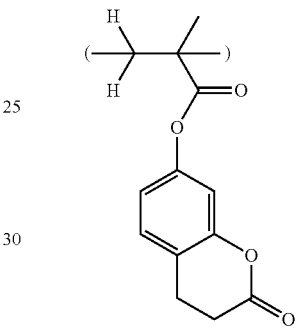
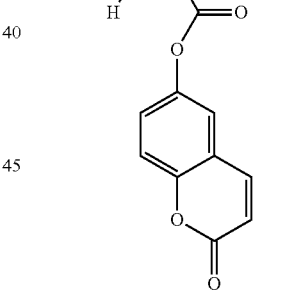
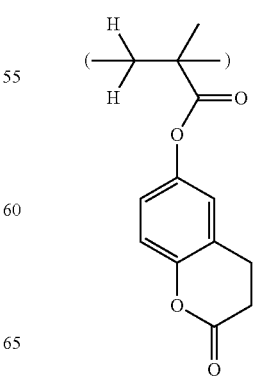

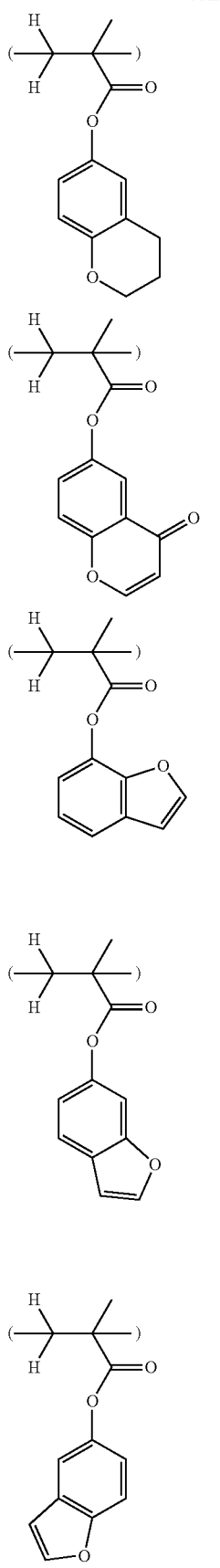
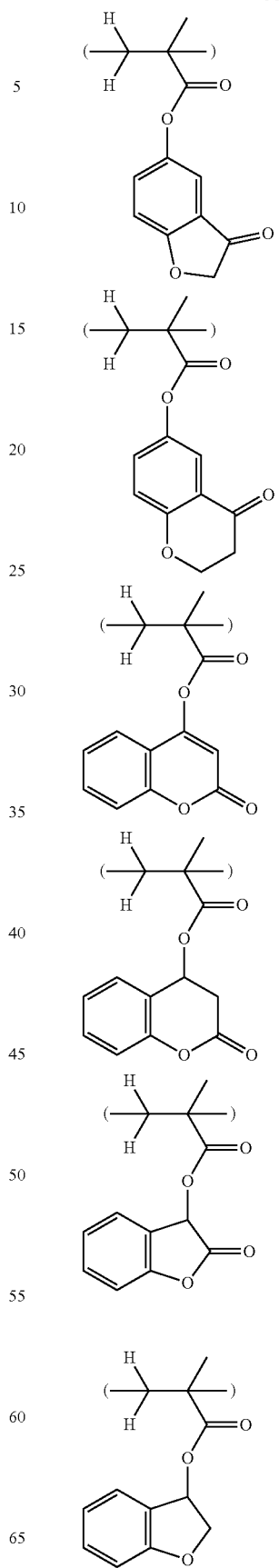

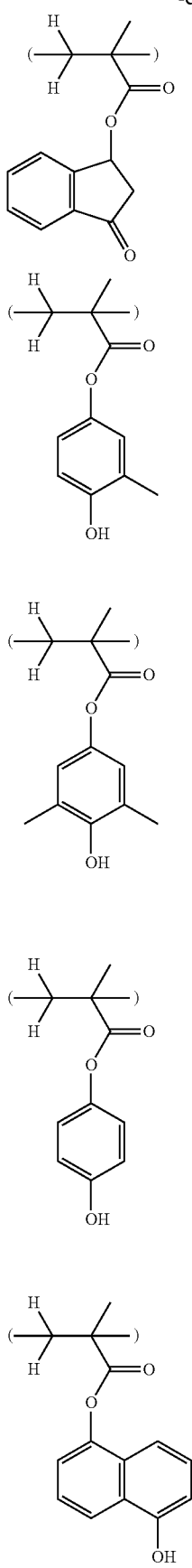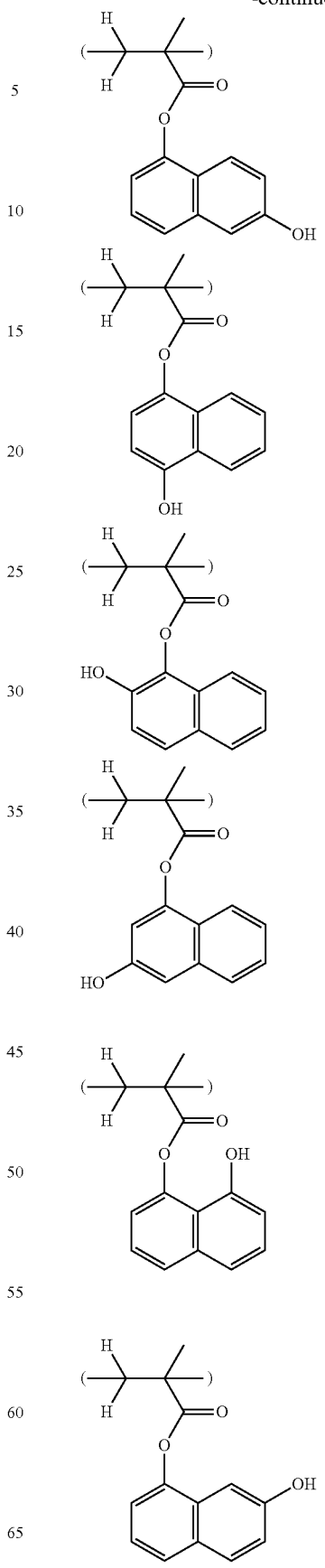

81
-continued
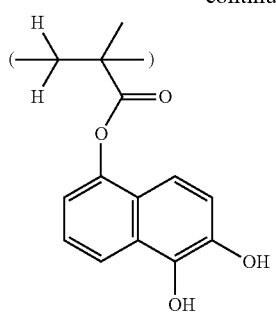
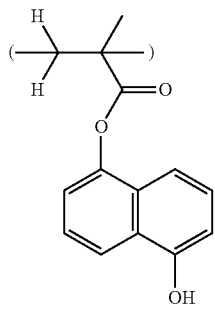
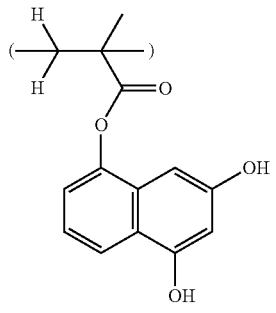
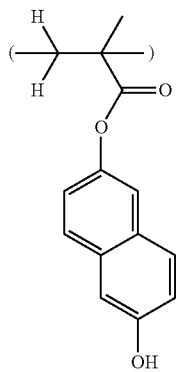
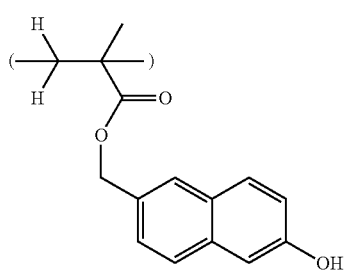
82
-continued
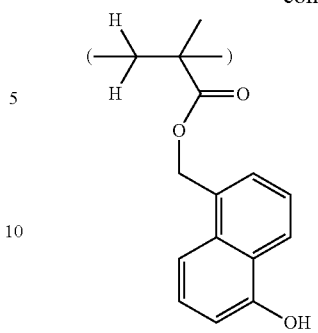
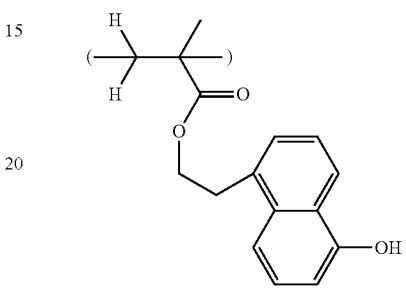
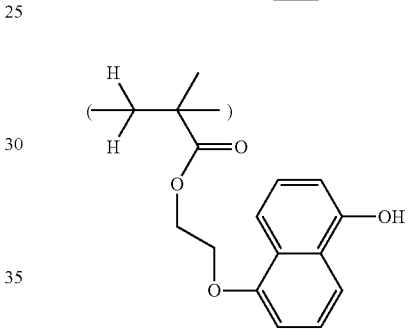
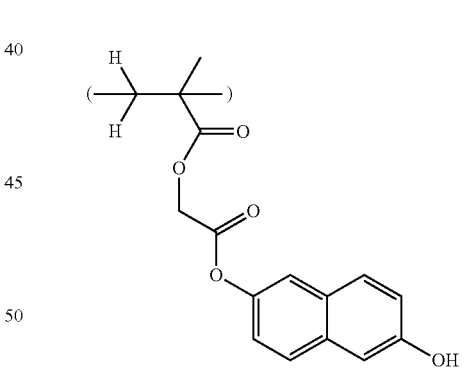
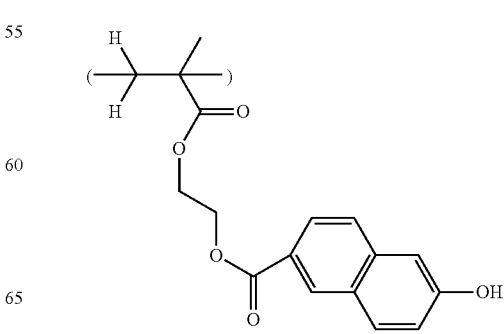

-continued
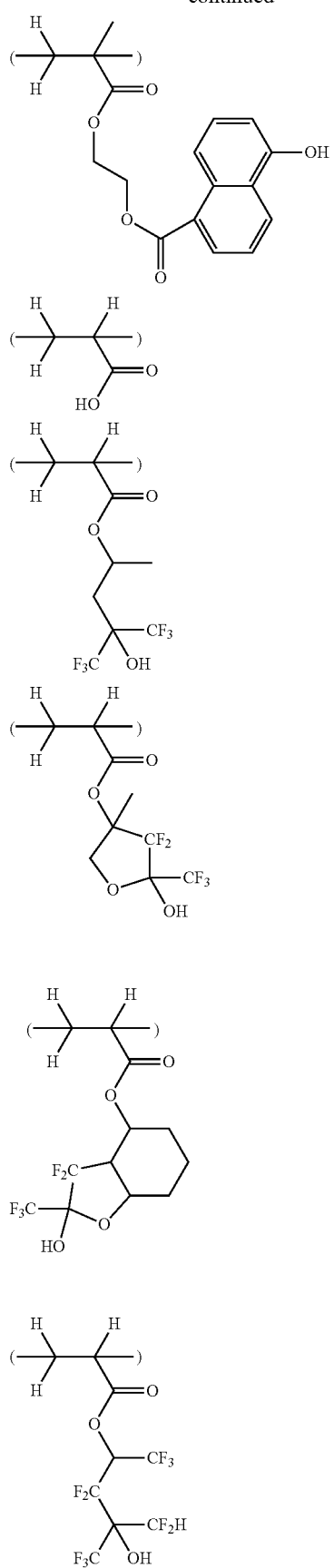
-continued
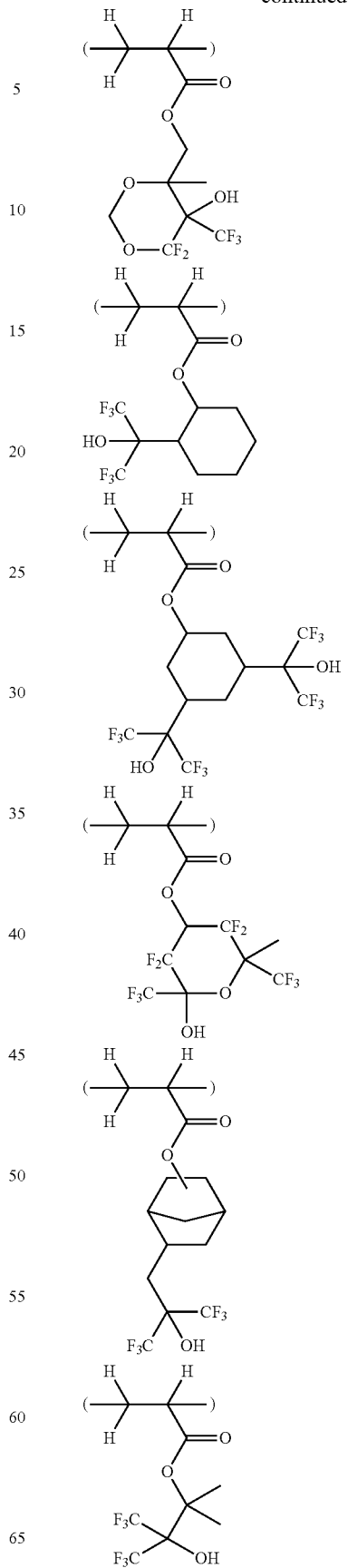

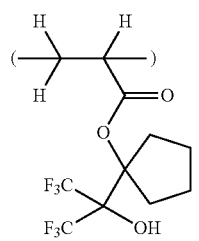
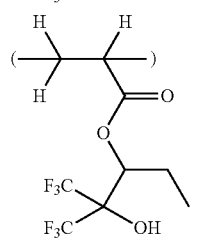
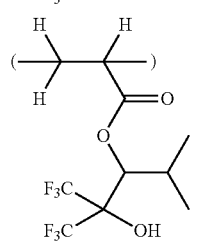
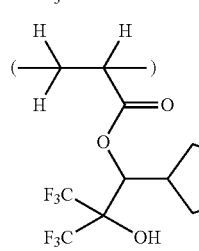
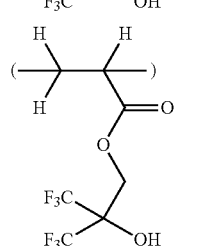
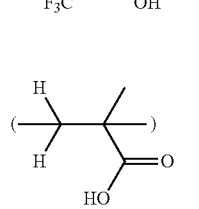
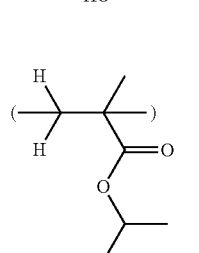
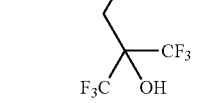
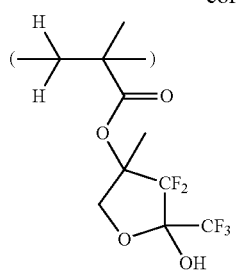
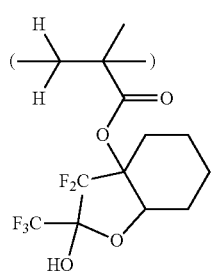
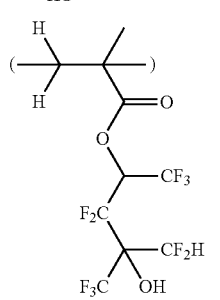
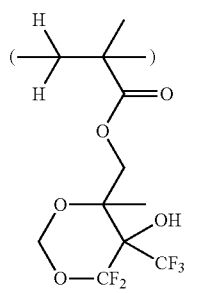
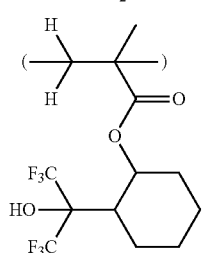
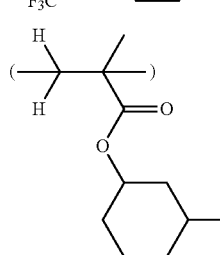
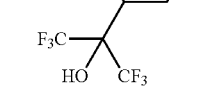

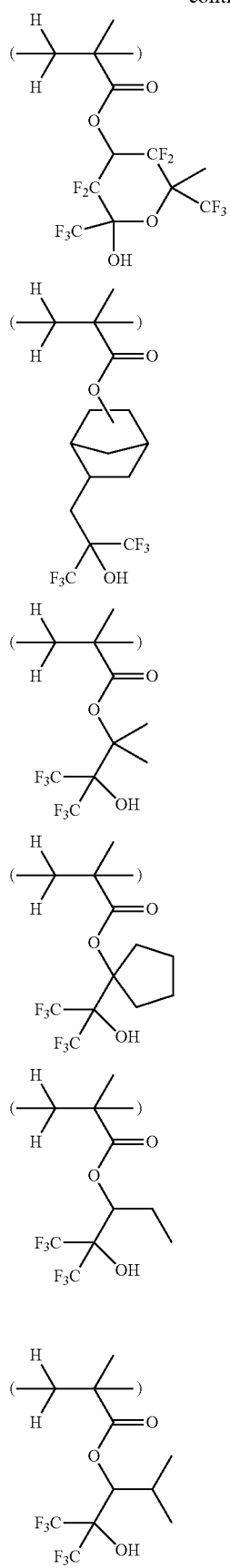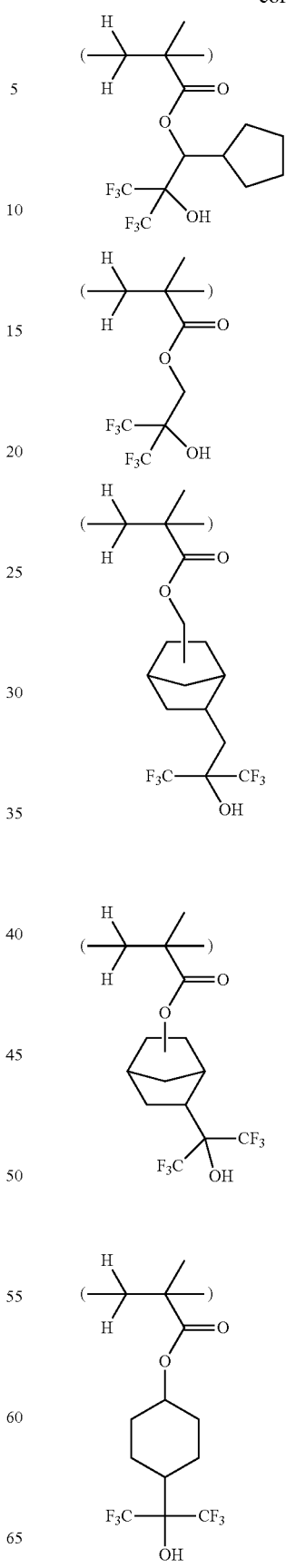

89
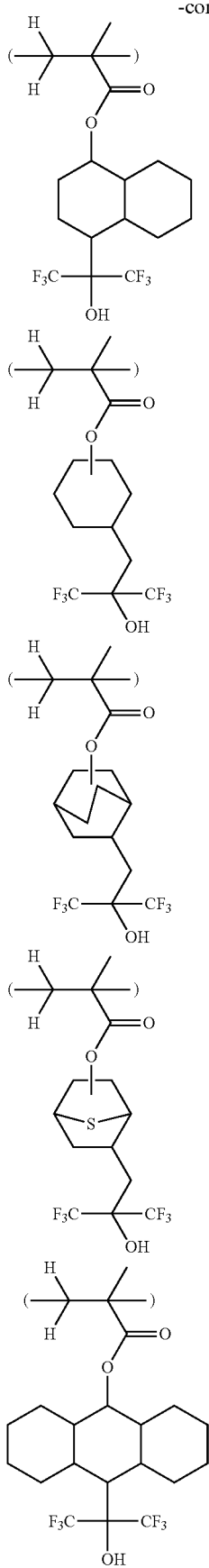
90
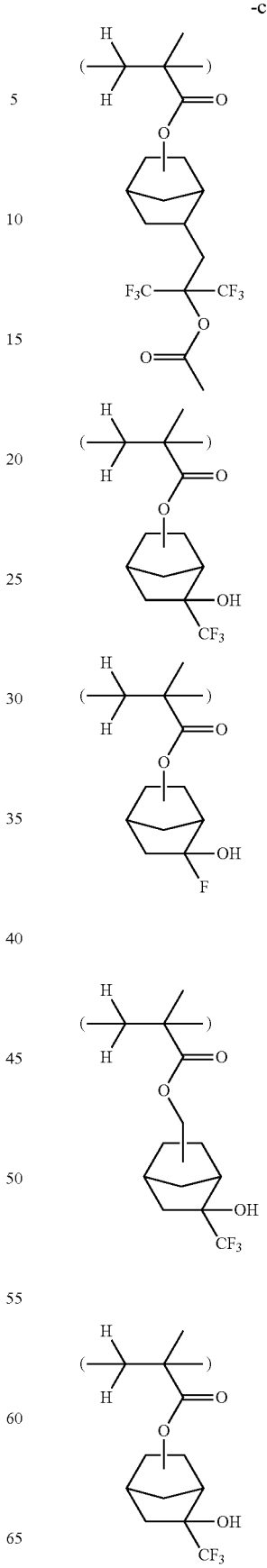

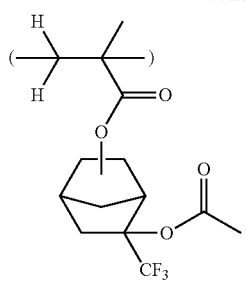
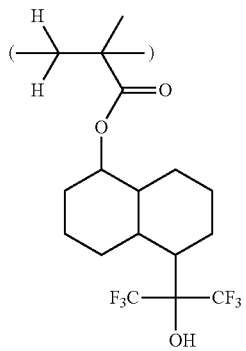
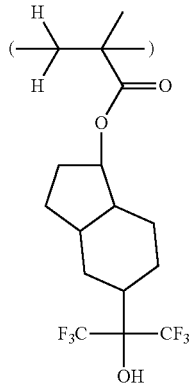
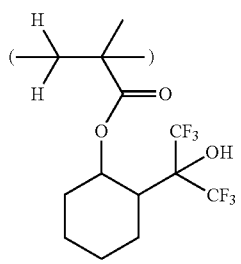
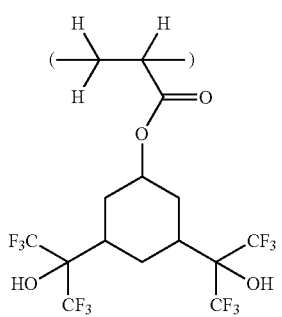
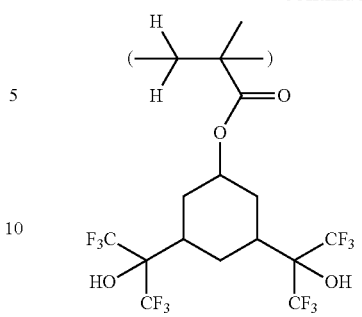
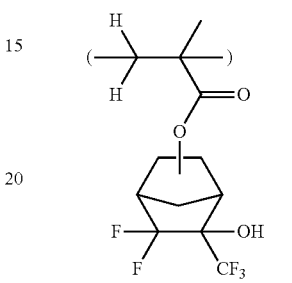
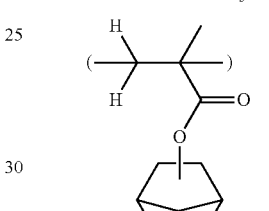
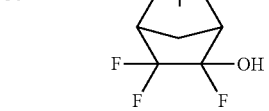
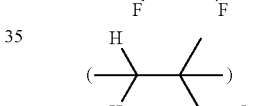
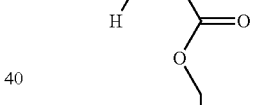
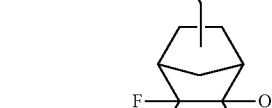
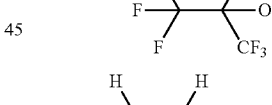
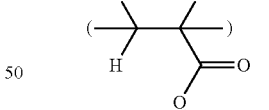
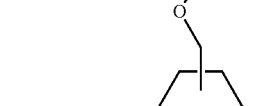
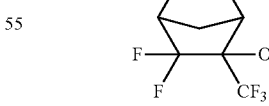
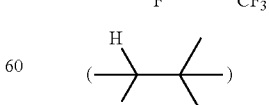
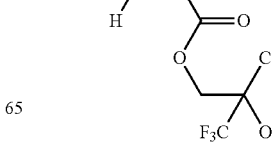

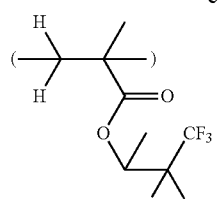
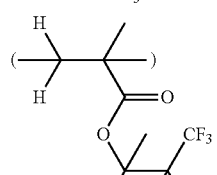
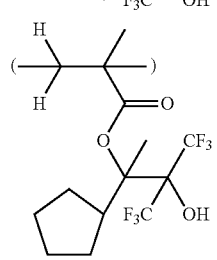
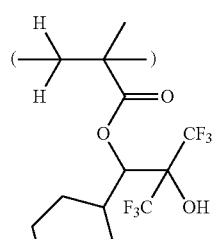
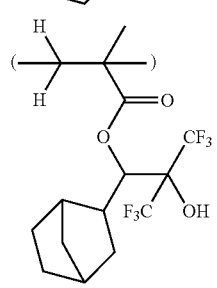
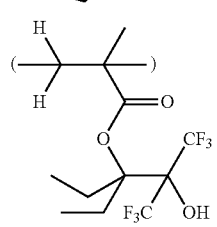
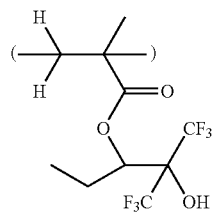
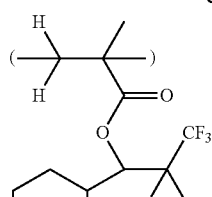
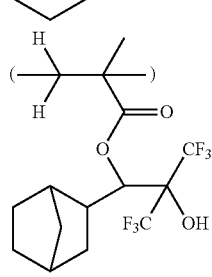
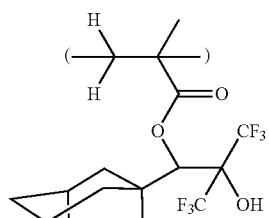
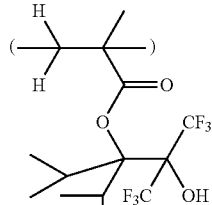
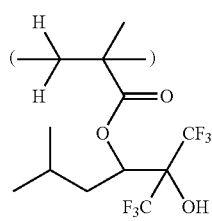
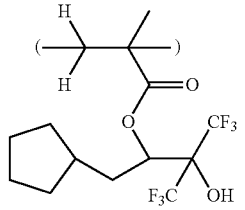
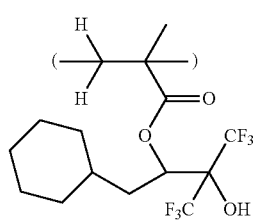

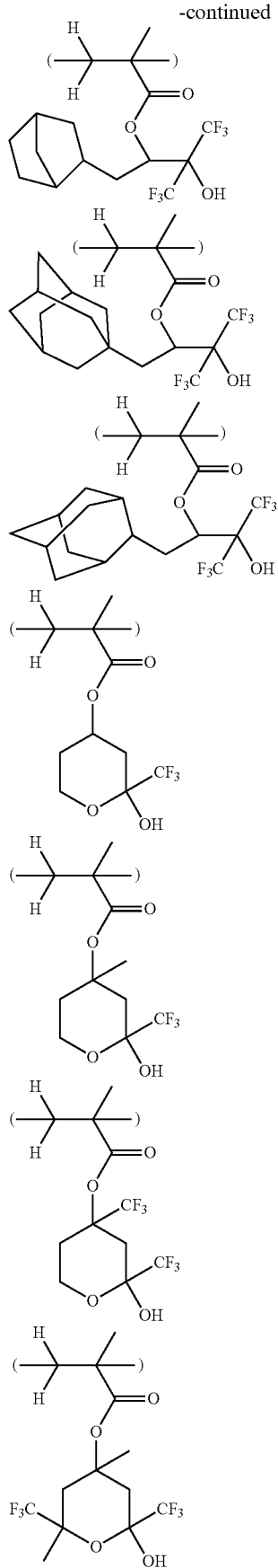
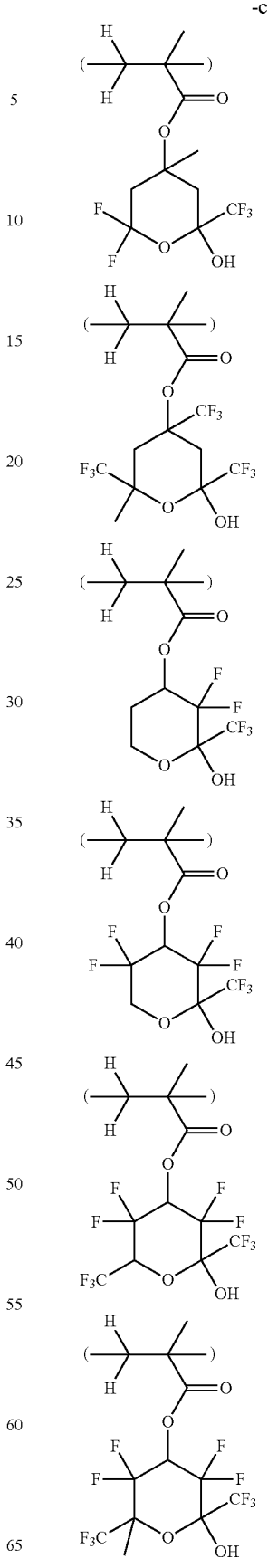

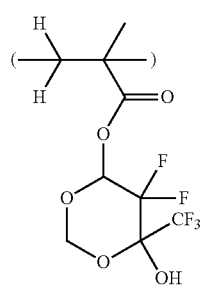
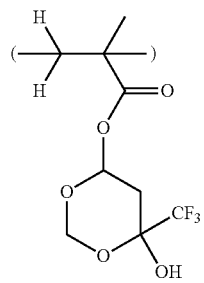
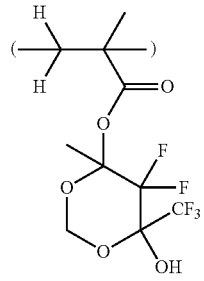
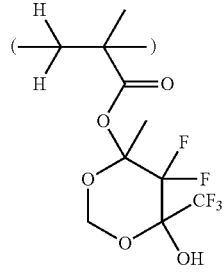
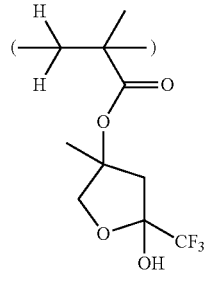
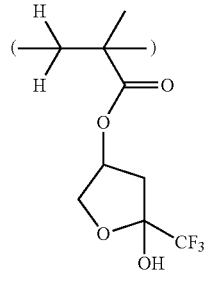
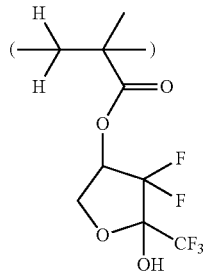
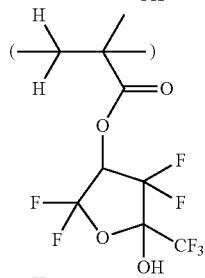
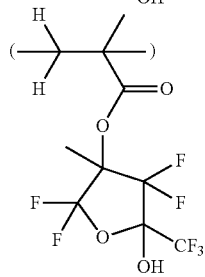
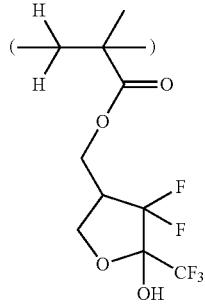
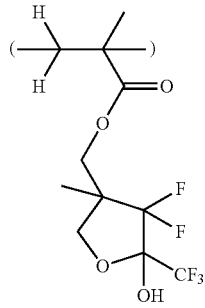
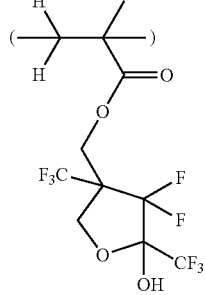

-continued

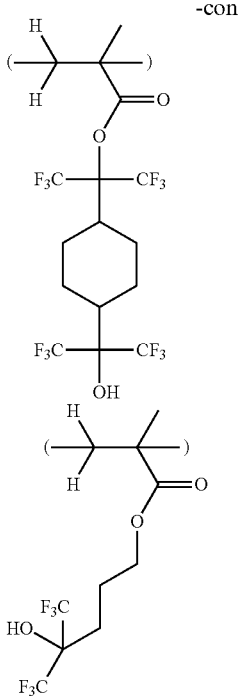

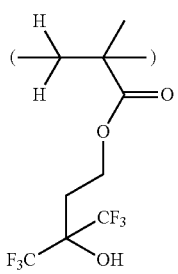

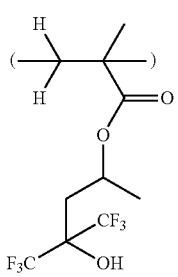

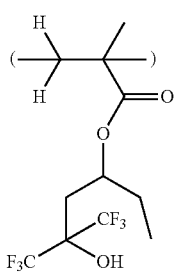

-continued

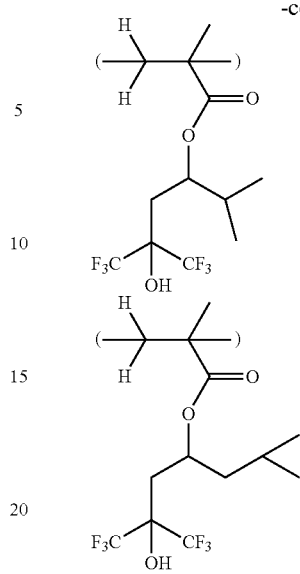

Of the recurring units having formula (6), if used, those units having a lactone ring as the polar group are most preferred.

On use, the recurring units having formula (6) are copolymerized with the recurring units having formula (3A), (3B), (3C), (4A), (4B) or (4C) and the optional recurring units having formula (5), although they may be further copolymerized with other recurring units.

In addition to the foregoing units, the polymer may further comprise recurring units derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[$6.2.1.1^{3,6}.0^{2,7}$]dodecene derivatives, unsaturated acid anhydrides such as itaconic anhydride, styrene, 4-hydroxystyrene, 4-hydroxystyrene derivatives whose hydroxyl group is protected, and other monomers. Also, hydrogenated products of ring-opening metathesis polymerization (ROMP) polymers as described in JP-A 2003-066612 may be used.

The polymer generally has a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

The general method of synthesizing the polymer is, for example, by dissolving one or more unsaturated bond-bearing monomers in an organic solvent, adding a radical initiator, and effecting heat polymerization. Reference may be made to many documents including JP-A 2005-264103. JP-A 2010-077404 describes the synthesis of a polymer comprising copolymerized units having a triphenylsulfonium salt-containing compound whose anion is bound to the polymer backbone, which method is similar to the above-mentioned one. The sulfonium salt having formula (1A), (1B), (1C), (2A), (2B) or (2C) can be polymerized by a similar method.

While the polymer comprises recurring units derived from monomers, the molar fractions of respective units preferably fall in the following range (mol %), but are not limited thereto.

(I) 0.2 to 20 mol %, more preferably 0.5 to 15 mol % of recurring units having formula (3A), (3B), (3C), (4A), (4B) or (4C), (II) 1 to 50 mol %, more preferably 5 to 40 mol %, and even more preferably 10 to 30 mol % of constituent units of at least one type having formula (5), (III) 30 to 98.8 mol %, more preferably 45 to 94.5 mol %, and even more preferably 69.5 to 89.5 mol % of constituent units of at least one type having formula (6), and optionally, (IV) 0 to 80 mol %, more preferably 0 to 70 mol %, and even more preferably 0 to 50 mol % of constituent units of at least one type derived from another monomer(s).

The polymer is not limited to one type and a mixture of two or more polymers may be added. The use of plural polymers allows for easy adjustment of resist properties.

Resist Composition

A further embodiment of the invention is a resist composition comprising (A) a polymer comprising recurring units having formula (3A), (3B), (3C), (4A), (4B) or (4C) as essential component, and optionally, another polymer free of recurring units having formulae (3A), (3B), (3C), (4A), (4B) and (4C). The resist composition may further comprise (B) a photoacid generator capable of generating an acid upon exposure, (C) a quencher, and (D) an organic solvent. Optionally, the resist composition may further comprise (E) a surfactant which is insoluble or substantially insoluble in water and soluble in alkaline developer, and/or a surfactant which is insoluble or substantially insoluble in water and alkaline developer (hydrophobic resin), and (F) an organic acid derivative and/or fluorinated alcohol.

(B) Photoacid Generator

The PAG used herein may be any compound capable of generating an acid upon exposure to high-energy radiation including UV, DUV, EB, EUV, x-ray, excimer laser, γ-ray, and synchrotron radiation. Suitable PAGs include sulfonium salts, iodonium salts, sulfonyldiazomethane, N-sulfonyloxydicarboxylmide, O-arylsulfonyloxime, and O-alkylsulfonyloxime generators. The acid generators may be used alone or in admixture of two or more.

Sulfonium salts are salts of sulfonium cations with sulfonates, bis(substituted alkylsulfonyl)imides and tris(substituted alkylsulfonyl)methides. Suitable sulfonium cations include those cations having the general formula (8).

$$S^+(R^{33}R^{44}R^{55}) \qquad (8)$$

Herein $R^{33}$, $R^{44}$ and $R^{55}$ are each independently a substituted or unsubstituted, straight, branched or cyclic $C_1$-$C_{10}$ alkyl, alkenyl or oxoalkyl group or a substituted or unsubstituted $C_6$-$C_{18}$ aryl, aralkyl or aryloxoalkyl group, or any two of $R^{33}$, $R^{44}$ and $R^{55}$ may bond together to form a ring with the sulfur atom in the formula.

Of the groups represented by $R^{33}$, $R^{44}$ and $R^{55}$, suitable alkyl groups include methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl and thienyl, hydroxyphenyl groups such as 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl, alkoxynaphthyl groups such as methoxynaphthyl and ethoxynaphthyl, dialkylnaphthyl groups such as dimethylnaphthyl and diethylnaphthyl, and dialkoxynaphthyl groups such as dimethoxynaphthyl and diethoxynaphthyl. Suitable aralkyl groups include benzyl, 1-phenylethyl, and 2-phenylethyl. Suitable aryloxoalkyl groups are 2-aryl-2-oxoethyl groups including 2-phenyl-2-oxoethyl, 2-(1-naphthyl)-2-oxoethyl, and 2-(2-naphthyl)-2-oxoethyl. In these hydrocarbon groups, one or more hydrogen atoms may be substituted by fluorine or hydroxyl.

Alternatively, any two of $R^{33}$, $R^{44}$ and $R^{55}$ bond together to form a ring with the sulfur atom in the formula. Exemplary ring structures are given below.

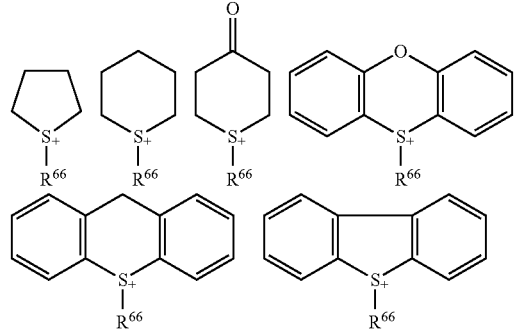

Herein $R^{66}$ is as defined and illustrated for $R^{33}$, $R^{44}$ and $R^{55}$.

As the anion of the sulfonium salt, exemplary sulfonates include trifluoromethanesulfonate, pentafluoroethanesulfonate, heptafluoropropanesulfonate, nonafluorobutanesulfonate, tridecafluorohexanesulfonate, 2,2,2-trifluoroethanesulfonate, pentafluorobenzenesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate. Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Sulfonium salts based on combination of the foregoing examples are included.

Examples of the iodonium salt, N-sulfonyloxydicarboxylmide, O-arylsulfonyloxime, and O-alkylsulfonyloxime (or oximesulfonate) acid generators are described in JP-A 2009-269953 (U.S. Pat. No. 8,114,571).

Preferred examples of the other PAG include triphenylsulfonium nonafluorobutanesulfonate, triphenylsulfonium bis(trifluoromethylsulfonyl)imide, triphenylsulfonium perfluoro(1,3-propylenebissulfonyl)imide, triphenylsulfonium tris(trifluoromethanesulfonyl)methide, N-nonafluorobutanesulfonyloxy-1,8-naphthalenedicarboxylmide, 2-(2,2,3,3,4,4-hexafluoro-1-(nonafluorobutylsulfonyloxy-imino)butyl)fluorene, and 2-(2,2,3,3,4,4,5,5-octafluoro-1-(nonafluorobutylsulfonyloxy-imino)pentyl)fluorene.

The preferred structure of PAG includes compounds having the general formula (P1).

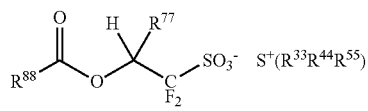

(P1)

Herein $R^{77}$ is hydrogen or trifluoromethyl, $R^{88}$ is a $C_1$-$C_{30}$ alkyl, alkenyl or aralkyl group which may contain a heteroatom, $R^{33}$, $R^{44}$ and $R^{55}$ are as defined above.

In formula (P1), $R^{88}$ is a $C_1$-$C_{30}$ alkyl, alkenyl or aralkyl group optionally containing a heteroatom. Suitable heteroatoms contained in $R^{88}$ include oxygen, nitrogen, sulfur and halogen atoms, with oxygen being preferred. The $C_1$-$C_{30}$ alkyl, alkenyl or aralkyl group of $R^{88}$ may be straight, branched or cyclic while it is preferred for achieving a high resolution sufficient to form a fine size pattern that these groups have 6 to 30 carbon atoms. It is undesirable that $R^{88}$ be aryl because the resulting resist pattern may have less smooth sidewalls. Exemplary groups of $R^{88}$ include, but are not limited to, methyl, ethyl, propyl, isopropyl, butyl, isobutyl, s-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having formula (P1), reference may be made to JP-A 2007-145797, 2008-106045, 2009-007327, and 2009-258695, for example.

Illustrative examples of the preferred PAG are given below.

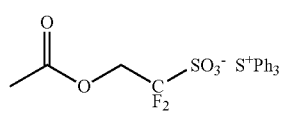

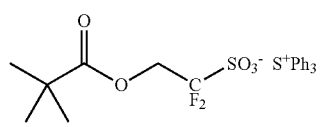

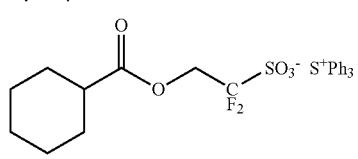

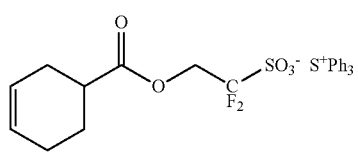

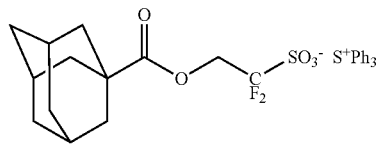

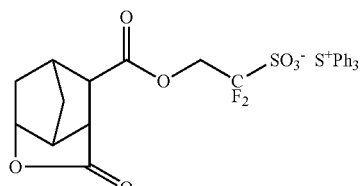

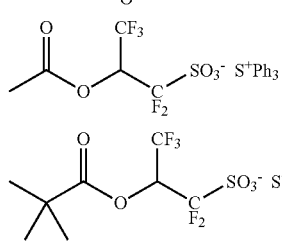

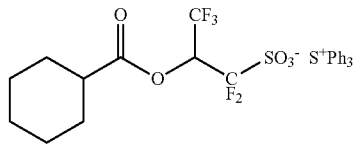

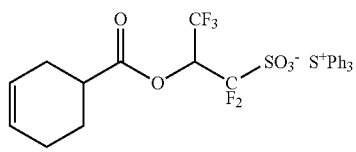

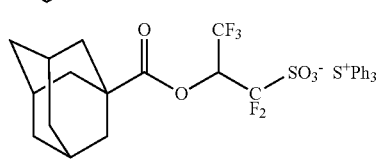

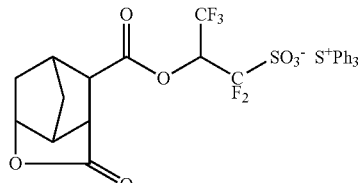

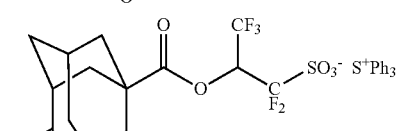

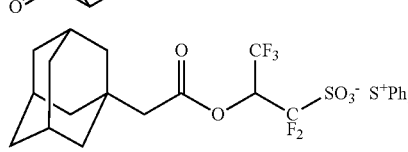

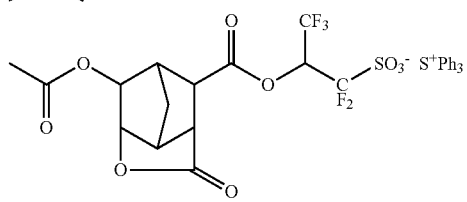

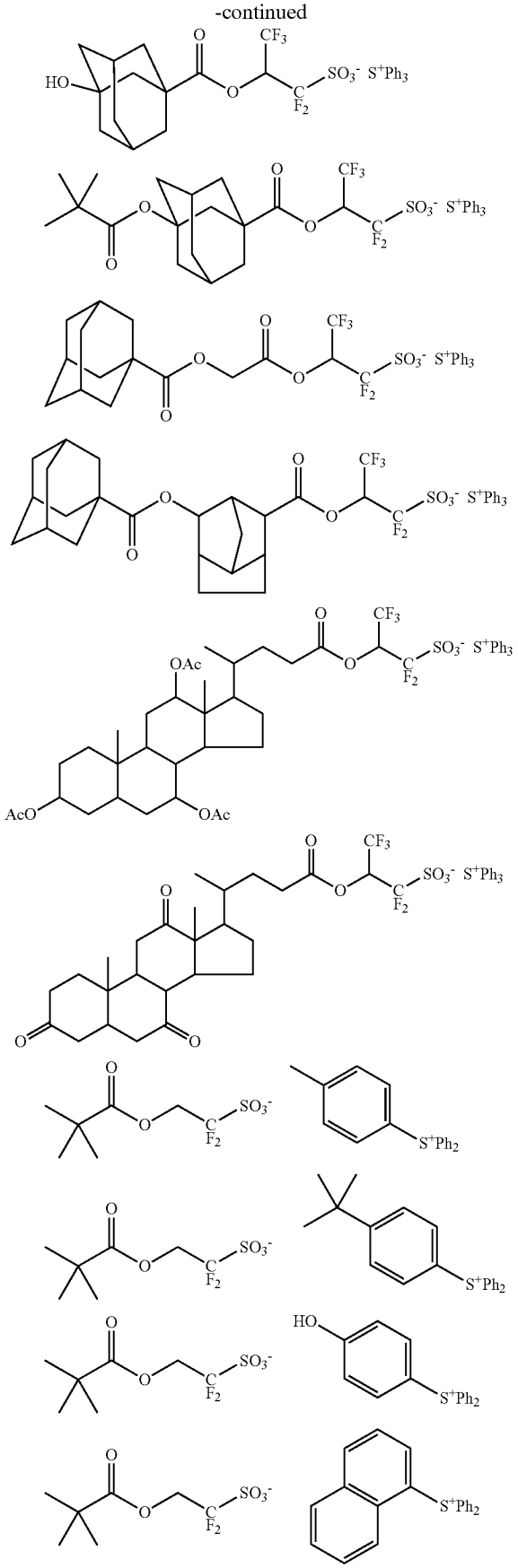
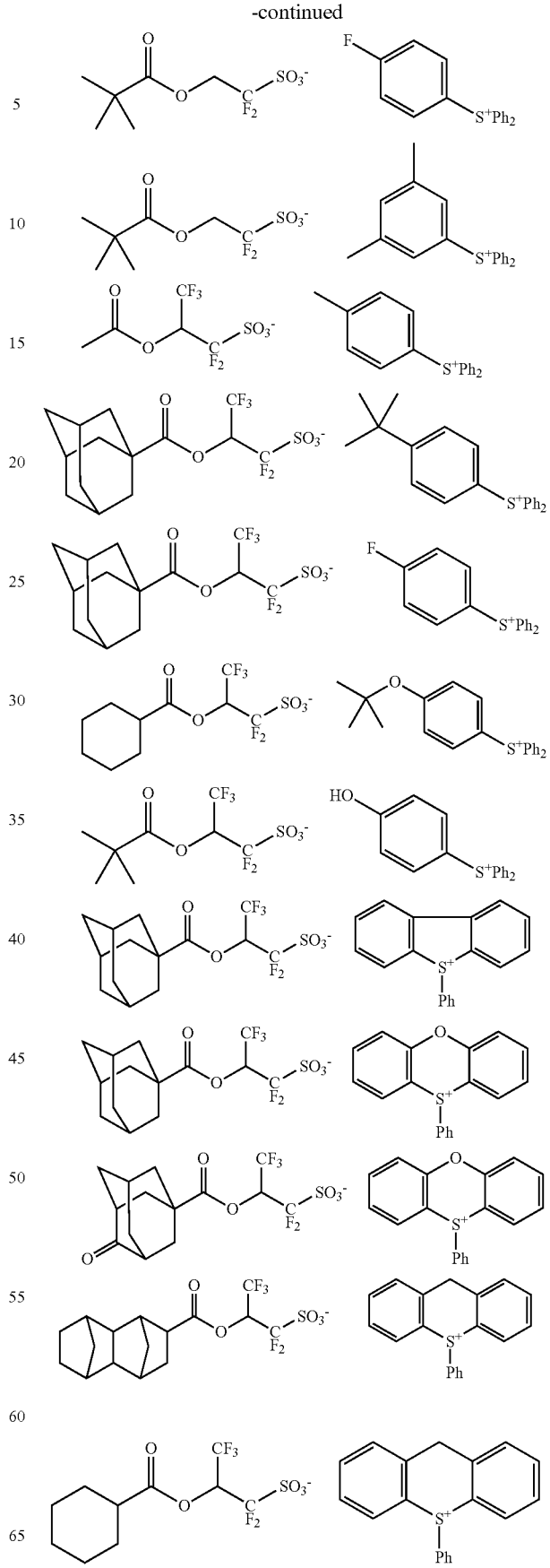

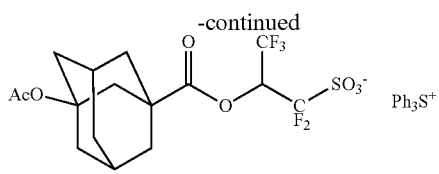

Herein Ac stands for acetyl and Ph stands for phenyl.

An appropriate amount of the PAG having formula (P1) added is 0 to 40 parts by weight, and if added, 0.1 to 40 parts, and more preferably 0.1 to 20 parts by weight per 100 parts by weight of the polymer as base resin. Too high a proportion of the PAG may give rise to problems such as degraded resolution and foreign particles during development and resist film stripping. The PAG having formula (P1) may be used alone or in admixture of two or more or in admixture with another PAG. When the other PAG is added, its amount is arbitrary as long as the objects of the invention are not compromised. Typically the amount of the other PAG is 0 to 20 parts, preferably 0.1 to 10 parts by weight per 100 parts by weight of the polymer.

Notably, the resist composition comprises as base resin (A) a polymer comprising recurring units having formula (3A), (3B), (3C), (4A), (4B) or (4C), which functions as PAG. Therefore, it is unnecessary to add PAG (B) although it is acceptable to use one or more PAGs (B) in combination with base resin (A).

It is noted that an acid diffusion controlling function may be provided when two or more PAGs are used in admixture provided that one PAG is an onium salt capable of generating a weak acid. Specifically, in a system using a mixture of an onium salt capable of generating a strong acid (e.g., fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the PAG capable of generating a strong acid is an onium salt, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

(C) Quencher

The quencher (C) may be a compound capable of suppressing the rate of diffusion when the acid generated by the PAG diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Of these, preferred are tertiary amines, amine oxides, benzimidazoles, and anilines having a polar functional group such as ether, carbonyl, ester or alcohol.

Preferred tertiary amines include 2-morpholinoethyl esters of straight, branched or cyclic $C_2$-$C_{20}$ aliphatic carboxylic acids and trialkylamines having a straight, branched or cyclic $C_2$-$C_{10}$ alkyl moiety. Also included are substituted forms of these amines in which some carbon-bonded hydrogen atoms are replaced by hydroxyl groups. These amines may have an ether or ester linkage. Examples include 2-morpholinoethyl 2-methoxyacetate, 2-morpholinoethyl 2-(2-methoxyethoxy) acetate, 2-morpholinoethyl 2-[2-(2-methoxyethoxy)ethoxy] acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl cyclohexanecarboxylate, 2-morpholinoethyl adamantanecarboxylate, 4-[2-[(2-methoxyethoxy)methoxy]ethyl]morpholine, 4-[2-[2-(2-methoxyethoxy)ethoxy]ethyl]morpholine, 4-[2-[2-(2-butoxyethoxy)ethoxy]ethyl]morpholine, tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, and tris(2-pivaloyloxyethyl)amine.

Preferred examples of the benzimidazoles include benzimidazole, 2-phenylbenzimidazole, 1-(2-acetoxyethoxy) benzimidazole, 1-[2-(methoxymethoxy)ethyl]benzimidazole, 1-[2-(methoxymethoxy)ethyl]-2-phenylbenzimidazole, and 1-(2-(2-(2-methoxyethoxy) ethoxy)ethyl)benzimidazole.

Preferred examples of the anilines include aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine.

Also included are primary and secondary amines which have been protected with tert-butoxycarbonyl (tBOC). Those compounds described in JP-A 2007-298569 and JP-A 2010-020204 are also useful.

The quenchers may be used alone or in admixture of two or more. The quencher is preferably used in an amount of 0.001 to 8 parts, more preferably 0.01 to 4 parts by weight per 100 parts by weight of the base resin. Less than 0.001 part of the quencher may achieve no addition effect whereas more than 8 parts may lead to too low a sensitivity.

(D) Organic Solvent

The organic solvent (D) used herein may be any organic solvent in which the polymer (or base resin), acid generator, quencher, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, propylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in combinations of two or more. Of the above organic solvents, it is recommended to use 1-ethoxy-2-propanol, PGMEA, cyclohexanone, γ-butyrolactone, and mixtures thereof because the acid generator is most soluble therein.

An appropriate amount of the organic solvent used is 200 to 5,000 parts, more preferably 400 to 3,000 parts by weight per 100 parts by weight of the base resin.

(E) Surfactant

Component (E) is a surfactant which is insoluble or substantially insoluble in water and soluble in alkaline developer, and/or a surfactant which is insoluble or substantially insoluble in water and alkaline developer (hydrophobic resin). The surfactant (E) may be added to the resist composition. Reference should be made to those compounds defined as component (S) in JP-A 2010-215608 and JP-A 2011-016746.

While many examples of the surfactant which is insoluble or substantially insoluble in water and alkaline developer are described in these patent documents, preferred examples are FC-4430, Surflon S-381, Surfynol E1004, KH-20 and KH-30, which may be used alone or in admixture. Partially fluorinated oxetane ring-opened polymers having the structural formula (surf-1) are also useful.

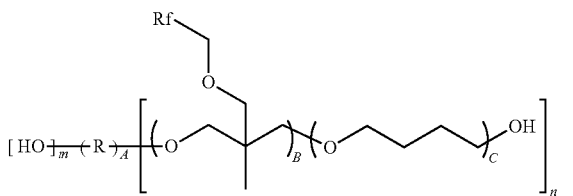

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

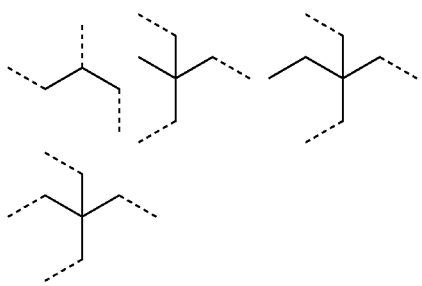

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage. Suitable polymeric surfactants are shown below.

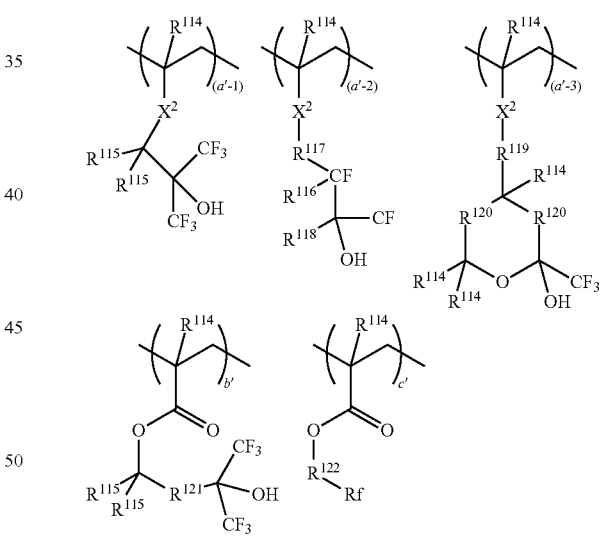

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$. $R^{121}$ is a straight or branched $C_1$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range: $0 \le (a'\text{-}1) < 1$, $0 \le (a'\text{-}2) < 1$, $0 \le (a'\text{-}3) < 1$, $0 < (a'\text{-}1)+(a'\text{-}2)+(a'\text{-}3) < 1$, $0 \le b' < 1$, $0 \le c' < 1$, and $0 < (a'\text{-}1)+(a'\text{-}2)+(a'\text{-}3)+b'+c' \le 1$.

Examples of these units are shown below.

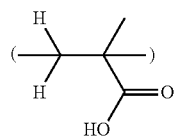

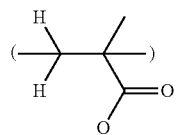

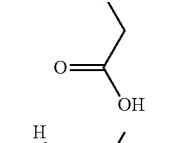

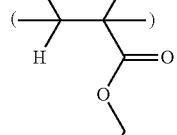

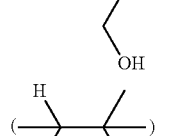

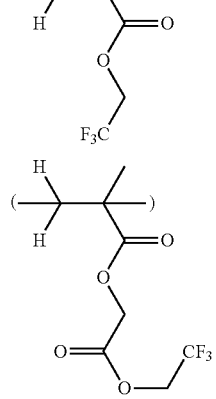

-continued

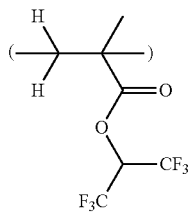

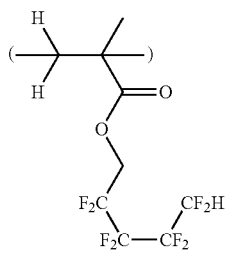

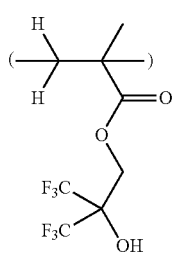

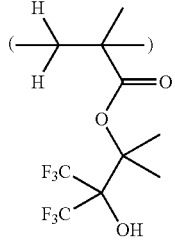

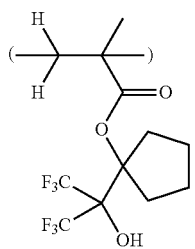

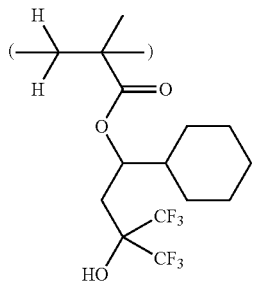

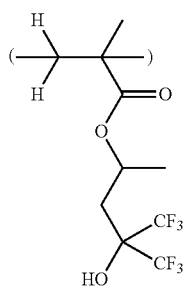
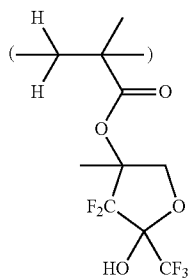
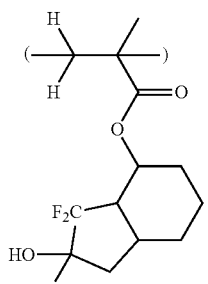
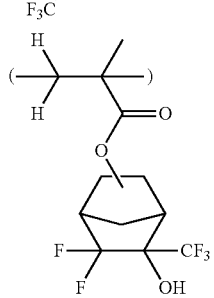
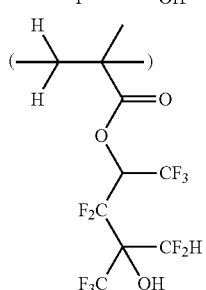
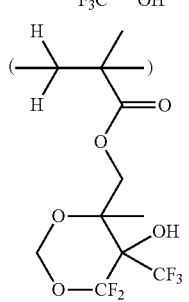
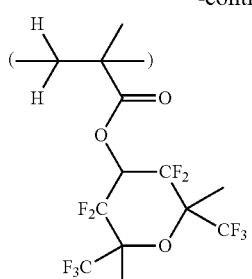
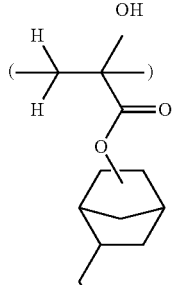
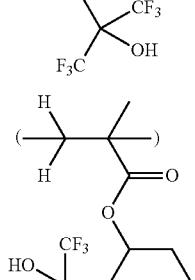
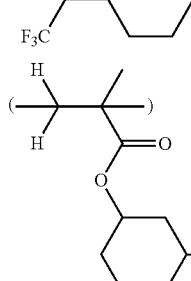
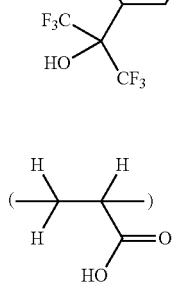
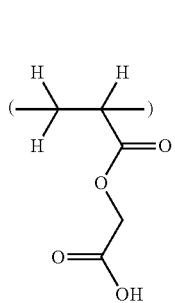

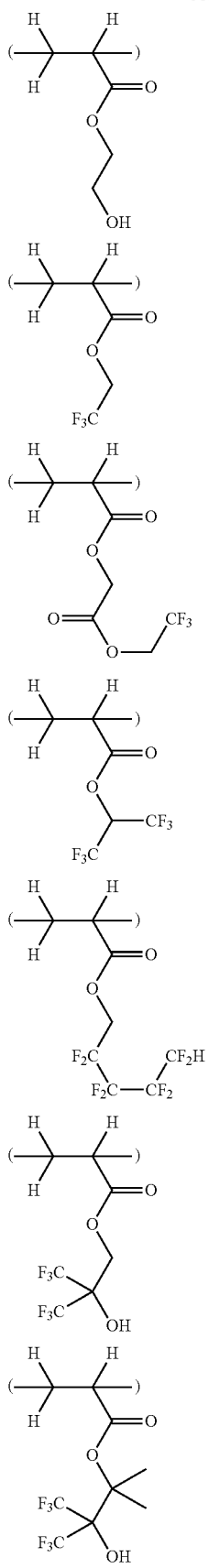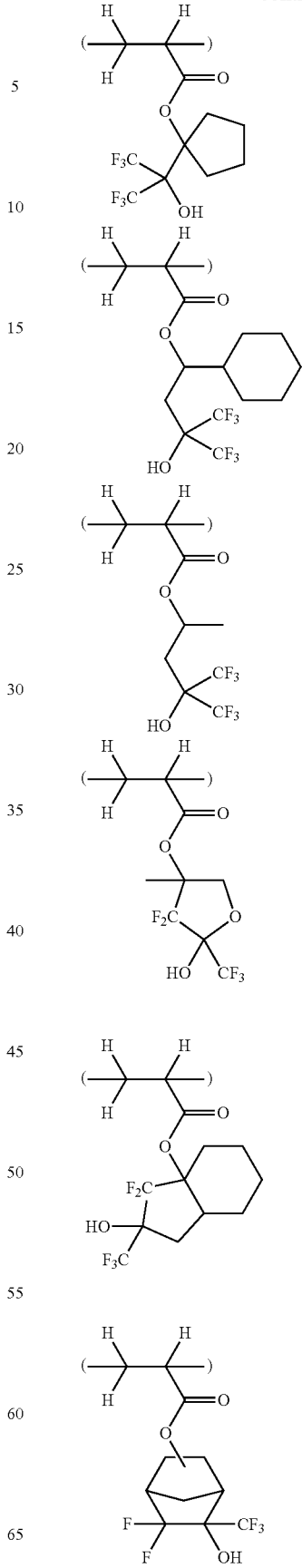

-continued

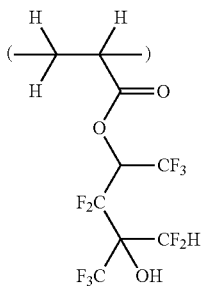

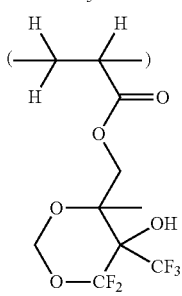

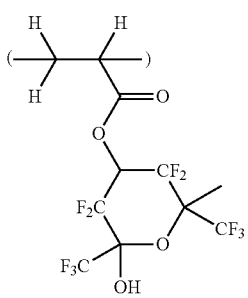

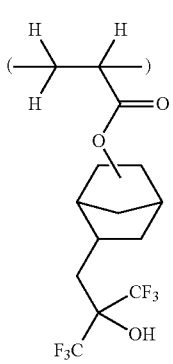

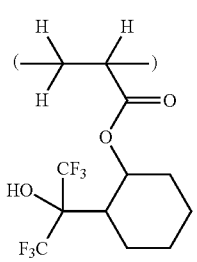

-continued

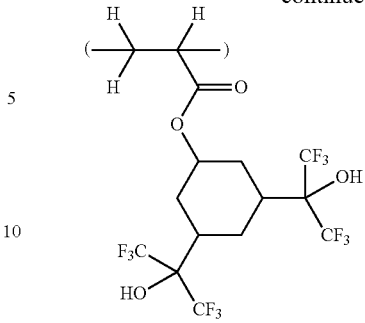

For the surfactant which is insoluble or substantially insoluble in water and soluble in alkaline developer, reference may be made to JP-A 2008-122932, 2010-134012, 2010-107695, 2009-276363, 2009-192784, 2009-191151, 2009-98638, 2010-250105, and 2011-42789.

The polymeric surfactant preferably has a Mw of 1,000 to 50,000, more preferably 2,000 to 20,000 as measured by GPC versus polystyrene standards. A surfactant with a Mw outside the range may be less effective for surface modification and cause development defects. The polymeric surfactant is preferably formulated in an amount of 0.001 to 20 parts, and more preferably 0.01 to 10 parts by weight per 100 parts by weight of the base resin. Reference should also be made to JP-A 2010-215608.

(F) Organic Acid Derivative and/or Fluorinated Alcohol

To the resist composition, a compound which is decomposed with an acid to generate another acid, that is, acid amplifier compound may be added. For these compounds, reference should be made to JP-A 2009-269953 and 2010-215608. In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Optionally, an organic acid derivative or a compound having a Mw of up to 3,000 which changes its solubility in alkaline developer under the action of an acid, also referred to as dissolution inhibitor, may be added. Reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

First the resist composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 10 minutes, preferably 80 to 140° C. for 1 to 5 minutes. The resulting resist film is generally 0.05 to 2.0 μm thick. Through a photomask having a desired pattern disposed over the substrate, the resist film is then exposed to high-energy radiation such as deep-UV, excimer laser or x-ray, or electron beam in an exposure dose preferably in the range of 1 to 200 $mJ/cm^2$, more preferably 10 to 100 $mJ/cm^2$. Alternatively, pattern formation may be performed by writing with an electron beam directly (not through a mask). Light exposure may be done by a conventional lithography process or in some cases, by an immersion lithography process of providing liquid impregnation, typically water, between the projection lens or mask and the resist film. In the case of immersion lithography, a protective film which is insoluble in water may be used. The resist film is then baked (PEB) on a hot plate at 60 to 150° C. for 1 to 5 minutes, and preferably at 80 to 140° C. for 1 to 3 minutes. Finally, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. In this way the desired pattern is formed on the substrate. Of the various types of high-energy radiation that may be used, the resist composition of the invention is best suited to fine pattern formation with, in particular, deep-UV or excimer laser having a wavelength of 250 to 190 nm, x-ray, or EB. The desired pattern may not be obtainable outside the upper and lower limits of the above range.

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, an alkaline aqueous solution, typically an aqueous solution of 0.1 to 5 wt %, more typically 2 to 3 wt % of tetramethylammonium hydroxide (TMAH) is often used as the developer. The negative tone development technique wherein the unexposed region is developed and dissolved in an organic solvent is also applicable.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples and Comparative Examples are given below by way of illustration and not by way of limitation. Mw is weight average molecular weight and Mw/Mn is dispersity. All parts are by weight (pbw).

A series of resins P-1 to P-14 as shown in Table 1 were prepared by the standard procedure while changing the type and ratio of monomers. The units in Table 1 have the structure shown in Tables 2 to 4. In Table 1, the ratio of units is a molar ratio.

TABLE 1

| Resin | Unit 1 (ratio) | Unit 2 (ratio) | Unit 3 (ratio) | Unit 4 (ratio) | Unit 5 (ratio) |
|---|---|---|---|---|---|
| P-1 | PAG-1 (0.10) | A-3 (0.30) | B-3 (0.30) | B-5 (0.30) | — |
| P-2 | PAG-1 (0.10) | A-3 (0.30) | B-2 (0.30) | B-5 (0.30) | — |
| P-3 | PAG-1 (0.20) | A-3 (0.30) | B-3 (0.20) | B-5 (0.30) | — |
| P-4 | PAG-1 (0.20) | A-3 (0.30) | B-2 (0.20) | B-5 (0.30) | — |
| P-5 | A-3 (0.30) | B-3 (0.40) | B-6 (0.30) | — | — |
| P-6 | PAG-1 (0.05) | A-1 (0.55) | B-1 (0.10) | B-4 (0.30) | — |
| P-7 | PAG-1 (0.10) | A-2 (0.40) | A-4 (0.20) | B-3 (0.30) | — |
| P-8 | PAG-1 (0.10) | A-5 (0.30) | B-4 (0.30) | B-6 (0.30) | — |
| P-9 | PAG-1 (0.10) | A-4 (0.20) | A-6 (0.20) | B-3 (0.20) | B-5 (0.30) |
| P-10 | PAG-2 (0.10) | A-3 (0.30) | B-3 (0.30) | B-5 (0.30) | — |
| P-11 | PAG-3 (0.10) | A-3 (0.30) | B-3 (0.30) | B-5 (0.30) | — |
| P-12 | PAG-2 (0.05) | A-1 (0.55) | B-1 (0.10) | B-4 (0.30) | — |
| P-13 | A-1 (0.55) | B-1 (0.15) | B-4 (0.30) | — | — |
| P-14 | A-3 (0.30) | B-3 (0.40) | B-5 (0.30) | — | — |

TABLE 2
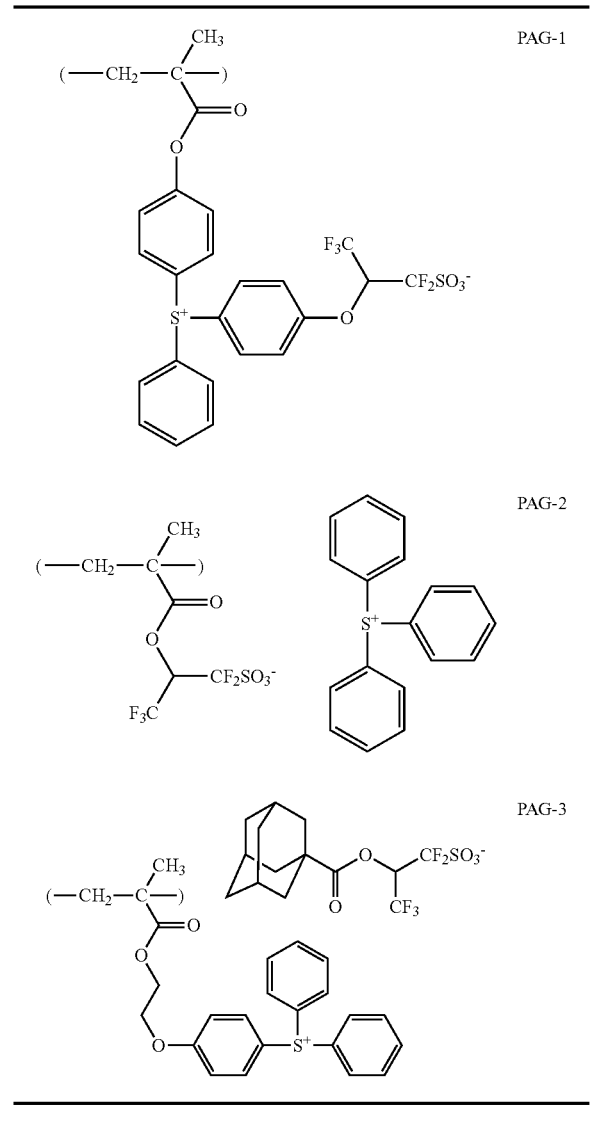
TABLE 3
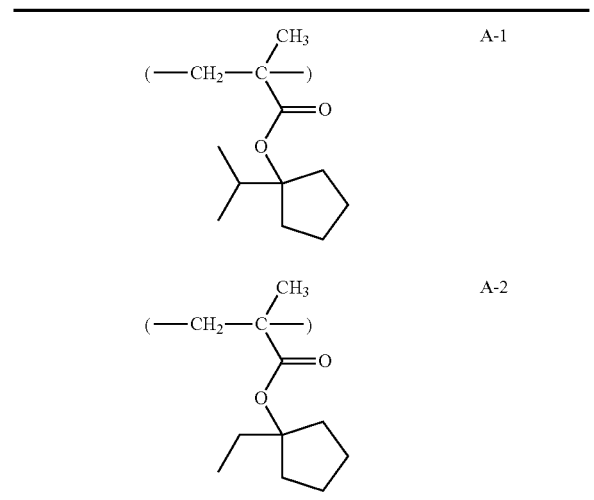
TABLE 3-continued
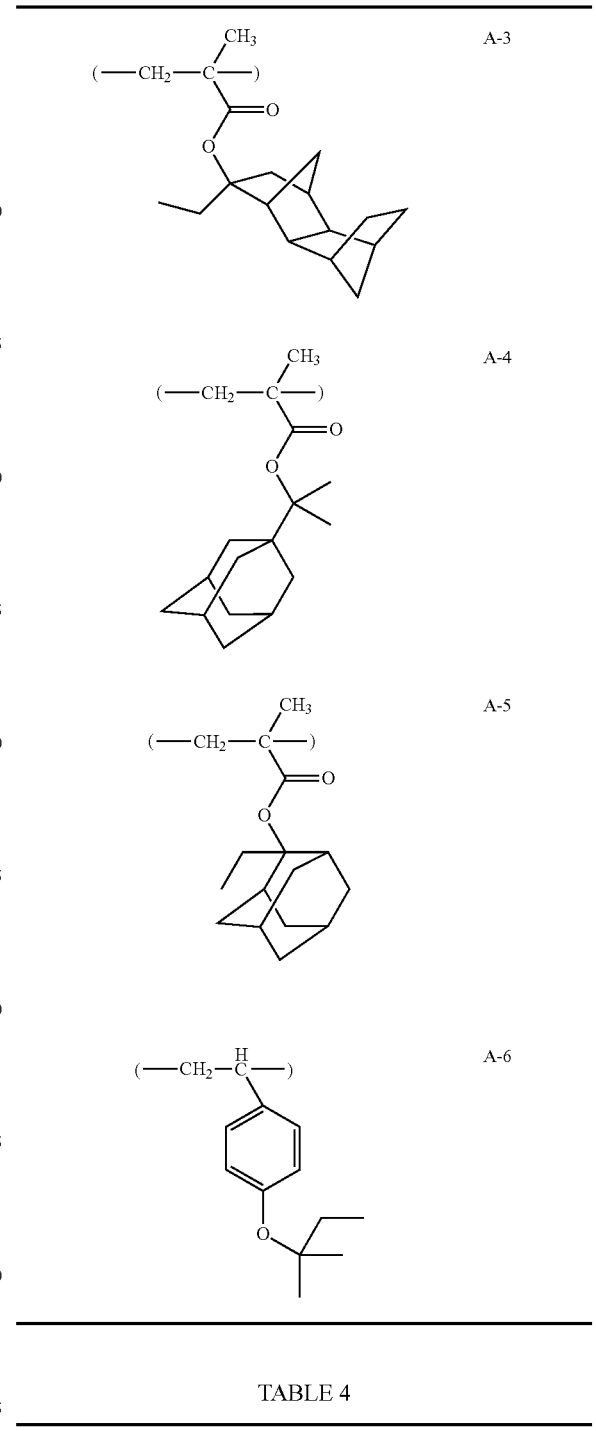
TABLE 4
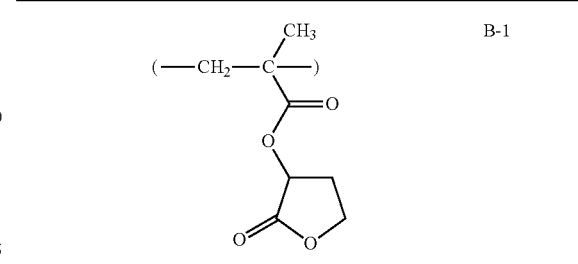

TABLE 4-continued

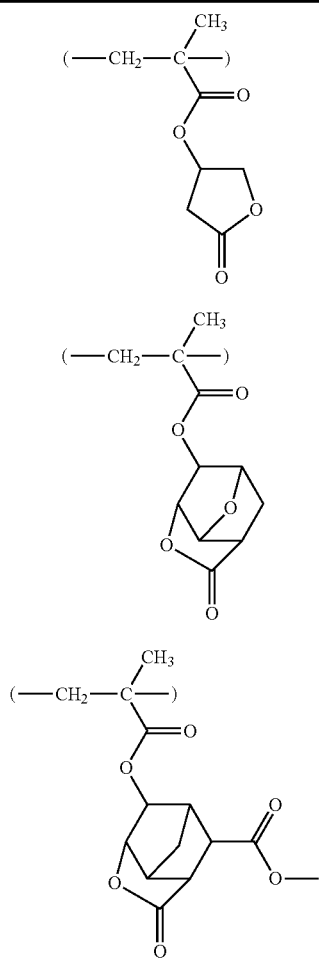

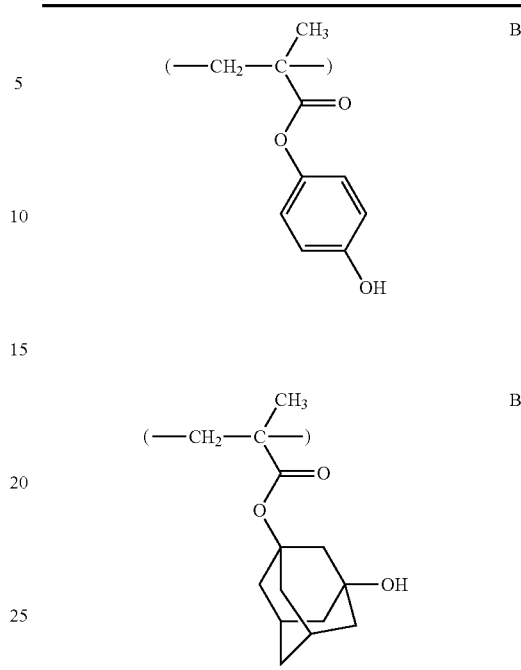

Examples 1-1 to 1-11 and Comparative Examples 1-1 to 1-5

Resist compositions in solution form were prepared by mixing and dissolving a polymer (Table 1), PAG, amine quencher, and alkali-soluble surfactant (F-1) in a solvent according to the formulation shown in Table 5 and filtering through a Teflon® filter having a pore size of 0.2 μm. In all runs, the solvent contained 0.01 wt % of surfactant (F-2).

TABLE 5

|  |  | Resist | Resin (pbw) | PAG (pbw) | Quencher (pbw) | Surfactant (pbw) | Solvent 1 (pbw) | Solvent 2 (pbw) |
|---|---|---|---|---|---|---|---|---|
| Example | 1-1 | R-01 | P-1 (80) | — | Q-1 (0.9) | F-1 (5.0) | PGMEA (576) | CyHO (1,728) |
|  | 1-2 | R-02 | P-2 (80) | — | Q-1 (0.9) | F-1 (5.0) | PGMEA (576) | CyHO (1,728) |
|  | 1-3 | R-03 | P-3 (80) | — | Q-1 (0.9) | F-1 (5.0) | PGMEA (576) | CyHO (1,728) |
|  | 1-4 | R-04 | P-4 (80) | — | Q-1 (0.9) | F-1 (5.0) | PGMEA (576) | CyHO (1,728) |
|  | 1-5 | R-05 | P-6 (80) | — | Q-1 (0.9) | F-1 (5.0) | PGMEA (576) | CyHO (1,728) |
|  | 1-6 | R-06 | P-7 (80) | — | Q-1 (0.9) | F-1 (5.0) | PGMEA (576) | CyHO (1,728) |
|  | 1-7 | R-07 | P-8 (80) | — | Q-1 (0.9) | F-1 (5.0) | PGMEA (576) | CyHO (1,728) |
|  | 1-8 | R-08 | P-1 (40) P-5 (40) | — | Q-1 (0.9) | F-1 (5.0) | PGMEA (576) | CyHO (1,728) |
|  | 1-9 | R-09 | P-1 (80) | PAG-4 (2.0) | Q-1 (0.9) | F-1 (5.0) | PGMEA (576) | CyHO (1,728) |
|  | 1-10 | R-10 | P-1 (80) | PAG-5 (5.7) | — | F-1 (5.0) | PGMEA (576) | CyHO (1,728) |
|  | 1-11 | R-11 | P-9 (80) | — | Q-1 (0.9) | F-1 (5.0) | PGMEA (576) | CyHO (1,728) |

TABLE 5-continued

|  |  | Resist | Resin (pbw) | PAG (pbw) | Quencher (pbw) | Surfactant (pbw) | Solvent 1 (pbw) | Solvent 2 (pbw) |
|---|---|---|---|---|---|---|---|---|
| Comparative Example | 1-1 | R-12 | P-10 (80) | — | Q-1 (0.9) | F-1 (5.0) | PGMEA (576) | CyHO (1,728) |
|  | 1-2 | R-13 | P-11 (80) | — | Q-1 (0.9) | F-1 (5.0) | PGMEA (576) | CyHO (1,728) |
|  | 1-3 | R-14 | P-12 (80) | — | Q-1 (0.9) | F-1 (5.0) | PGMEA (1,344) | GBL (192) |
|  | 1-4 | R-15 | P-13 (80) | — | Q-1 (0.9) | F-1 (5.0) | PGMEA (1,344) | GBL (192) |
|  | 1-5 | R-16 | P-14 (80) | — | Q-1 (0.9) | F-1 (5.0) | PGMEA (1,728) | CyHO (576) |

The PAG, solvent, amine quencher, alkali-soluble surfactant (F-1) and surfactant (F-2) used herein are identified below.

[Photoacid Generator]

PAG-4: triphenylsulfonium 2-(adamantane-1-carbonyloxy)-1,1,3,3,3-pentafluoropropane-1-sulfonate (see JP-A 2007-145797)

PAG-5: triphenylsulfonium camphorsulfonate

[Organic Solvent]

PGMEA: propylene glycol monomethyl ether acetate

GBL: γ-butyrolactone

CyHO: cyclohexanone

[Quencher]

Q-1: 2,6-diisopropylaniline

[Surfactant]

F-1: poly(3,3,3-trifluoro-2-hydroxy-1,1-dimethyl-2-trifluoromethylpropyl methacrylate/1,1,1-trifluoro-2-hydroxy-6-methyl-2-trifluoromethylhept-4-yl methacrylate) (described in JP-A 2008-122932)

Mw=7,300 Mw/Mn=1.86

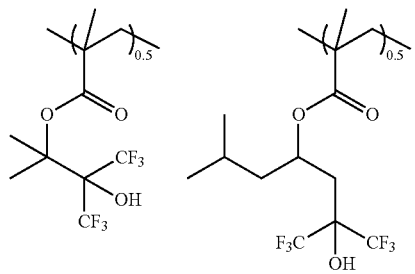

F-2: 3-methyl-3-(2,2,2-trifluoroethoxymethyl)oxetane/tetrahydrofuran/2,2-dimethyl-1,3-propane diol copolymer (Omnova Solutions, Inc.)

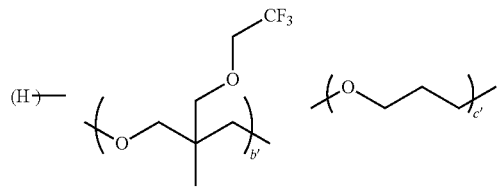

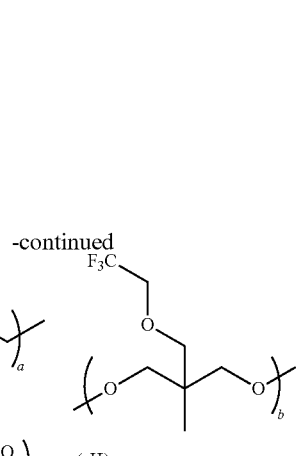

a: (b+b'):(c+c')=1:4-7:0.01-1 (molar ratio)
Mw=1,500

Resist Test 1

ArF Lithography

Examples 2-1 to 2-3 and Comparative Examples 2-1 to 2-2

On a silicon substrate, an antireflective coating solution (ARC-29A, Nissan Chemical Industries, Ltd.) was coated and baked at 200° C. for 60 seconds to form an ARC of 78 nm thick. Each of inventive resist compositions (R-05 to R-07) and comparative resist compositions (R-14 and R-15) was spin coated on the silicon substrate and baked on a hot plate at 100° C. for 60 seconds, forming a resist film of 100 nm thick on the ARC. The wafer was exposed by means of an ArF excimer laser scanner (NSR-S307E by Nikon Corp., NA 0.85, 4/5 annular illumination, 6% halftone phase shift mask), baked (PEB) at 100° C. for 60 seconds, and developed in a 2.38 wt % tetramethylammonium hydroxide (TMAH) aqueous solution for 60 seconds, forming a pattern.

For resist evaluation, the optimum exposure (Eop) was defined as the exposure dose (mJ/cm$^2$) which provided a 1:1 resolution at the top and bottom of a 80-nm grouped line-and-space pattern. The maximum resolution of the resist was defined as the minimum line width (nm) of a line-and-space pattern that was resolved and separated at the optimum exposure. For the evaluation of exposure latitude, an exposure dose tolerance which provided a pattern size of 80 nm ±10% when the exposure dose was changed from the optimum was determined, and the tolerance value was divided by the optimum dose and expressed in percent. A greater value indicates a smaller performance change with a change of exposure dose, that is, better exposure latitude. The line width roughness (LWR) of a 80-nm line-and-space pattern was measured using measurement SEM (S-9380 by Hitachi Hitechnologies, Ltd.). The test results of the resist compositions are shown in Table 6.

TABLE 6

| | | Resist | Eop (mJ/cm$^2$) | Maximum resolution (nm) | Exposure latitude (%) | LWR (nm) |
|---|---|---|---|---|---|---|
| Example | 2-1 | R-05 | 32 | 75 | 15.2 | 5.6 |
| | 2-2 | R-06 | 34 | 80 | 14.4 | 5.9 |
| | 2-3 | R-07 | 40 | 80 | 14.5 | 5.8 |
| Comparative Example | 2-1 | R-14 | 32 | 90 | 13.8 | 6.1 |
| | 2-2 | R-15 | 36 | 85 | 11.9 | 6.9 |

The data of Examples in Table 6 demonstrate that the resist composition comprising a sulfonium salt-containing polymer within the scope of the invention exhibits high resolution, good exposure latitude and low LWR values when processed by ArF lithography.

Resist Test 2

EB Writing

Examples 3-1 to 3-8 and Comparative Examples 3-1 to 3-3

Using a coater/developer system Clean Track Mark 5 (Tokyo Electron Ltd.), the resist composition was spin coated onto a silicon substrate (diameter 6 inches=150 mm, vapor primed with hexamethyldisilazane (HMDS)) and pre-baked on a hot plate at 110° C. for 60 seconds to form a resist film of 100 nm thick. Using a system HL-800D (Hitachi Ltd.) at a HV voltage of 50 keV, the resist film was exposed imagewise to EB in a vacuum chamber.

Using Clean Track Mark 5, immediately after the imagewise exposure, the resist film was baked (PEB) on a hot plate at 95° C. for 60 seconds and puddle developed in a 2.38 wt % TMAH aqueous solution for 30 seconds to form a positive pattern.

Sensitivity is the exposure dose that provides a 1:1 resolution of a 100-nm line-and-space pattern. Resolution is a minimum size at the exposure dose. The 100-nm L/S pattern was measured for LWR under SEM.

Table 7 shows the sensitivity, resolution and LWR of resist compositions on EB lithography.

TABLE 7

| | | Resist | Sensitivity (µC/cm$^2$) | Resolution (nm) | LWR (nm) |
|---|---|---|---|---|---|
| Example | 3-1 | R-01 | 25.9 | 75 | 5.8 |
| | 3-2 | R-02 | 26.1 | 75 | 5.9 |
| | 3-3 | R-03 | 22.4 | 70 | 5.2 |
| | 3-4 | R-04 | 22.5 | 70 | 5.3 |
| | 3-5 | R-08 | 26.1 | 75 | 6.0 |
| | 3-6 | R-09 | 25.9 | 75 | 6.1 |
| | 3-7 | R-10 | 26.3 | 75 | 5.9 |
| | 3-8 | R-11 | 22.3 | 70 | 6.4 |
| Comparative Example | 3-1 | R-12 | 26.5 | 80 | 7.9 |
| | 3-2 | R-13 | 27.0 | 85 | 8.2 |
| | 3-3 | R-16 | 26.4 | 85 | 8.6 |

As is evident from Table 7, the resist composition comprising a sulfonium salt-containing polymer within the scope of the invention shows a high resolution and a low LWR on EB lithography.

Resist Test 3

EUV Exposure

Examples 4-1 to 4-8 and Comparative Examples 4-1 to 4-3

A positive resist composition was prepared by dissolving selected components in a solvent in accordance with the recipe shown in Table 5, and filtering through a filter having a pore size of 0.2 µm. The resist composition was spin coated on a silicon substrate (diameter 4 inches=100 mm, HMDS vapor primed) and prebaked on a hot plate at 105° C. for 60 seconds to form a resist film of 50 nm thick. EUV exposure was performed by dipole illumination at NA 0.3.

Immediately after the exposure, the resist film was baked (PEB) on a hot plate for 60 seconds and puddle developed in a 2.38 wt % TMAH aqueous solution for 30 seconds to form a positive pattern.

Sensitivity is the exposure dose that provides a 1:1 resolution of a 35-nm line-and-space pattern. Resolution is a minimum size at the exposure dose. The 35-nm L/S pattern was measured for LWR under SEM.

Table 8 shows the sensitivity, resolution and LWR of resist compositions on EUV lithography.

TABLE 8

| | | Resist | Sensitivity (mJ/cm$^2$) | Resolution (nm) | LWR (nm) |
|---|---|---|---|---|---|
| Example | 4-1 | R-01 | 12 | 30 | 4.3 |
| | 4-2 | R-02 | 12 | 30 | 4.2 |
| | 4-3 | R-03 | 10 | 28 | 4.6 |
| | 4-4 | R-04 | 11 | 28 | 4.5 |
| | 4-5 | R-08 | 12 | 30 | 4.8 |
| | 4-6 | R-09 | 13 | 32 | 4.7 |
| | 4-7 | R-10 | 13 | 34 | 4.8 |
| | 4-8 | R-11 | 10 | 28 | 4.8 |
| Comparative Example | 4-1 | R-12 | 12 | 32 | 5.0 |
| | 4-2 | R-13 | 14 | 38 | 5.8 |
| | 4-3 | R-16 | 16 | 40 | 5.8 |

As is evident from Table 8, the resist composition comprising a sulfonium salt-containing polymer within the scope of the invention shows a high resolution and a low LWR on EUV lithography.

Resist Test 4

ArF Exposure/Negative Development

Examples 5-1 to 5-3 and Comparative Examples 5-1 to 5-2

A trilayer process substrate was prepared by forming a spin-on carbon film (ODL-50 by Shin-Etsu Chemical Co., Ltd., carbon content 80 wt %) of 200 nm thick on a silicon wafer and forming a silicon-containing spin-on hard mask (SHB-A940 by Shin-Etsu Chemical Co., Ltd., silicon content 43 wt %) of 35 nm thick thereon. The resist solution in Table 5 was spin coated on the trilayer process substrate, then baked (PAB) on a hot plate at 100° C. for 60 seconds to form a resist film of 90 nm thick.

Using an ArF excimer laser immersion lithography scanner (NSR-610C by Nikon Corp., NA 1.30, σ 0.98/0.74, dipole opening 90 deg., s-polarized illumination), exposure was carried out with a varying exposure dose. After exposure, the resist film was baked (PEB) at an arbitrary temperature for 60 seconds, developed in butyl acetate developer for 30 seconds, and rinsed with diisoamyl ether.

The mask used herein is a binary mask having an on-mask design corresponding to a 45 nm line/90 nm pitch pattern (actual on-mask size is 4 times because of ¼ image reduction projection exposure). The line pattern printed on the resist through the light-transmissive region was observed under an electron microscope. The optimum exposure (Eop) was the dose (mJ/cm$^2$) that gave a line width of 45 nm. The cross-sectional profile of the pattern formed at the optimum dose was observed under an electron microscope and judged passed or rejected according to the following criterion.

Passed: pattern of perpendicular sidewall; acceptable profile

Rejected: T-top profile with surface layer substantially clogged or inversely tapered profile of pattern with graded sidewall (greater line width nearer to surface layer); unacceptable profile The collapse limit was a minimum width (nm) of lines which could be resolved without collapse when the line size was narrowed by decreasing the exposure dose. A smaller value indicates better collapse resistance.

The test results of the resist materials in Table 5 are shown in Table 9.

TABLE 9

|  |  | Resist | Eop (mJ/cm$^2$) | Profile | Collapse limit (nm) |
|---|---|---|---|---|---|
| Example | 5-1 | R-05 | 35 | Passed | 32 |
|  | 5-2 | R-06 | 34 | Passed | 34 |
|  | 5-3 | R-07 | 34 | Passed | 35 |
| Comparative | 5-1 | R-14 | 35 | Rejected | 38 |
| Example | 5-2 | R-15 | 38 | Rejected | 37 |

It is evident from the data of Table 9 that when the resist compositions within the scope of the invention are subjected to organic solvent negative development, patterns of good profile having collapse resistance are formed.

The resist composition comprising the photoacid generator polymer according to the invention is low diffusive and successful in achieving a high resolution. Upon exposure to high-energy radiation, no or little volatile decomposition products are formed. Upon exposure in high vacuum as in the case of EUV lithography, effects of reduced outgassing and the like are expectable as compared with the existing resists.

While the invention has been illustrated and described in typical embodiments, it is not intended to be limited to the details shown. Any modified embodiments having substantially the same features and achieving substantially the same results as the technical idea disclosed herein are within the spirit and scope of the invention.

Japanese Patent Application No. 2012-135462 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt comprising (a) a polymerizable substituent, (b) a sulfonium cation, and (c) a sulfonate anion within a common molecule, capable of generating a sulfonic acid in response to high-energy radiation or heat, wherein the sulfonium salt has a structure of general formula (1A), (1B) or (1C):

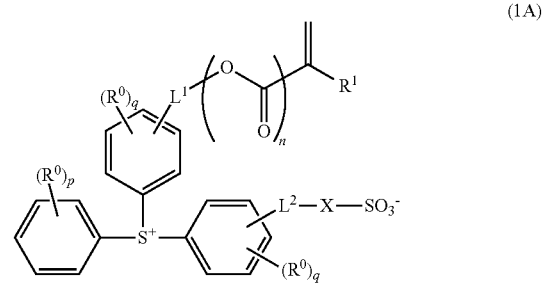

(1A)

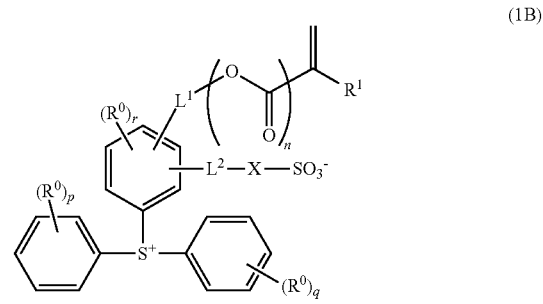

(1B)

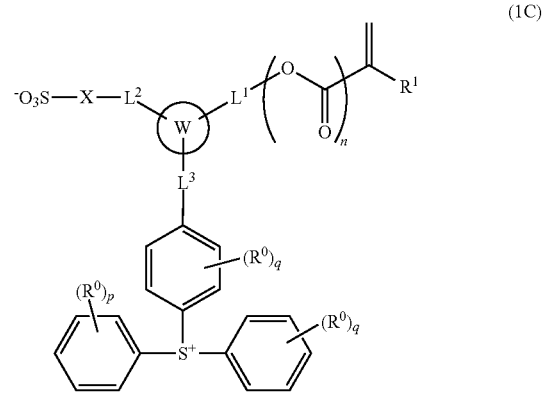

(1C)

wherein R$^0$ is a C$_1$-C$_{20}$ monovalent hydrocarbon group which may be substituted with or separated by a heteroatom, R$^1$ is hydrogen, methyl or trifluoromethyl, L$^1$, L$^2$ and L$^3$ are each independently a single bond or a C$_1$-C$_{20}$ straight, branched or cyclic, divalent hydrocarbon group which may be substituted with or separated by a heteroatom, X is a C$_1$-C$_5$ divalent alkylene group in which some or all hydrogen atoms may be substituted by fluorine atoms, W is a C$_3$-C$_{30}$ trivalent aliphatic or aromatic ring, n is 0 or 1, p is an integer of 0 to 5, q is an integer of 0 to 4, and r is an integer of 0 to 3.

2. The sulfonium salt of claim 1, wherein the sulfonium salt has a structure of general formula (2A), (2B) or (2C):

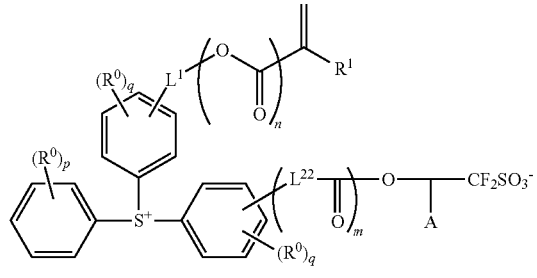
(2A)

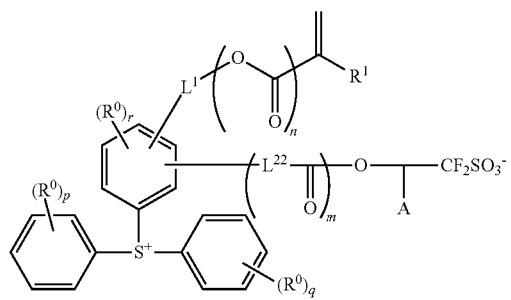
(2B)

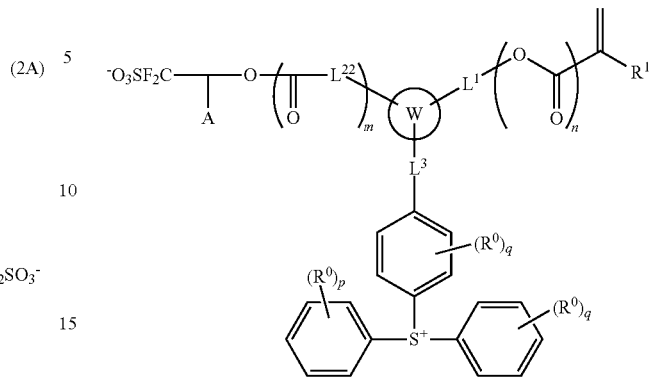
(2C)

wherein $R^0$ is a $C_1$-$C_{20}$ monovalent hydrocarbon group which may be substituted with or separated by a heteroatom, $R^1$ is hydrogen, methyl or trifluoromethyl, $L^1$, $L^2$ and $L^3$ are each independently a single bond or a $C_1$-$C_{20}$ straight, branched or cyclic, divalent hydrocarbon group which may be substituted with or separated by a heteroatom, W is a $C_3$-$C_{30}$ trivalent aliphatic or aromatic ring, n is 0 or 1, p is an integer of 0 to 5, q is an integer of 0 to 4, and r is an integer of 0 to 3, $L^{22}$ is a single bond or a $C_1$-$C_{20}$ straight, branched or cyclic, divalent hydrocarbon group which may be substituted with or separated by a heteroatom, A is hydrogen or trifluoromethyl, and m is 0 or 1.

* * * * *